(12) United States Patent
Ono et al.

(10) Patent No.: US 12,133,719 B2
(45) Date of Patent: Nov. 5, 2024

(54) BLOOD PRESSURE MEASUREMENT DEVICE

(71) Applicants: OMRON Corporation, Kyoto (JP); OMRON HEALTHCARE Co., Ltd., Kyoto (JP)

(72) Inventors: Takashi Ono, Kyoto (JP); Takeshi Kubo, Kyoto (JP); Yasuo Asano, Kyoto (JP); Ko Nakaoka, Kyoto (JP); Yoshihiko Sano, Kyoto (JP); Takanori Nishioka, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 728 days.

(21) Appl. No.: 17/304,799

(22) Filed: Jun. 25, 2021

(65) Prior Publication Data
US 2021/0315466 A1 Oct. 14, 2021

Related U.S. Application Data

(63) Continuation of application No. PCT/JP2019/048035, filed on Dec. 9, 2019.

(30) Foreign Application Priority Data

Dec. 27, 2018 (JP) .................. 2018-246159

(51) Int. Cl.
*A61B 5/0235* (2006.01)
*A61B 5/00* (2006.01)
*A61B 5/022* (2006.01)

(52) U.S. Cl.
CPC ........ *A61B 5/0235* (2013.01); *A61B 5/02233* (2013.01); *A61B 2562/0247* (2013.01)

(58) Field of Classification Search
CPC .............. A61B 5/0235; A61B 5/02233; A61B 2562/0247; A61B 5/681; A61B 5/022;
(Continued)

(56) References Cited

U.S. PATENT DOCUMENTS 5,626,142 A * 5/1997 Marks ................ A61B 5/02233
600/492
6,336,907 B1 * 1/2002 Dono ................... A61H 9/0078
601/150

(Continued)

FOREIGN PATENT DOCUMENTS

JP  2005-230175 A  9/2005
JP  2011-177252 A  9/2011
(Continued)

OTHER PUBLICATIONS

International Preliminary Report on Patentability and Written Opinion of the International Searching Authority issued Jul. 8, 2021 in International (PCT) Application No. PCT/JP2019/048035.

*Primary Examiner* — Alex M Valvis
*Assistant Examiner* — Justin Xu
(74) *Attorney, Agent, or Firm* — Wenderoth, Lind & Ponack, L.L.P.

(57) ABSTRACT

Provided is a blood pressure measurement device capable of discharging a fluid from three cuffs even when either one of a pump valve or an on-off valve fails, that includes a pump including a pump valve; a first flow path including a first on-off valve and fluidly connecting the pump and a sensing cuff; a second flow path branching from the first flow path between the pump and the first on-off valve, including a second on-off valve, a third on-off valve, and a fourth on-off valve, and connecting the pump and atmosphere; a third flow path branching from an intermediate portion between the second on-off valve and the third on-off valve and fluidly connecting the pump and the tensile cuff; and a fourth flow (Continued)

path branching from an intermediate portion between the third on-off valve and the fourth on-off valve and fluidly connecting the pump and the pressing cuff.

5 Claims, 37 Drawing Sheets

(58) Field of Classification Search
CPC . A61B 5/02141; A61B 5/0225; A61B 5/6824; A61B 5/02108; A47C 27/082; A47C 27/083; A47C 27/10; A47C 7/467; A61H 2201/0134; A61H 2201/0146; A61H 2201/1623; A61H 2201/1635; A61H 2201/164; A61H 2201/165; A61H 7/002; A61H 9/0078
See application file for complete search history.

(56) References Cited

U.S. PATENT DOCUMENTS

| | | | |
|---|---|---|---|
| 2011/0160599 A1* | 6/2011 | Kobayashi | A61B 5/021 600/494 |
| 2015/0173931 A1* | 6/2015 | Tanaka | A63B 24/0087 482/91 |
| 2019/0063624 A1* | 2/2019 | Yin | F16K 15/207 |

FOREIGN PATENT DOCUMENTS

| | | |
|---|---|---|
| JP | 2017-23874 A | 2/2017 |
| JP | 2018-143557 A | 9/2018 |

* cited by examiner

[Fig. 1]
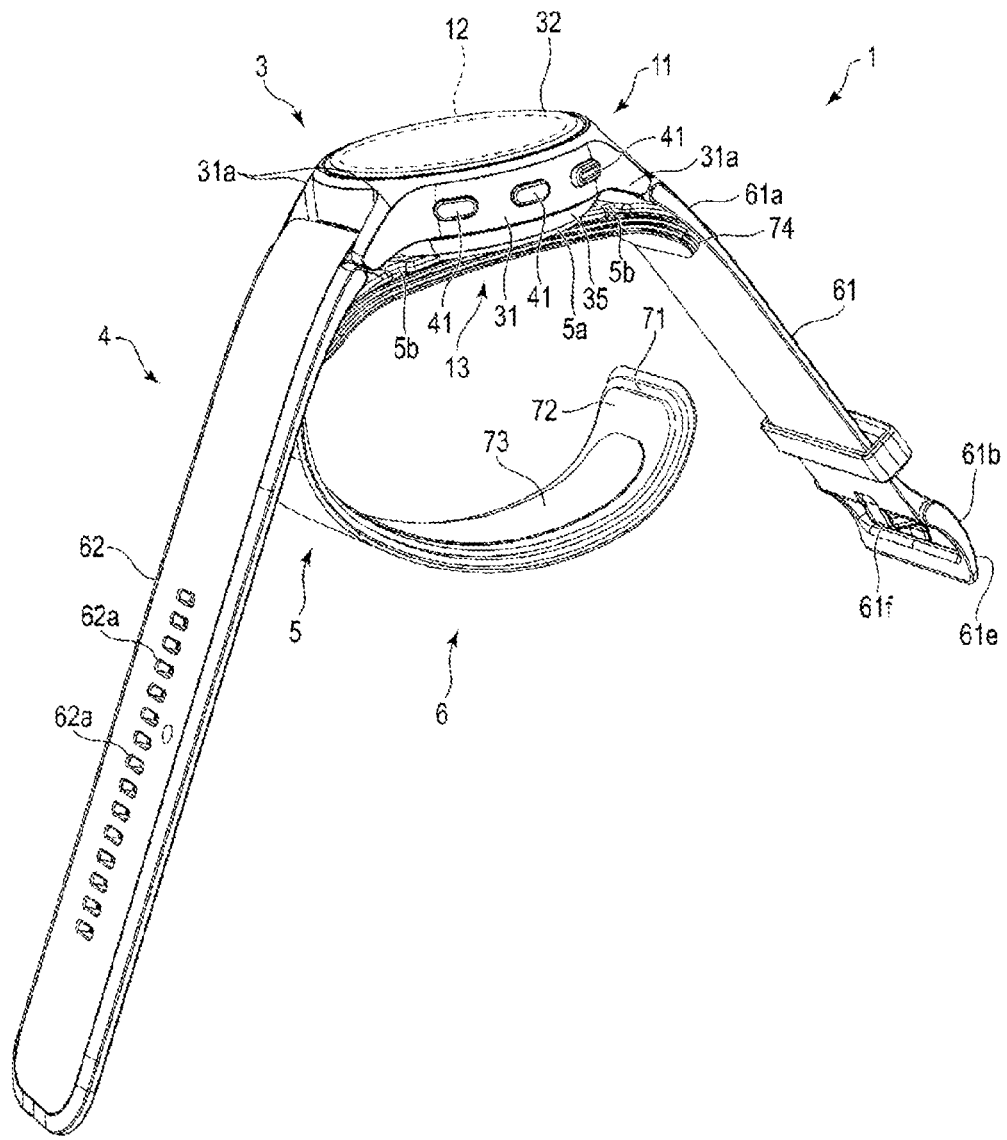

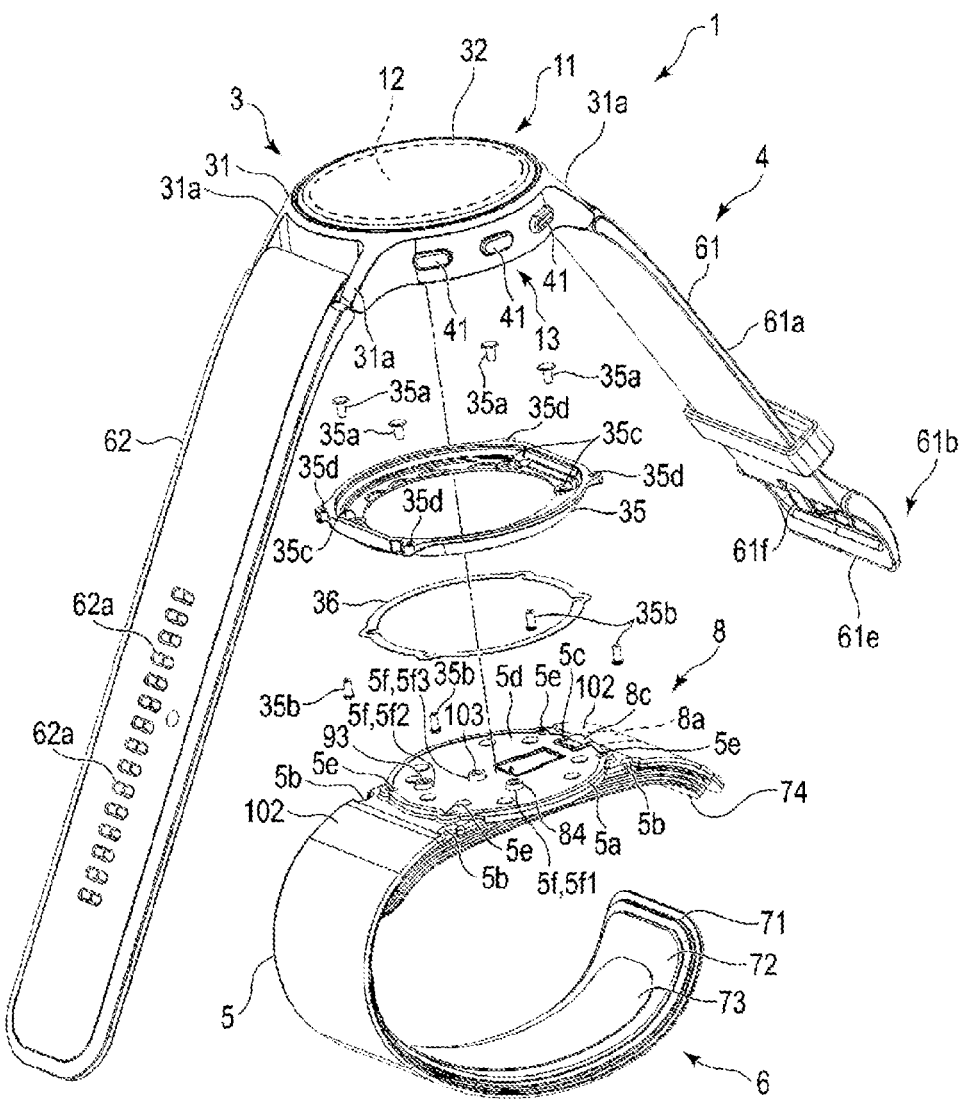
[Fig. 2]

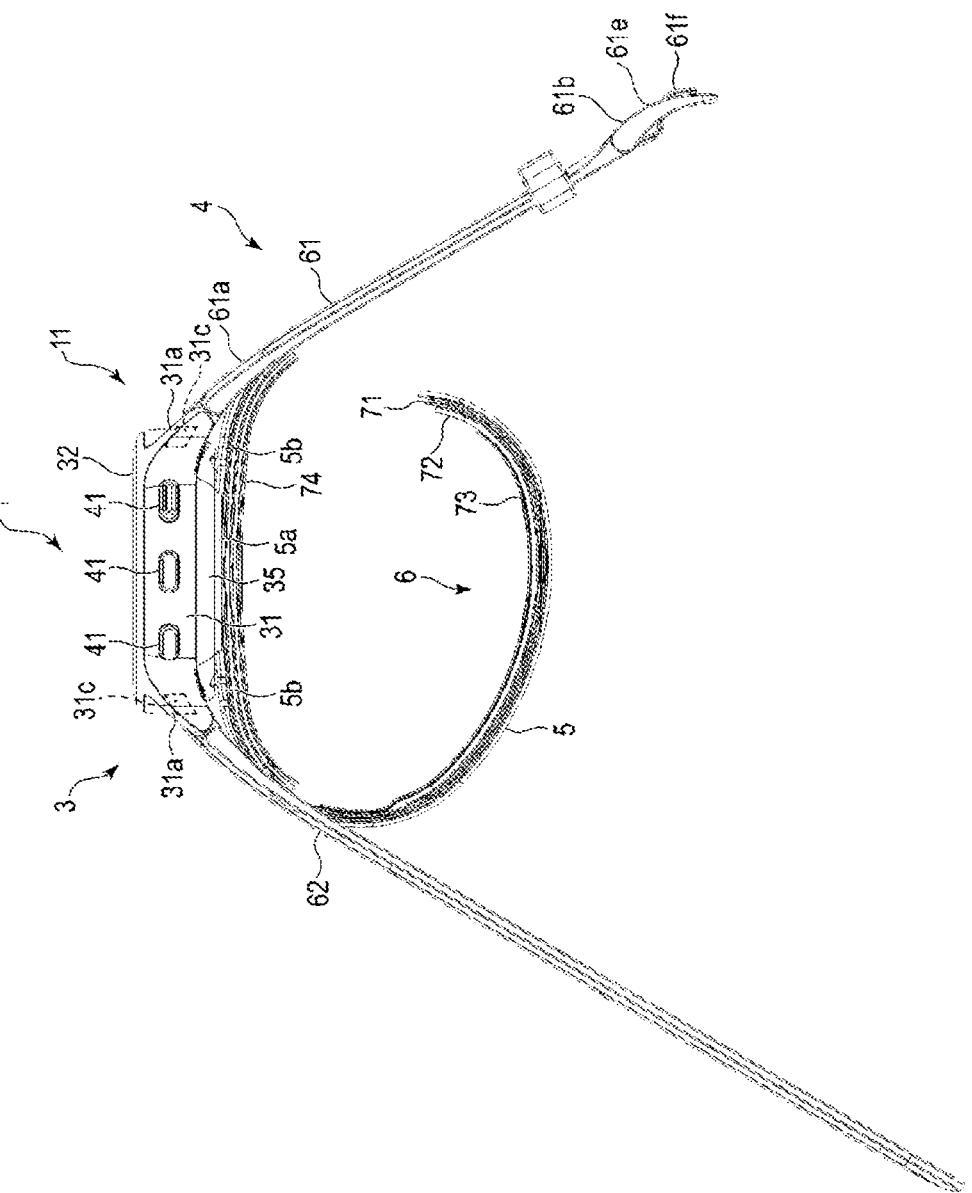

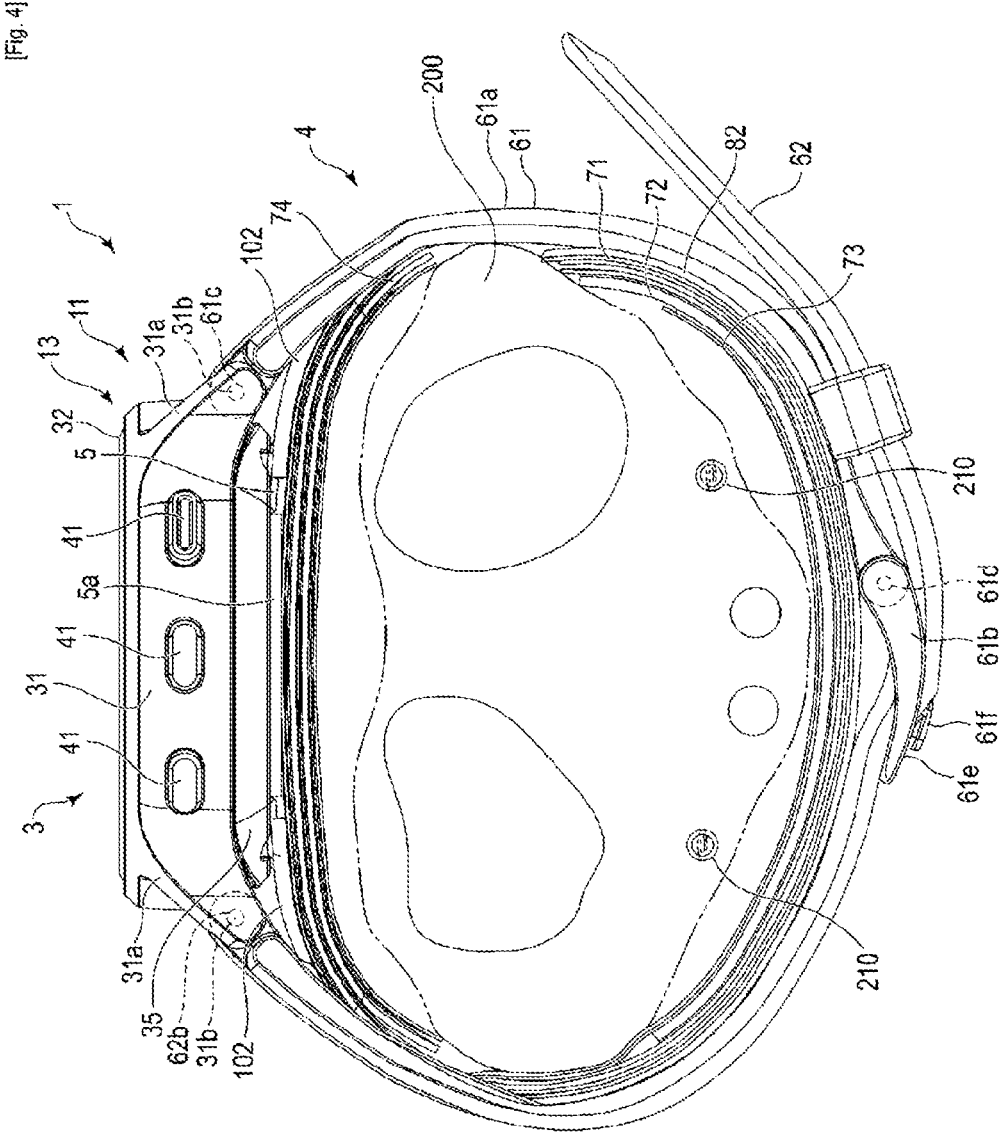
[Fig. 4]

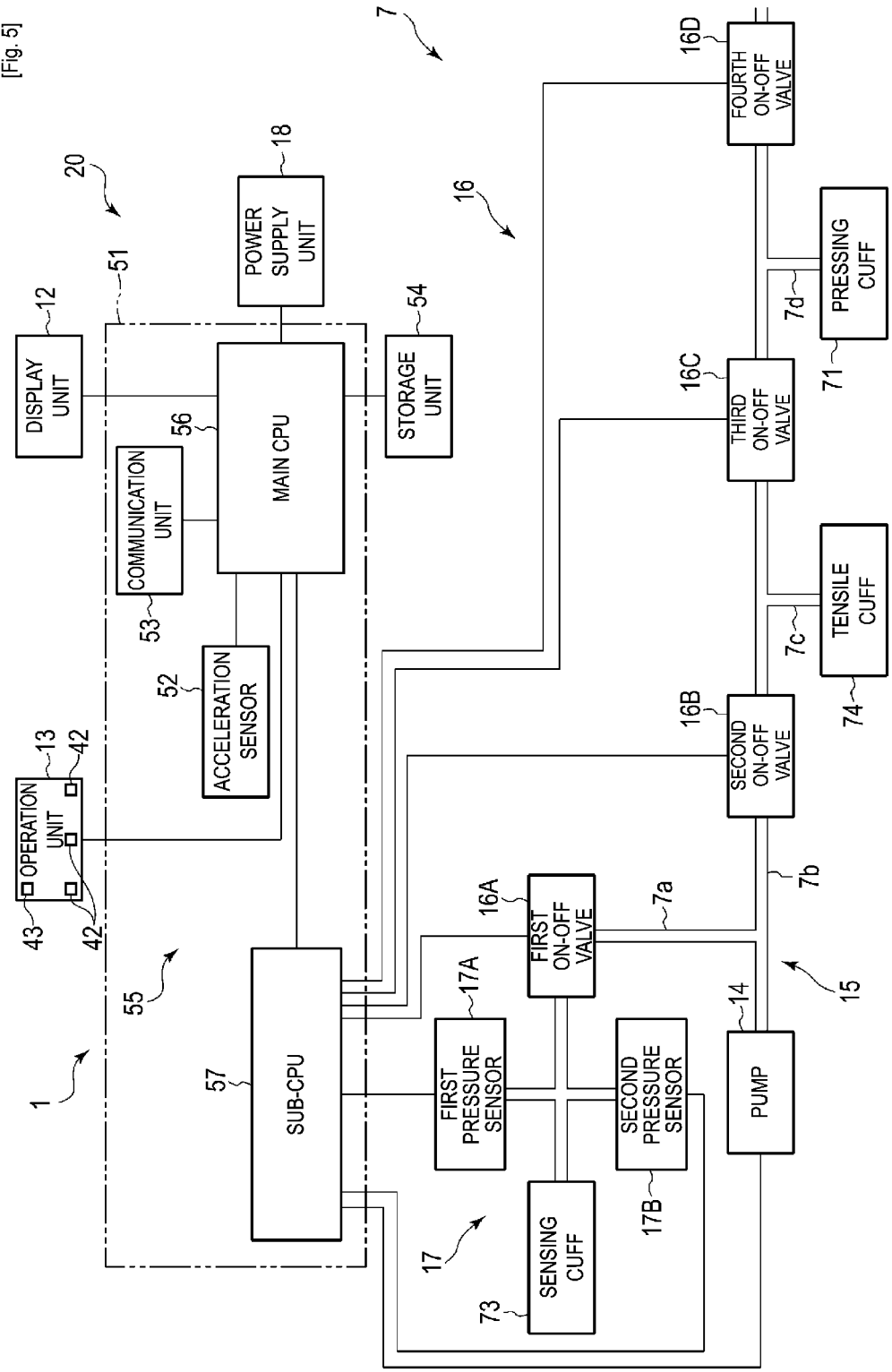
[Fig. 5]

[Fig. 6]
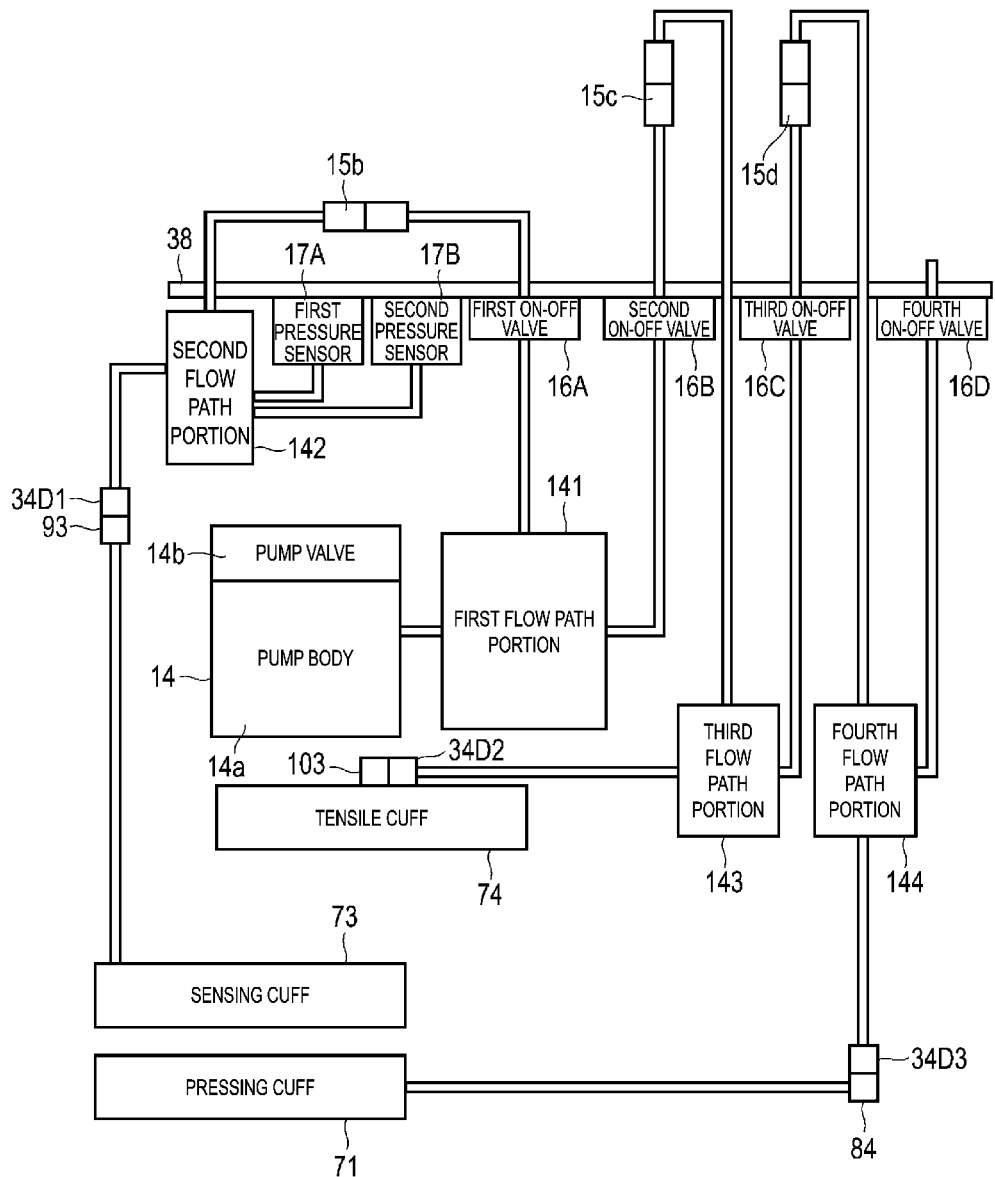

[Fig. 7]
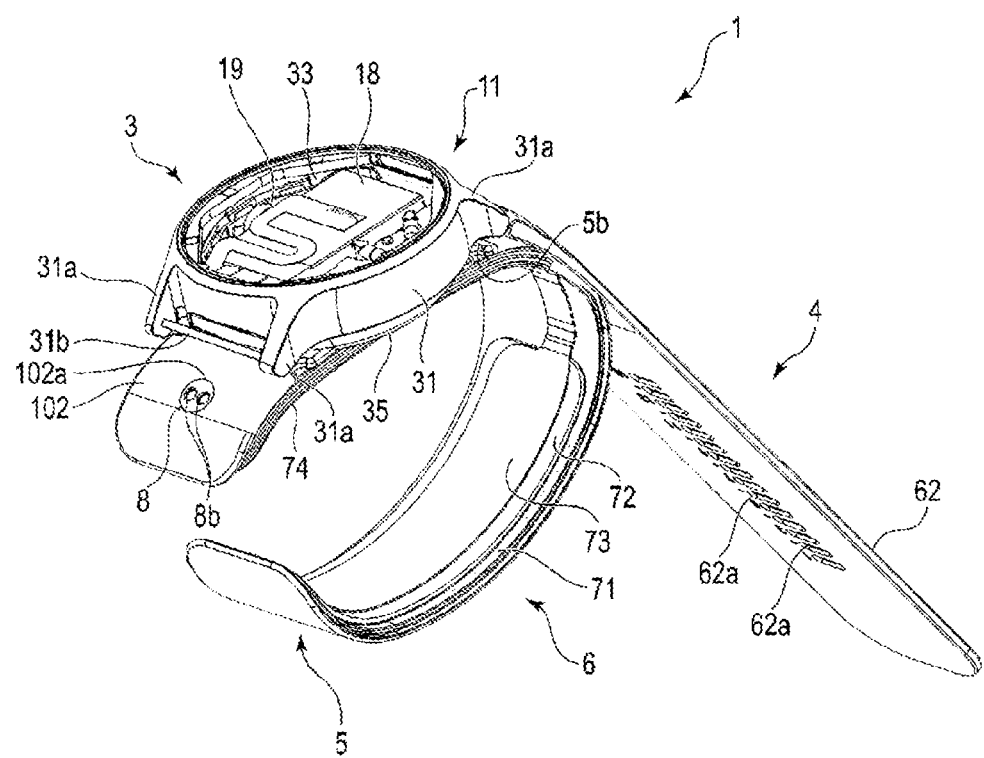

[Fig. 8]
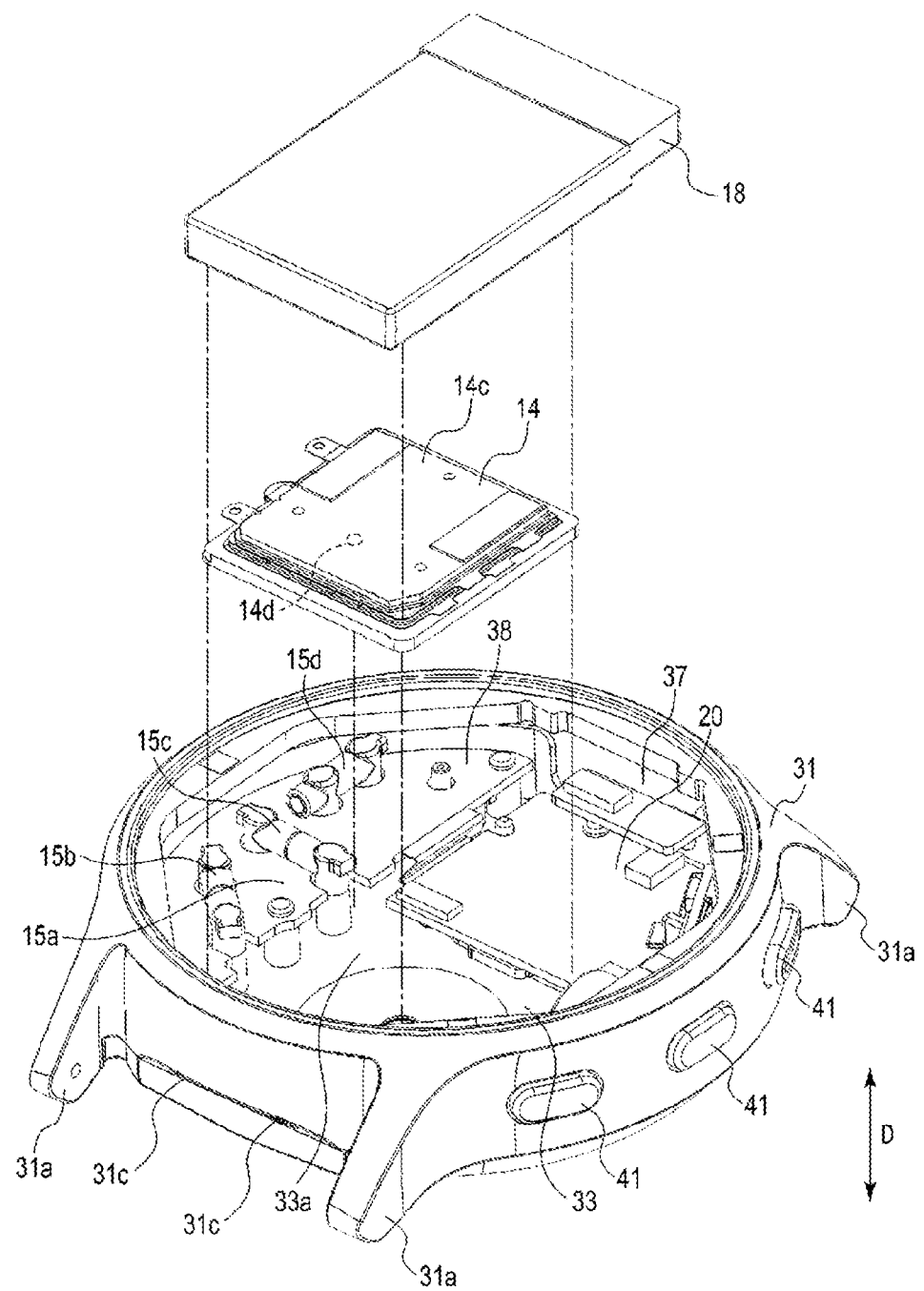

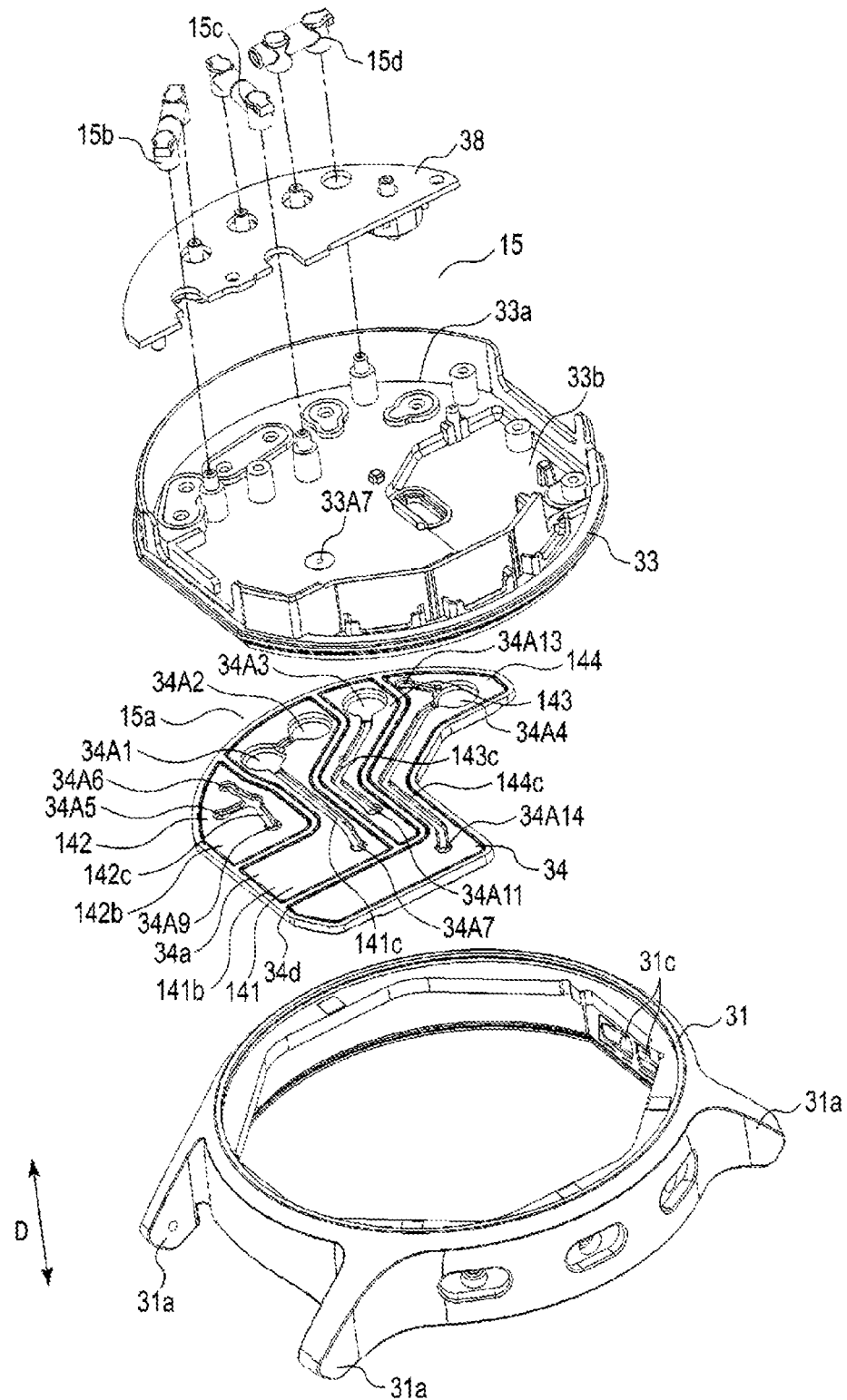
[Fig. 9]

[Fig. 10]
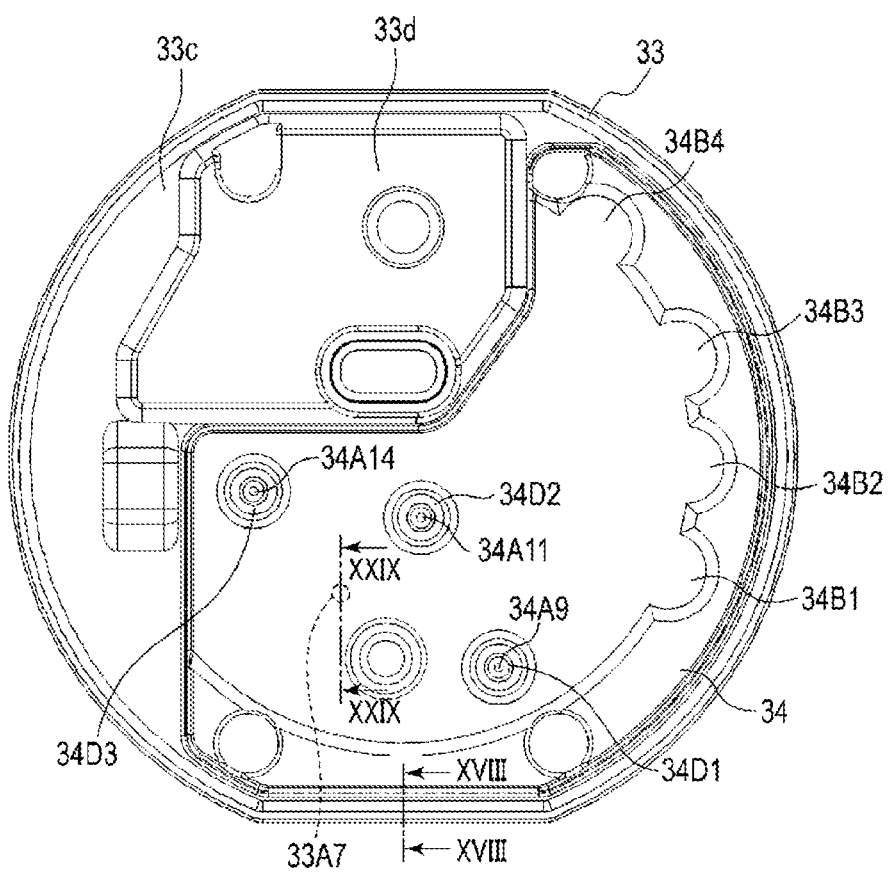

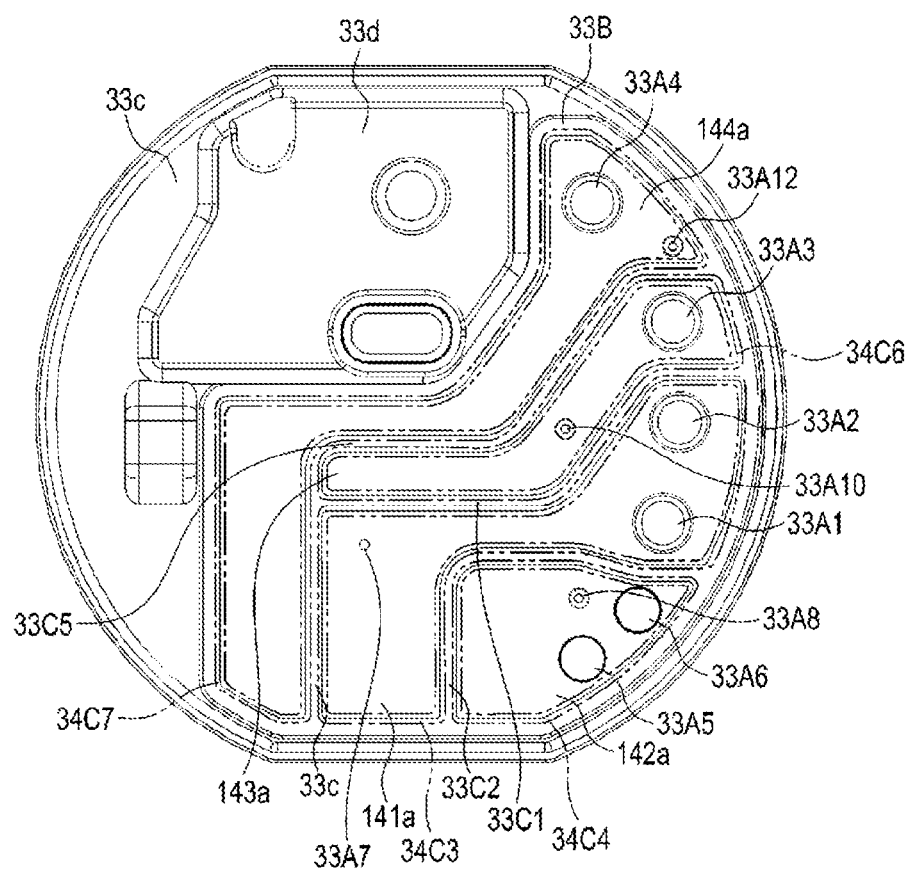
[Fig. 11]

[Fig. 12]
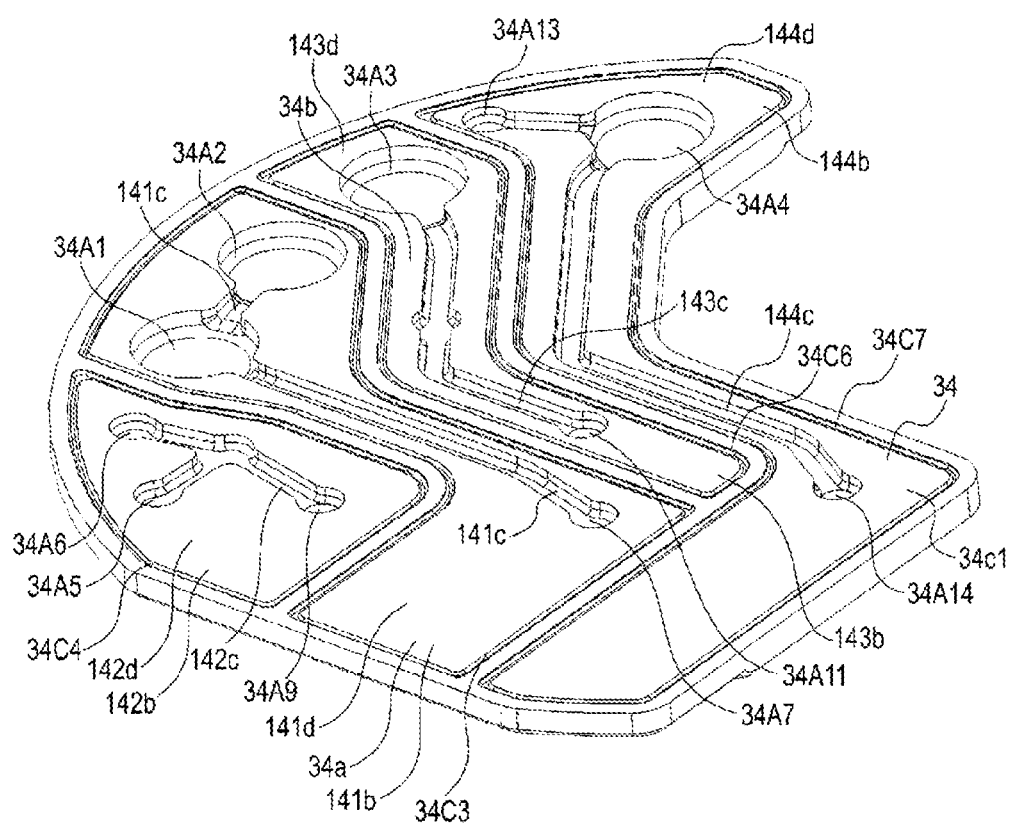

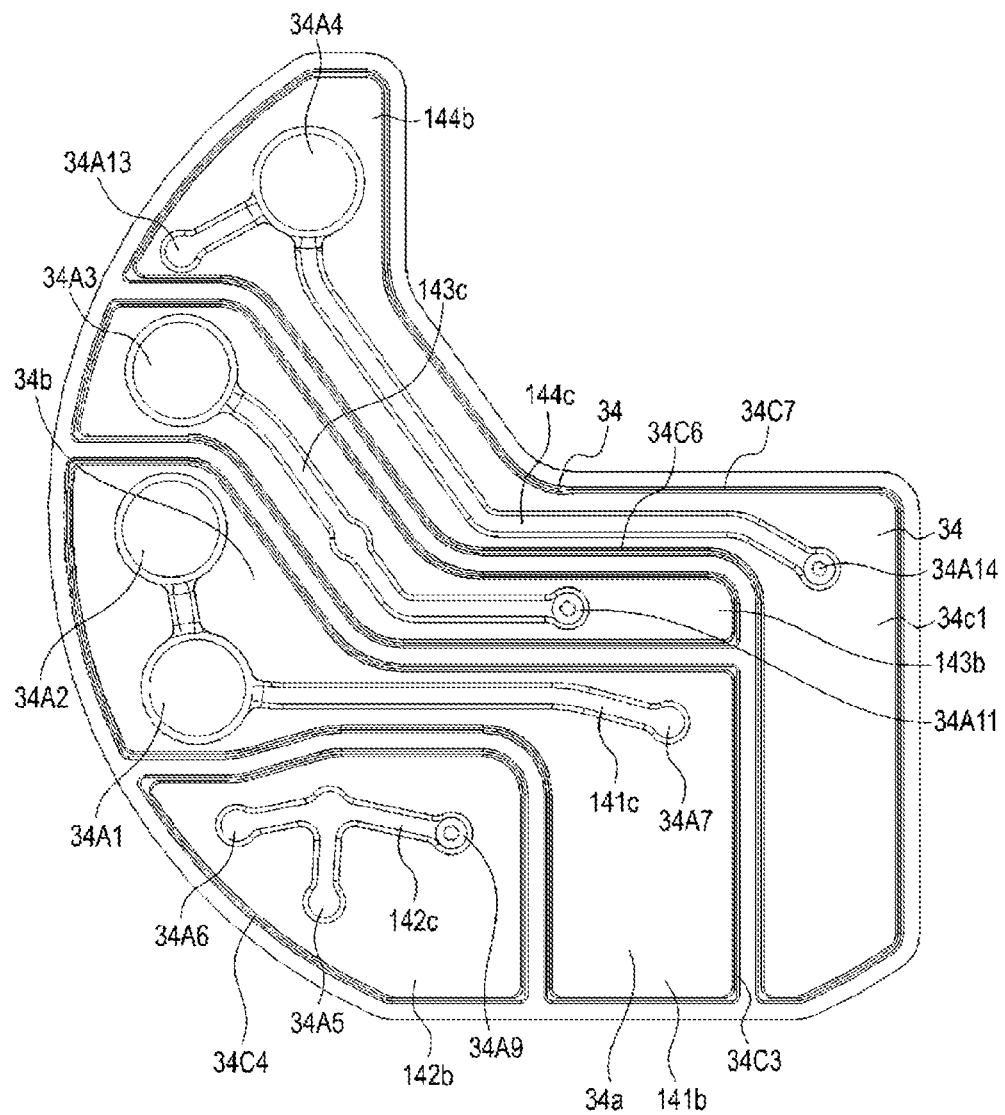
[Fig. 13]

[Fig. 14]
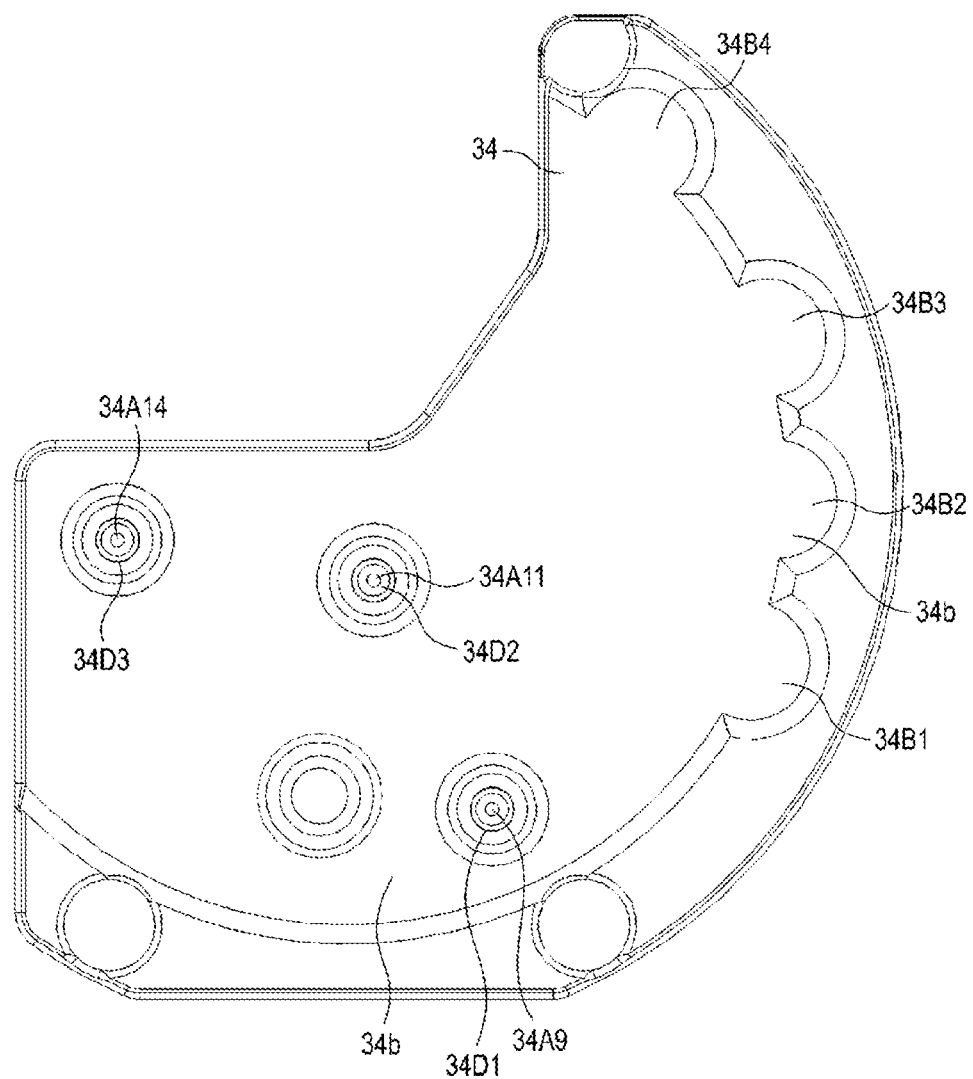

[Fig. 15]
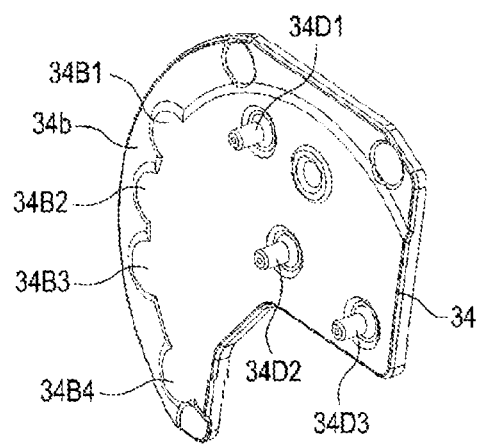
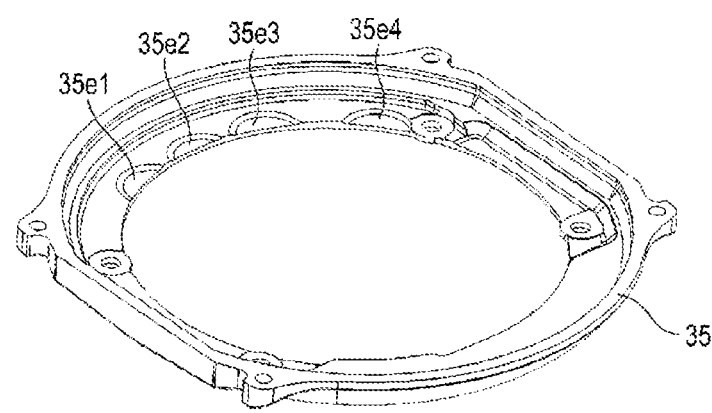

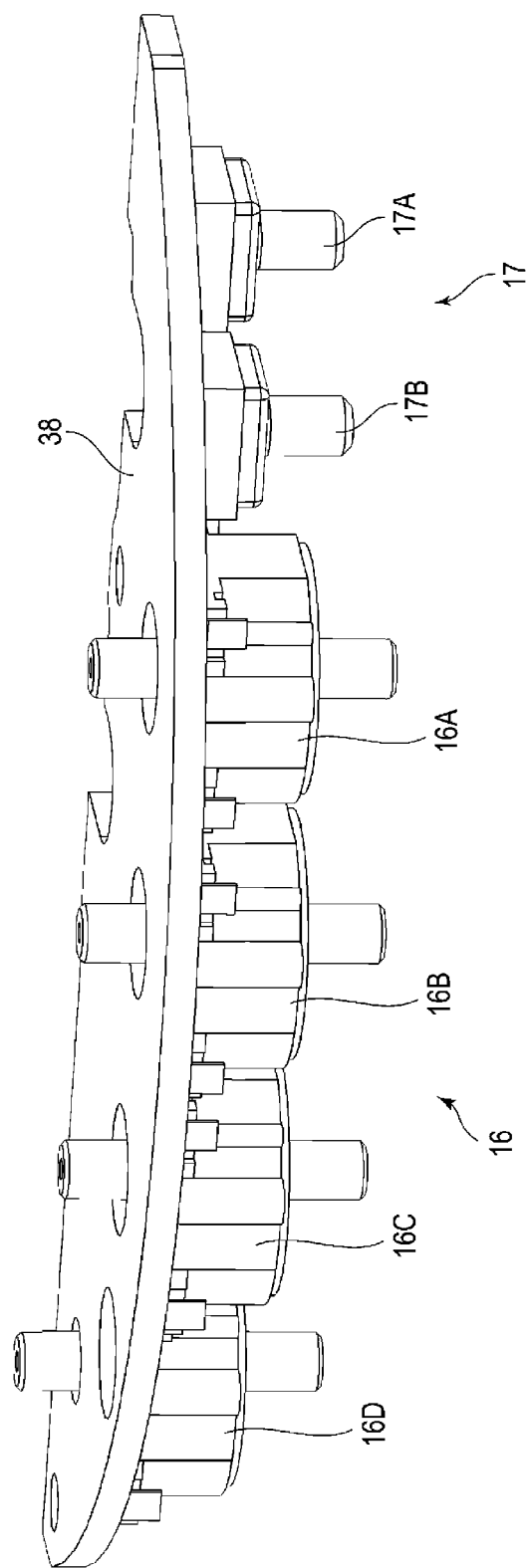
[Fig. 16]

[Fig. 17]
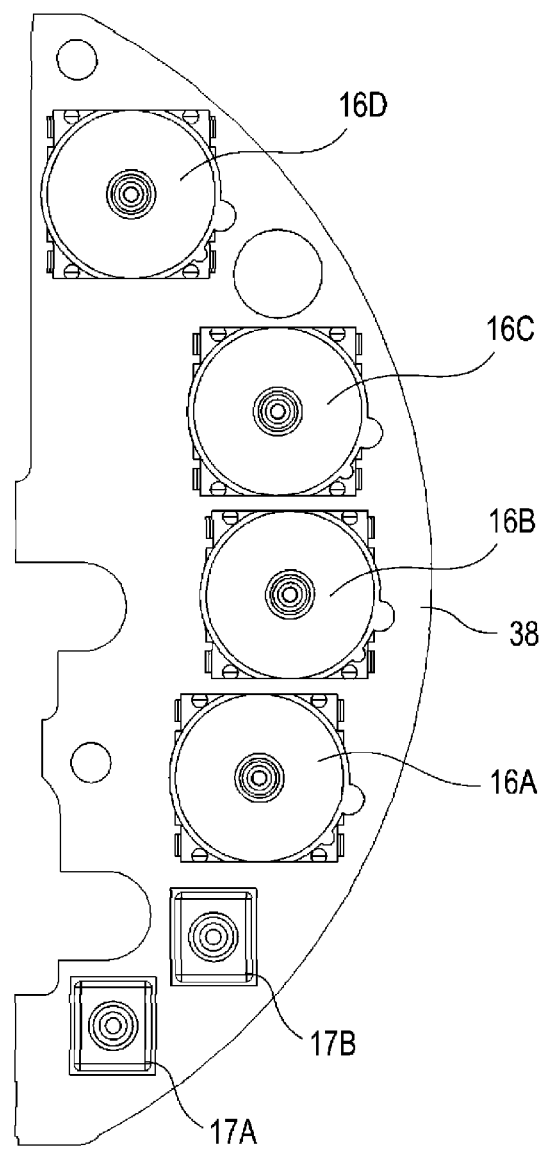

[Fig. 18]
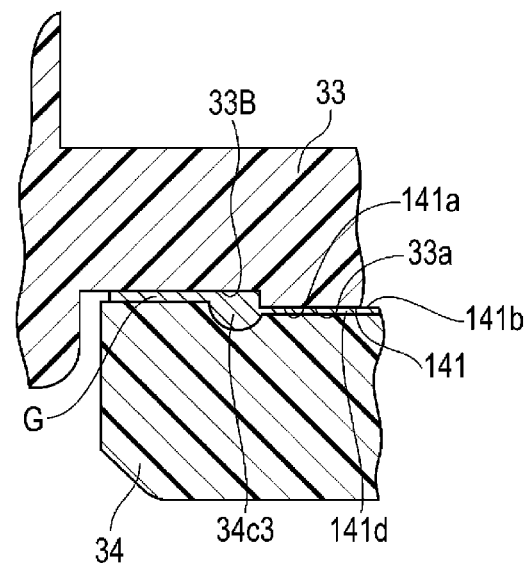
[Fig. 19]
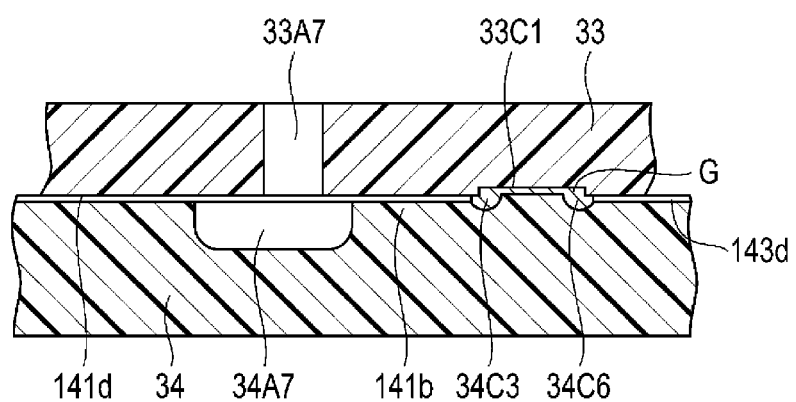

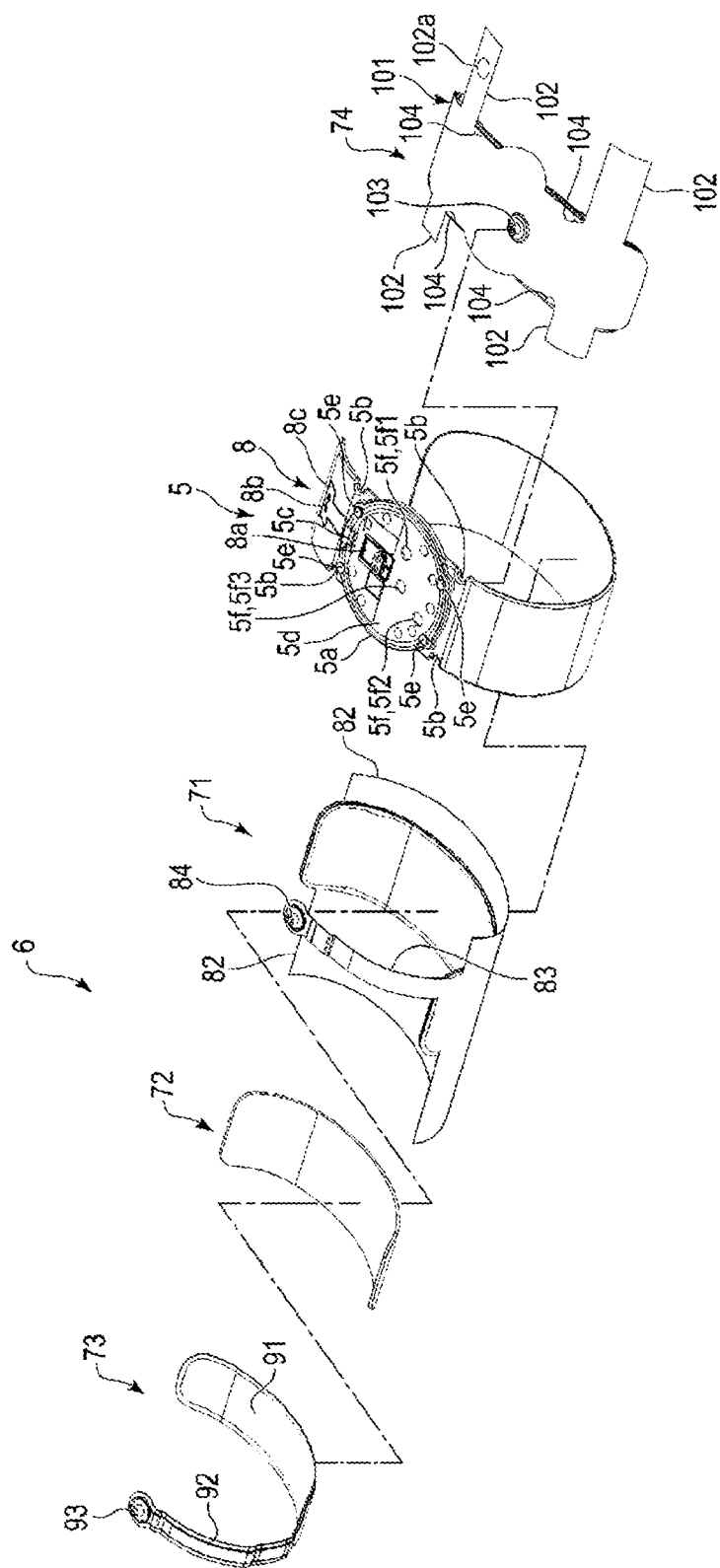

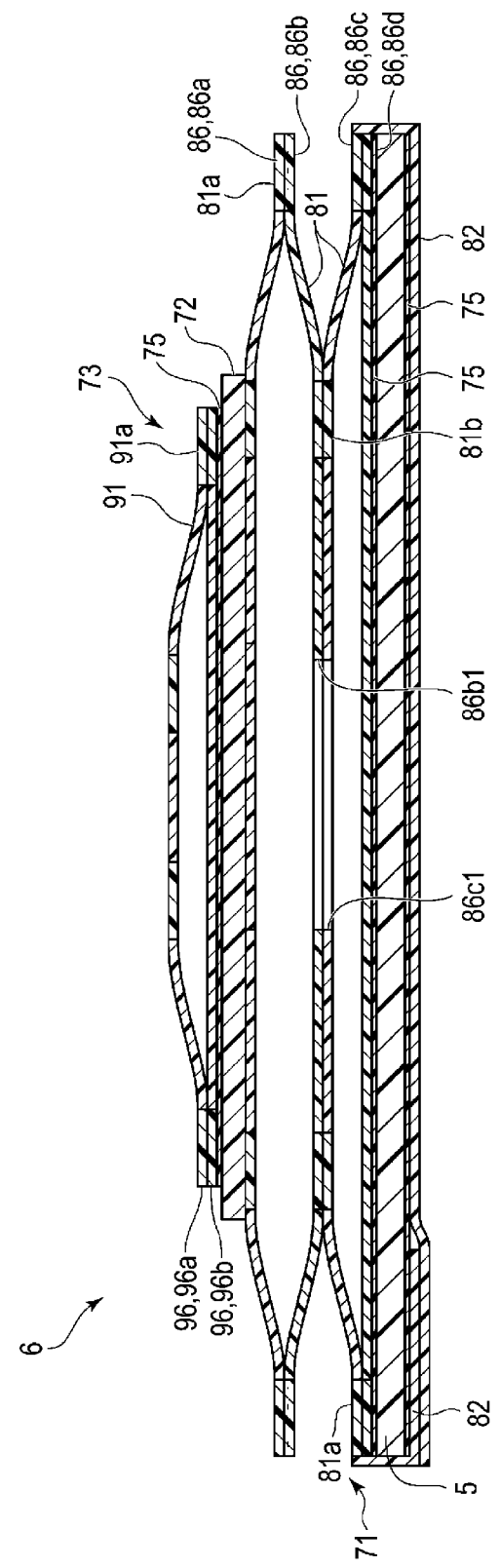

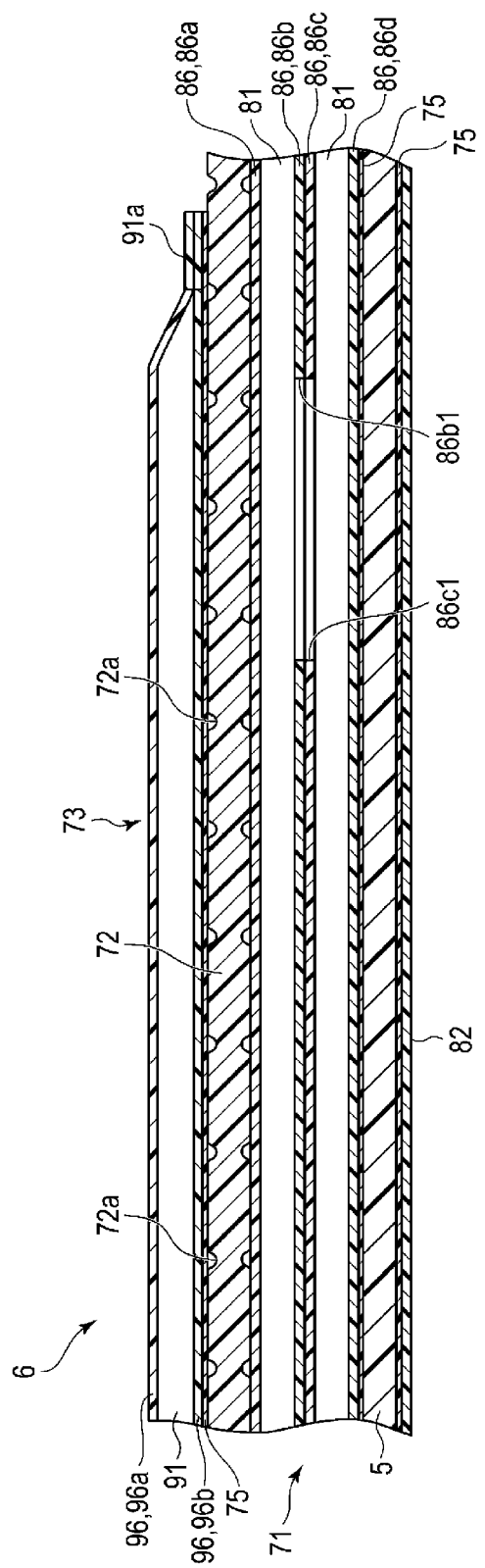

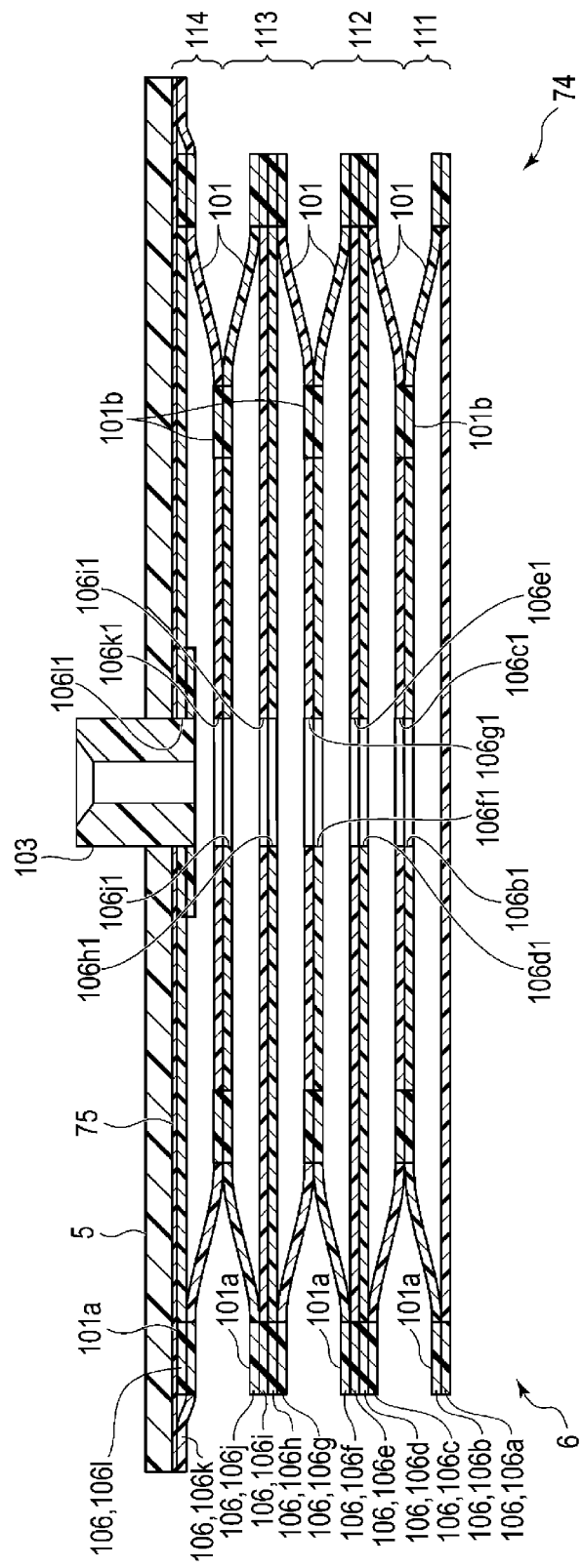

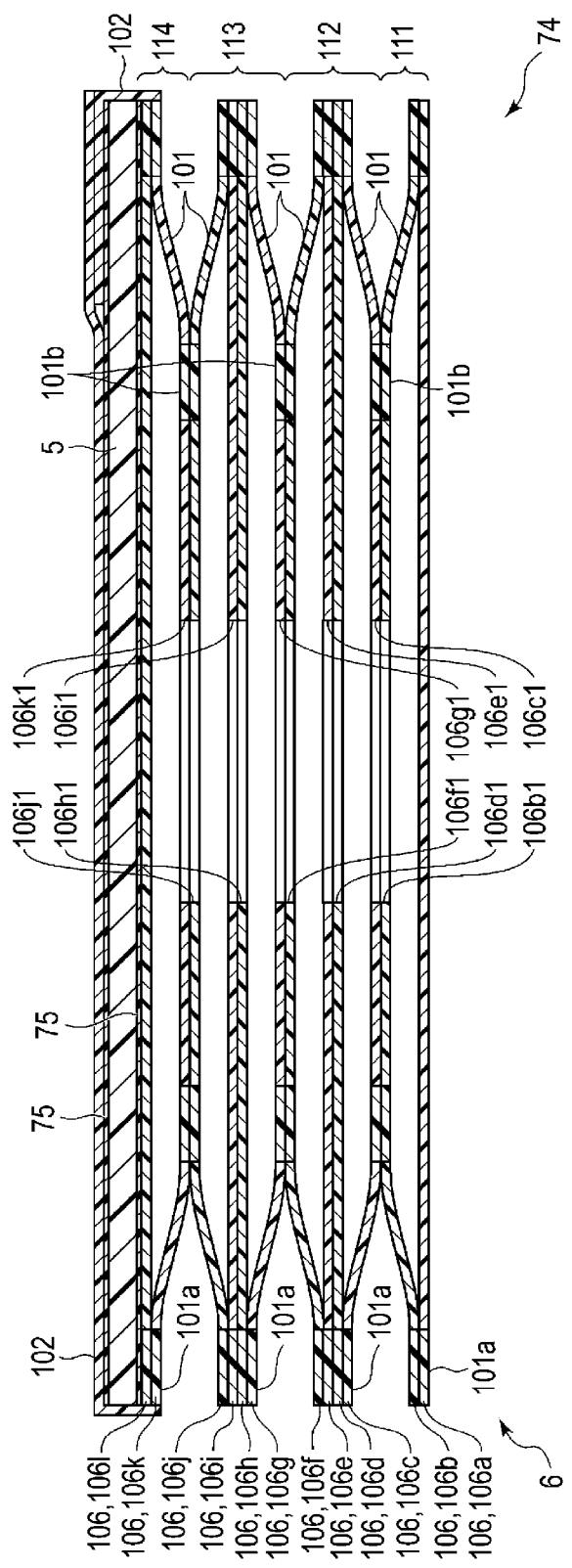
[Fig. 24]

[Fig. 25]
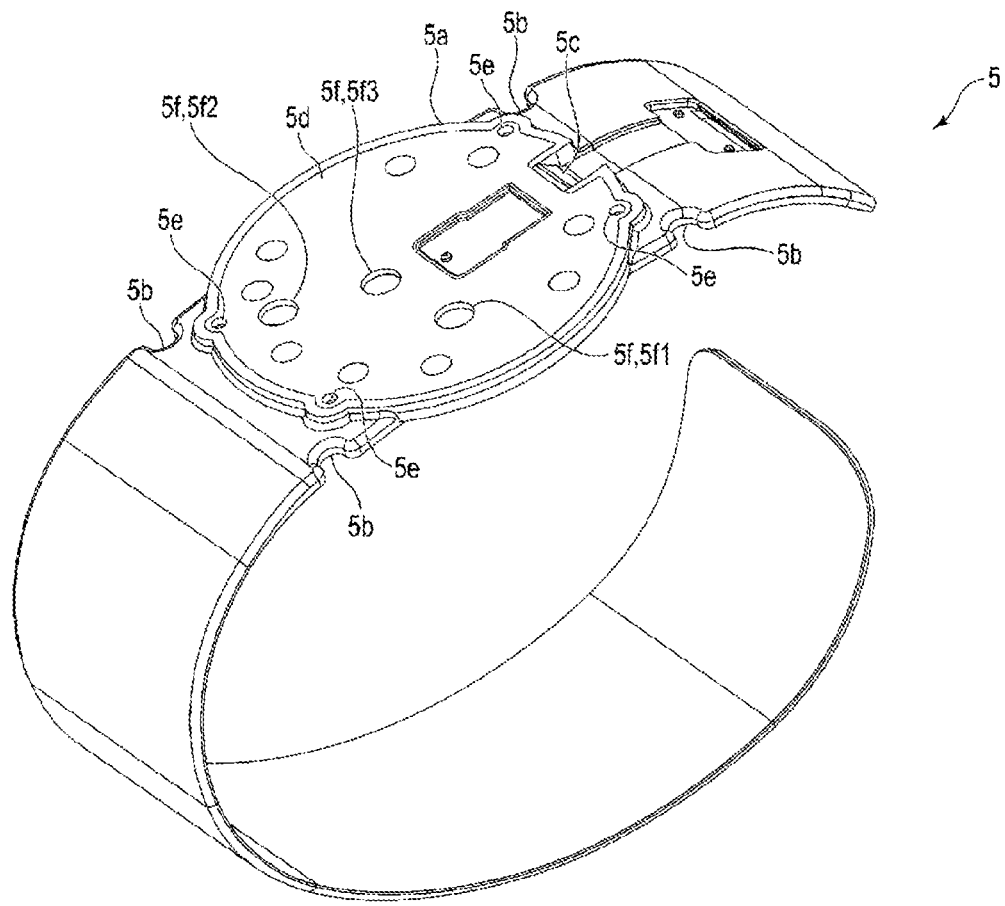

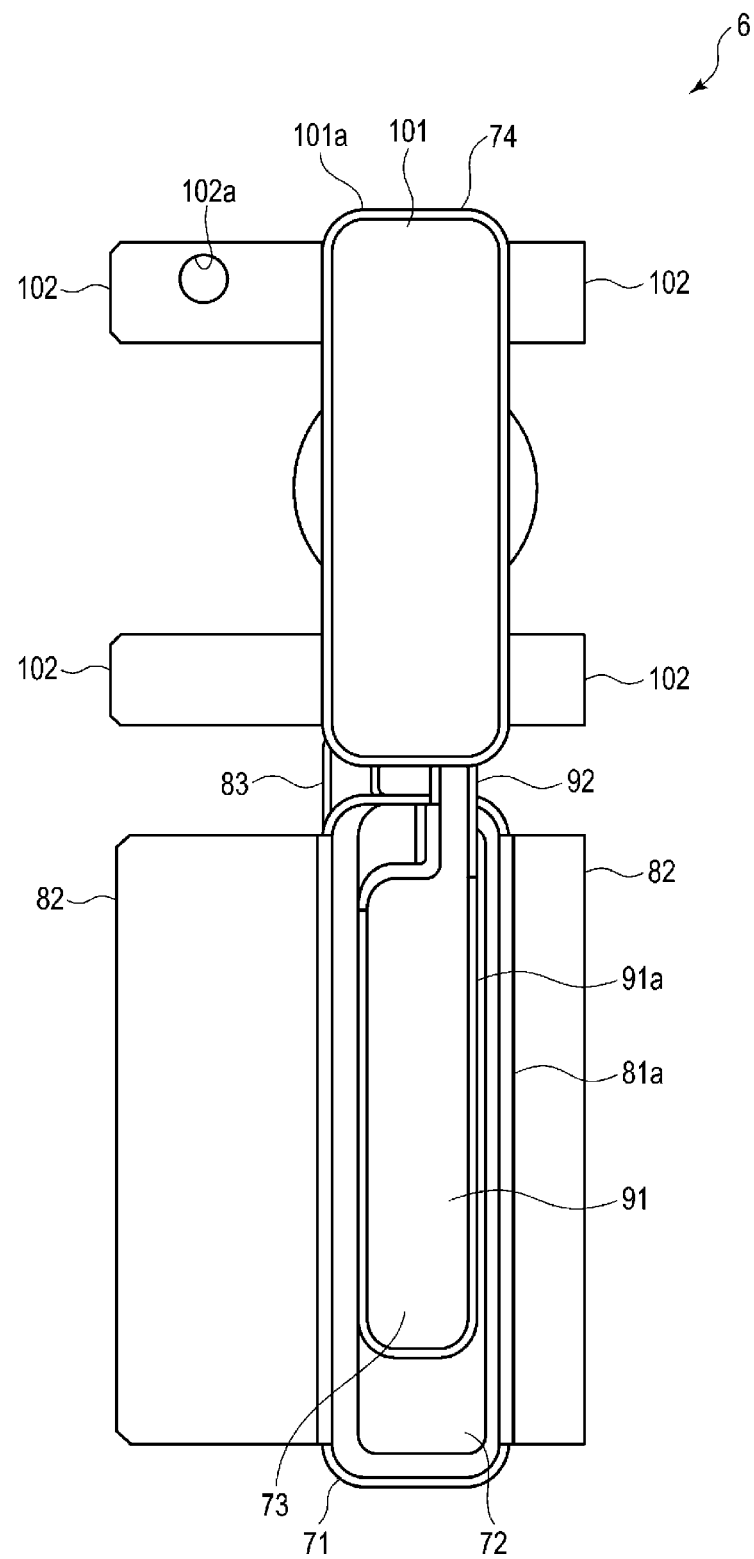
[Fig. 26]

[Fig. 27]
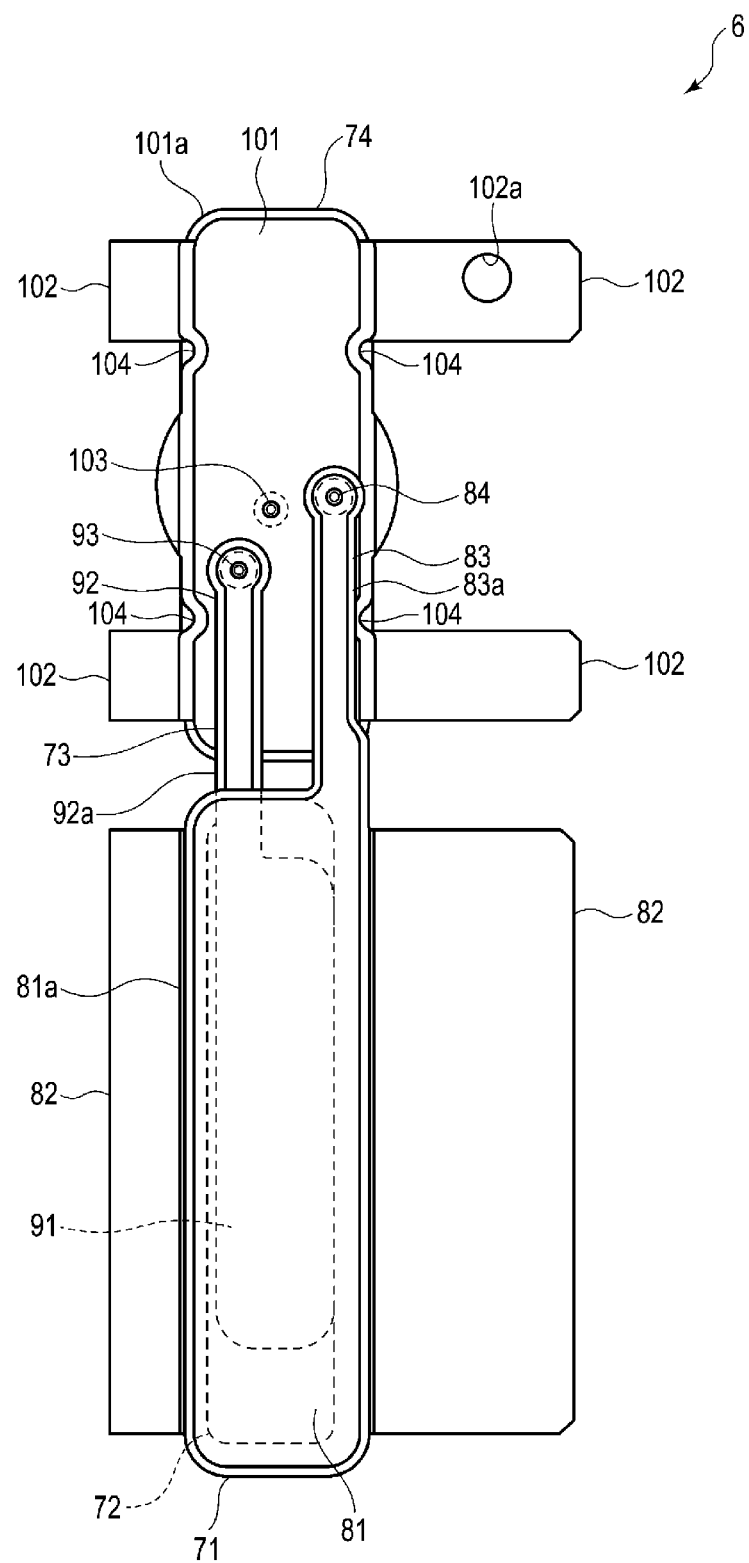

[Fig. 28]
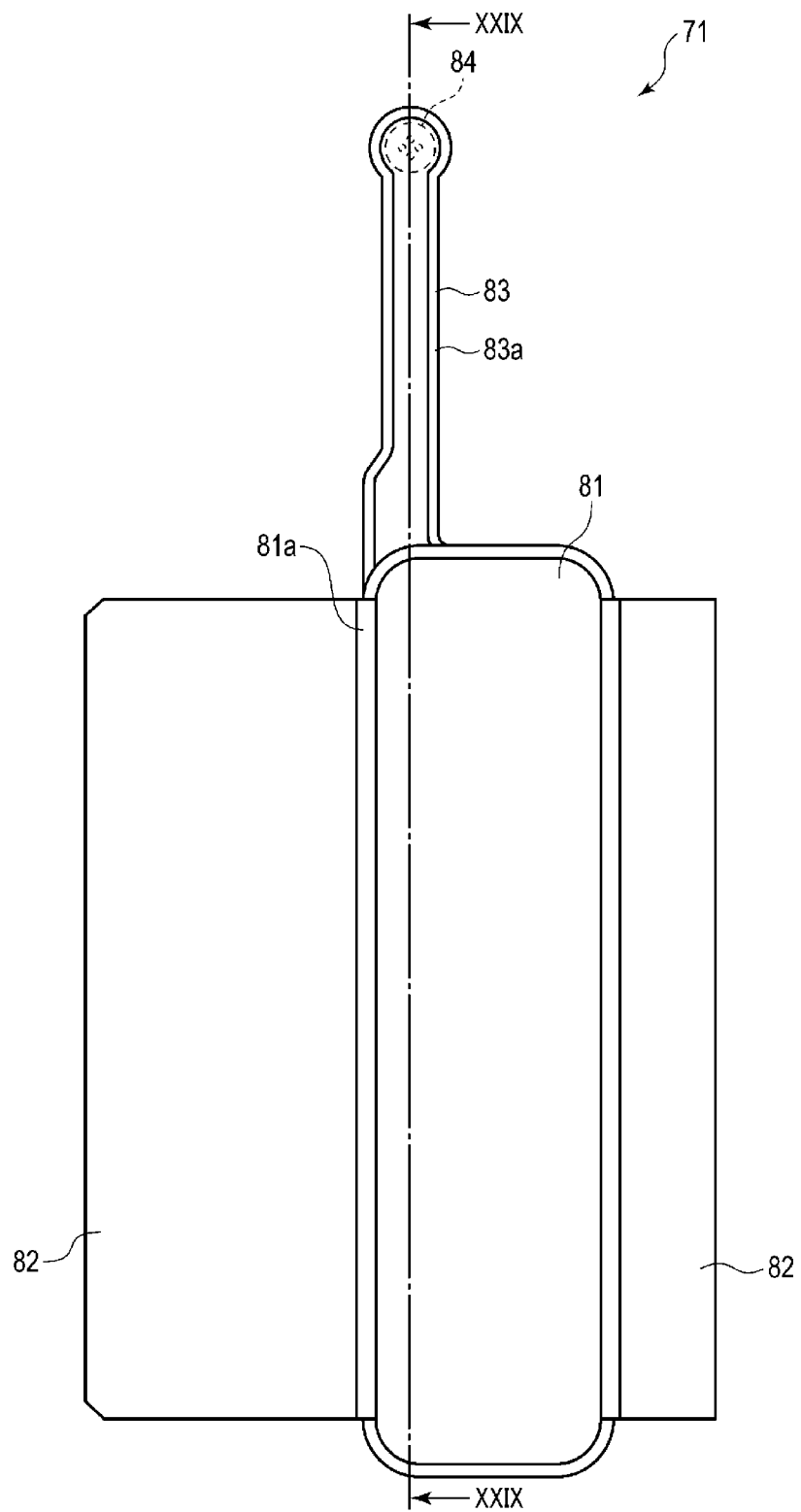

[Fig. 29]
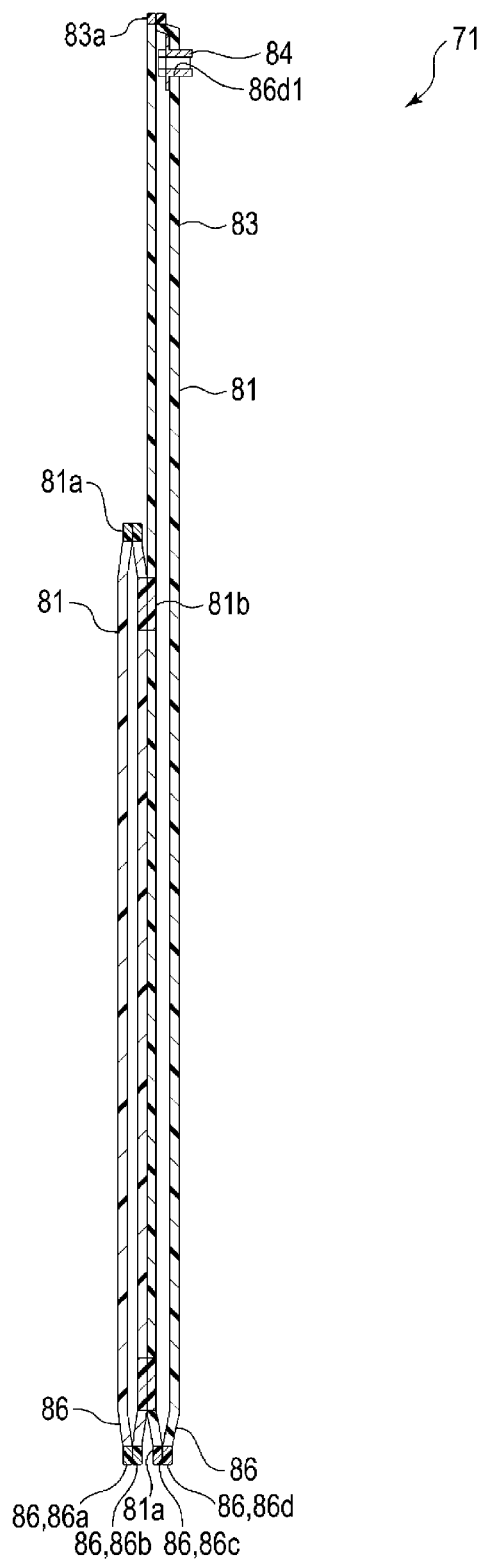

[Fig. 30]
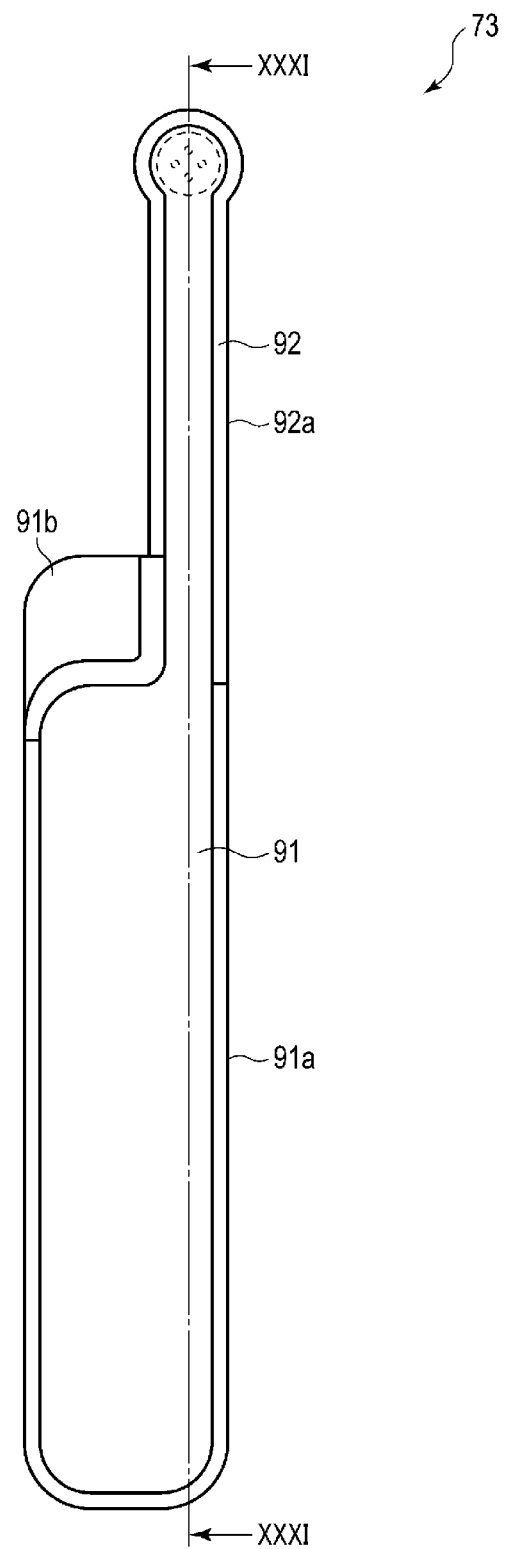

[Fig. 31]
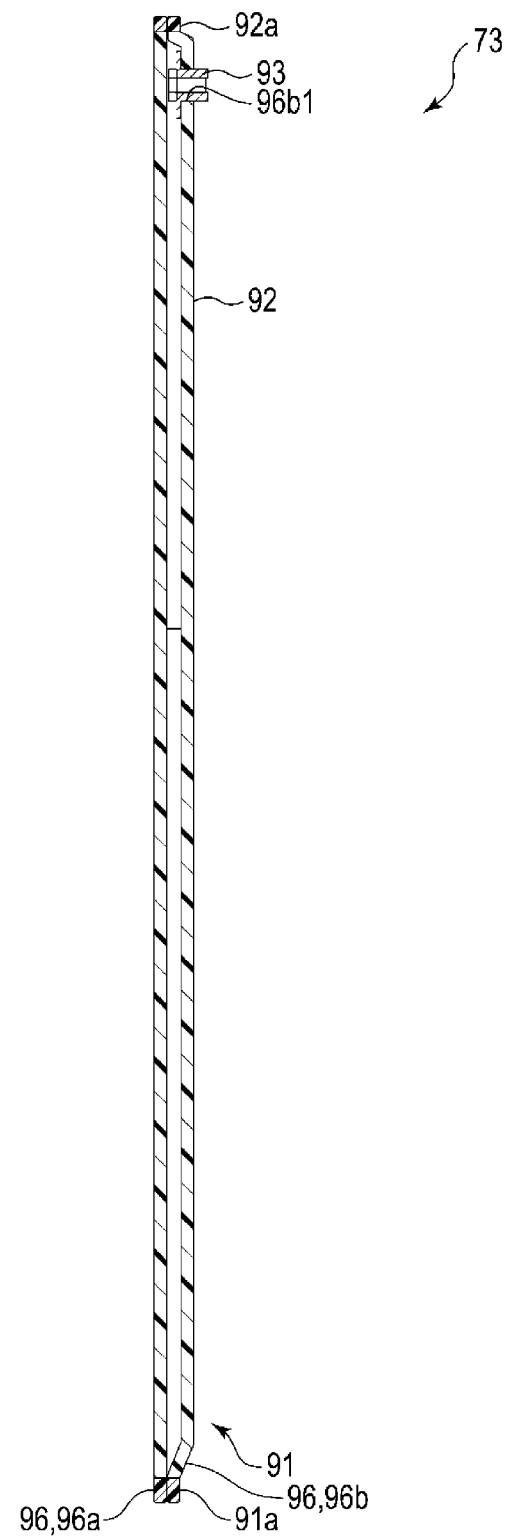

[Fig. 32]
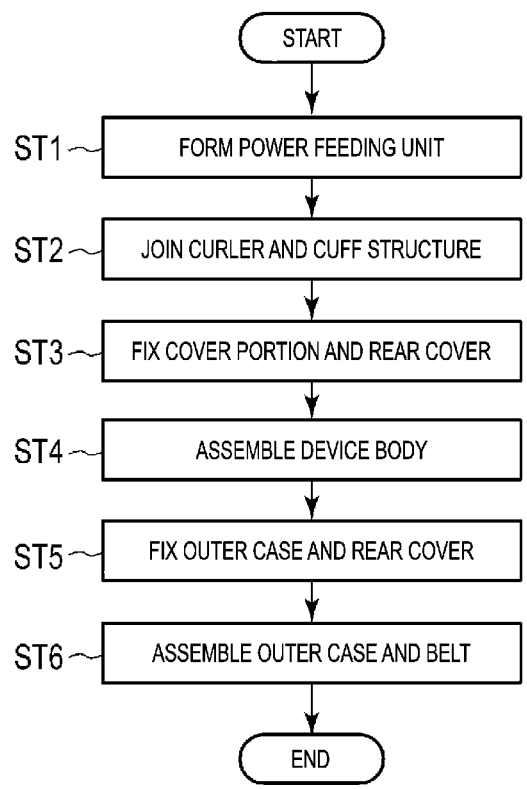

[Fig. 33]
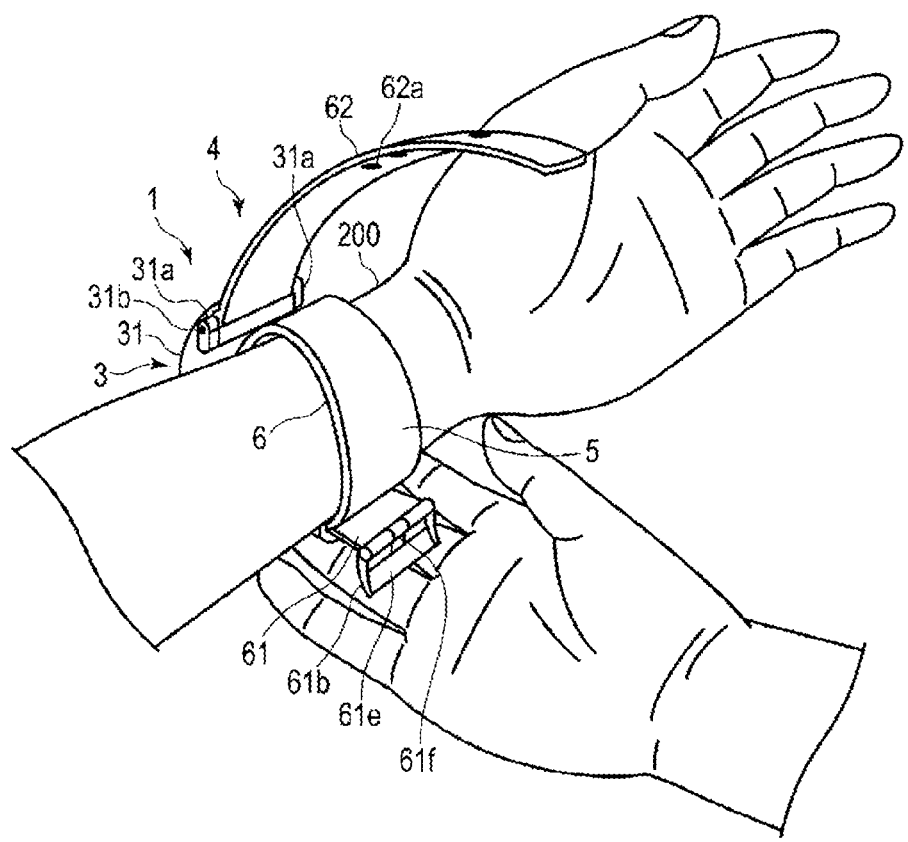

[Fig. 34]
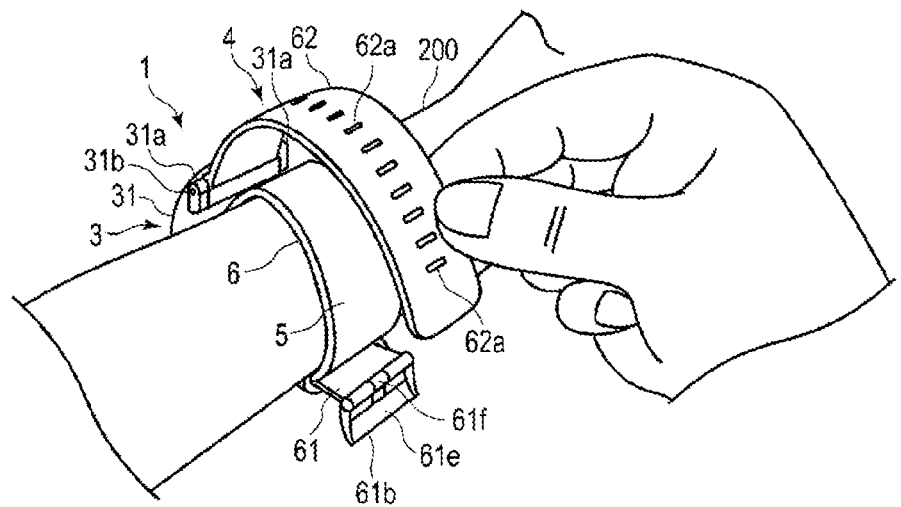
[Fig. 35]
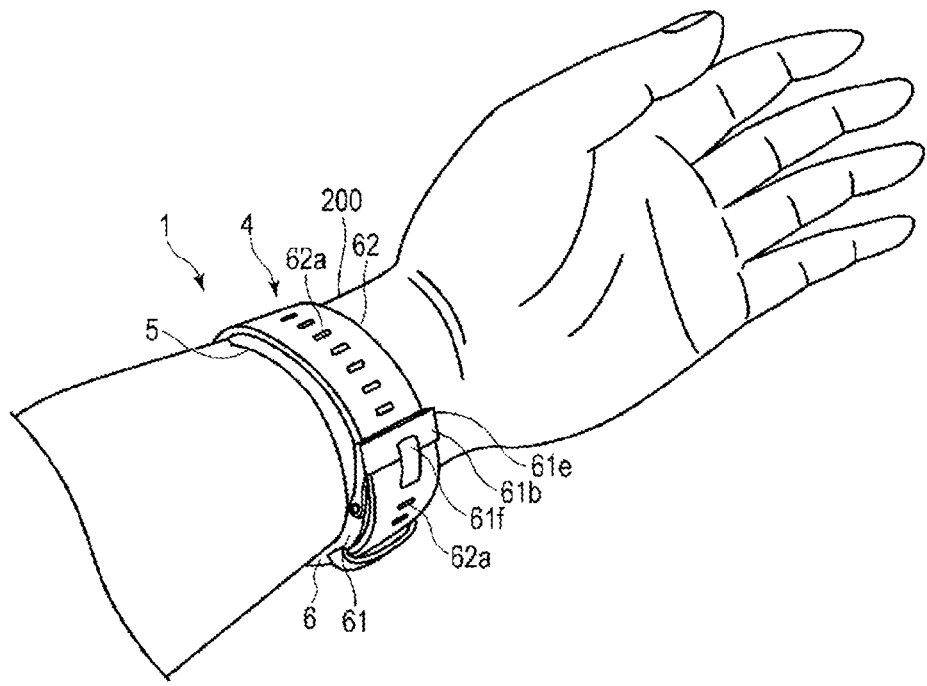

[Fig. 36]
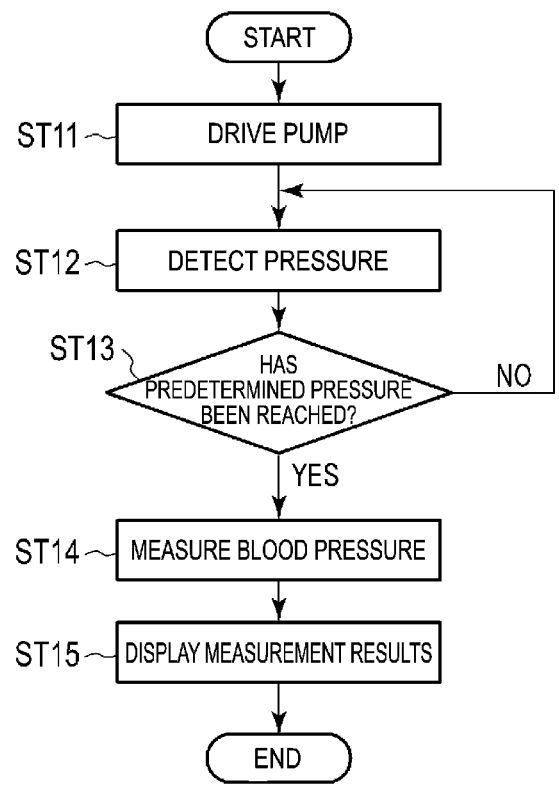

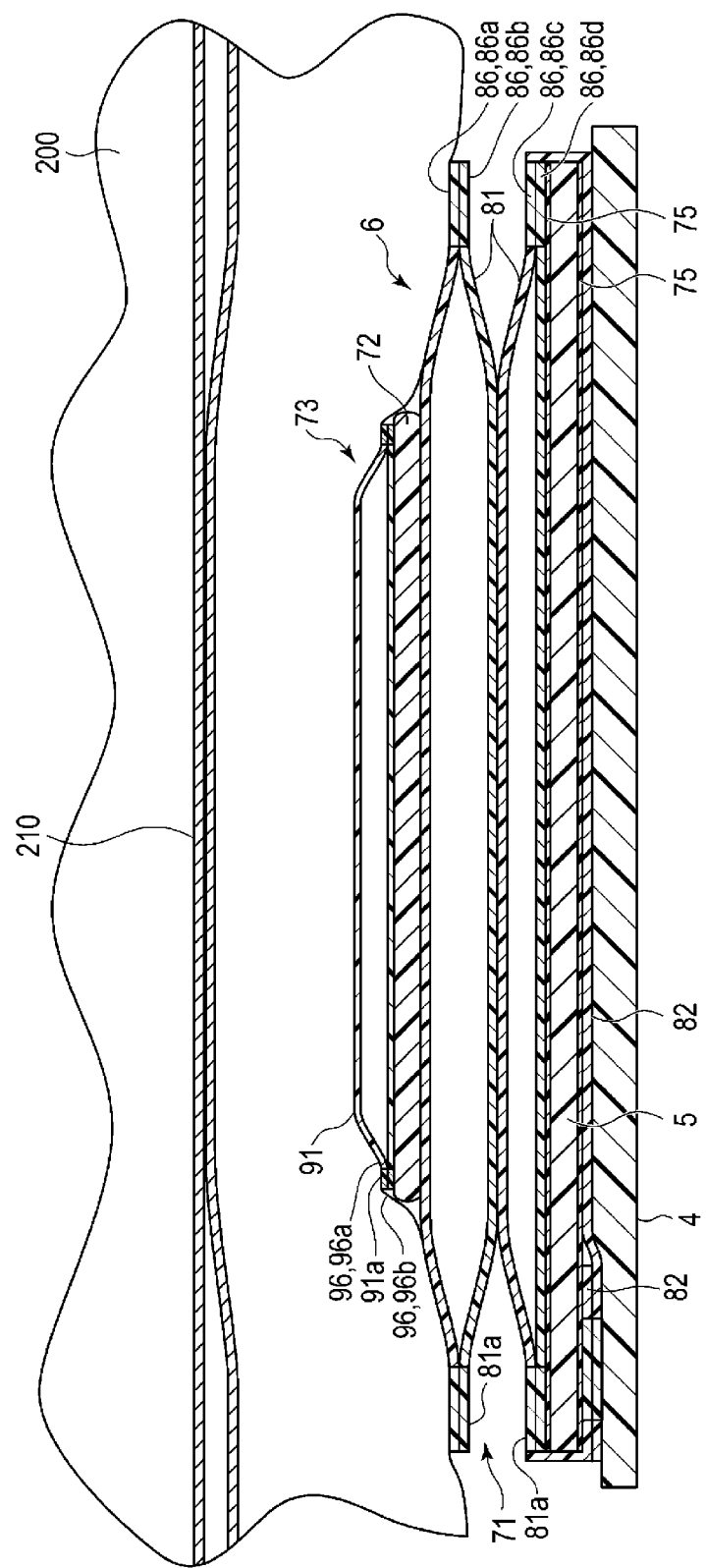

[Fig. 38]
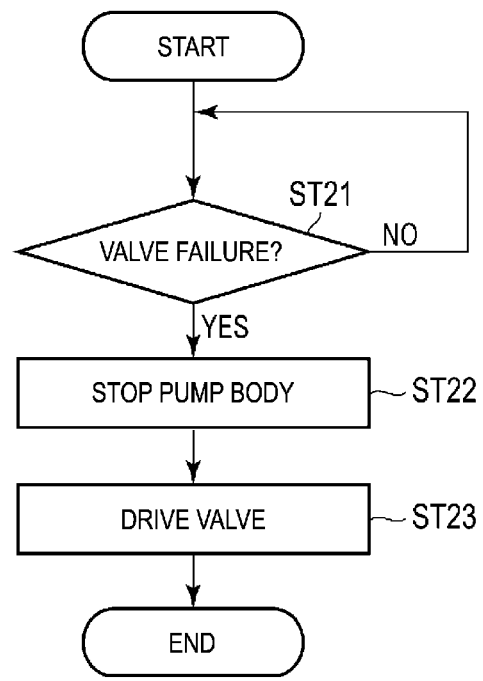

[Fig. 39]
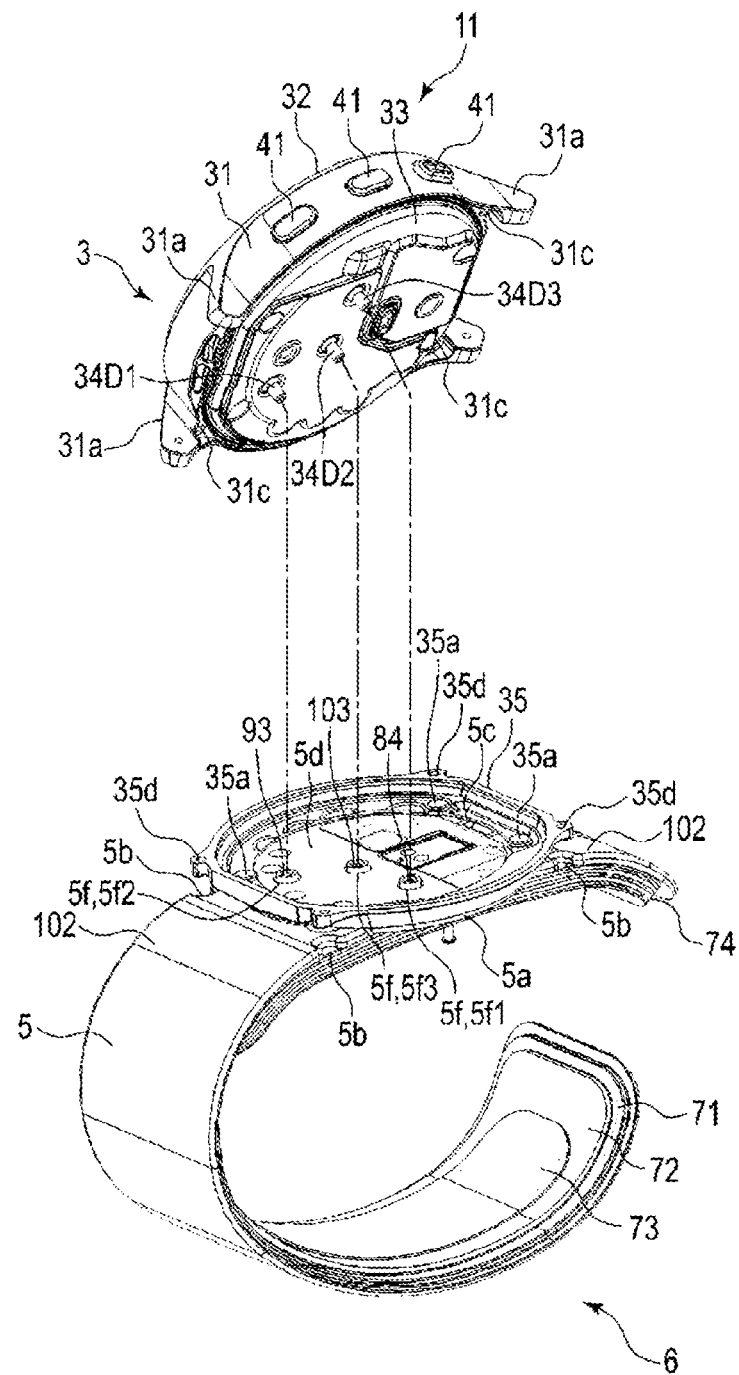

BLOOD PRESSURE MEASUREMENT DEVICE

CROSS-REFERENCE TO RELATED APPLICATIONS

This application is the U.S. national stage application filed pursuant to 35 U.S.C. 365 (c) and 120 as a continuation of International Patent Application No. PCT/JP2019/048035, filed Dec. 9, 2019, which application claims priority to Japan Patent Application No. 2018-246159, filed Dec. 27, 2018, which applications are incorporated herein by reference in their entireties.

TECHNICAL FIELD

The present invention relates to a blood pressure measurement device for measuring blood pressure.

BACKGROUND ART

In recent years, blood pressure measurement devices for measuring blood pressure are being used to monitor health status at home, as well as in medical facilities. A blood pressure measurement device detects vibration of the artery wall to measure blood pressure by, for example, inflating and contracting a cuff wrapped around the upper arm or the wrist of a living body and detecting the pressure of the cuff using a pressure sensor.

As such a blood pressure measurement device, for example, a so-called integral type is known in which a cuff is integrated with a device body supplying a fluid to the cuff. A known example of such a blood pressure measurement device such as the configuration described in JP 2005-230175 A (see Patent Document 1, for example) which includes a plurality of cuffs. Such a blood pressure measurement device provided with a plurality of cuffs may have a configuration that includes three cuffs, flow paths connecting the three cuffs and a pump, and four valves provided in the flow paths, wherein by opening and closing the four valves, the flow paths from the pump to each of the three cuffs are opened and closed.

CITATION LIST

Patent Literature

Patent Document 1: JP 2005-230175 A

SUMMARY OF INVENTION

Technical Problem

For the above-described blood pressure measurement device, wearable devices attached to the wrist have been proposed. For a blood pressure measurement device applied to a wearable device, as it can be expected to be used for blood pressure measurement at night time, there is a demand for a configuration in which air can be discharged from each of the three cuffs even in a case where one of the valves fails.

Thus, an object of the present invention is to provide a blood pressure measurement device capable of discharging a fluid from three cuffs even in a case where either one of a pump valve or an on-off valve fails.

Solution to Problem

According to an aspect, a blood pressure measurement device is provided which is attachable to a living body and includes, a cuff structure including a sensing cuff, a tensile cuff, and a pressing cuff that are configured to be inflated by a fluid, a pump including a pump body and a pump valve, a first flow path including a first on-off valve, the first flow path fluidly connecting the pump and the sensing cuff through the first on-off valve, a second flow path configured by branching from the first flow path between the pump and the first on-off valve, including a second on-off valve, a third on-off valve, and a fourth on-off valve, and connecting the pump and atmosphere through the second on-off valve, the third on-off valve, and the fourth on-off valve sequentially in that order, a third flow path configured by branching from the second flow path at an intermediate portion between the second on-off valve and the third on-off valve and fluidly connecting the pump and the tensile cuff, and a fourth flow path configured by branching from the second flow path at an intermediate portion between the third on-off valve and the fourth on-off valve and fluidly connecting the pump and the pressing cuff.

Here, the living body is the upper arm or the wrist, for example. The fluid includes a liquid and air. The cuff refers to a member that is wrapped around the upper arm, the wrist, or the like of a living body when the blood pressure is measured and that is inflated by being supplied with the fluid. The cuff includes a bag-like structure such as an air bag.

According to this aspect, even in a case where either one of the pump valve, the first on-off valve, the second on-off valve, the third on-off valve, or the fourth on-off valve is malfunctioning and cannot open, the sensing cuff, the tensile cuff, and the pressing cuff can be opened to the atmosphere through the pump valve or the fourth on-off valve. Thus, the air inside the sensing cuff, the tensile cuff, and the pressing cuff can be discharged through the pump valve or the fourth on-off valve.

In the blood pressure measurement device according to the one aspect described above, the blood pressure measurement device is provided that may further include a pressure sensor provided on the first flow path at an intermediate portion between the first on-off valve and the sensing cuff, a storage unit configured to store a threshold for pressure for determining failure of the pump valve, the first on-off valve, the second on-off valve, the third on-off valve, and the fourth on-off valve, and a control unit configured to determine failure of one of the pump valve, the first on-off valve, the second on-off valve, the third on-off valve, or the fourth on-off valve on the basis of a signal from the pressure sensor and the threshold, and open the other valves.

According to this aspect, even in a state where a user is unaware of an irregularity in the blood pressure measurement device such as night time, for example, the fluid of the internal space of the sensing cuff, the tensile cuff, and the pressing cuff are each discharged through the pump valve or the fourth on-off valve. In this manner, the safety of the blood pressure measurement device is improved.

In the blood pressure measurement device according to the one aspect described above, the blood pressure measurement device is provided that may further include a case including an outer case having a cylindrical shape and a windshield covering a first end of the outer case, a base portion installed with the pump, the first on-off valve, the second on-off valve, the third on-off valve, and the fourth on-off valve, the base portion being housed inside the case, a flow path plate fixed to the base portion on a living body side, the flow path plate constituting, with the base portion, a portion of the first flow path, a portion of the second flow path, a portion of the third flow path, and a portion of the fourth flow path, a first tube provided on the base portion on the windshield side, the first tube constituting another portion of the first flow path, and a second tube and a third tube provided on a surface of the base portion on the windshield side, the second tube and the third tube constituting another portion of the second flow path.

According to this aspect, by using the first tube, the second tube, and the third tube, the size of the flow path portion in the direction orthogonal to the axial direction of the outer case can be decreased.

In the blood pressure measurement device according to the one aspect described above, the blood pressure measurement device is provided in which the base portion and the flow path plate are fixed by adhesive, and the portion of the first flow path, the portion of the second flow path, the portion of the third flow path, and the portion of the fourth flow path each include a flow path groove formed in one of the base portion and the flow path plate and covered by the other one of the base portion and the flow path plate, and an escape portion for the adhesive, the escape portion is provided in a peripheral region of the flow path groove.

According to this aspect, the width of the flow path through which the fluid flow may be narrowed in each of the flow path portions. This allows the fluid to be efficiently supplied from the pump to the sensing cuff, the tensile cuff, and the pressing cuff. Furthermore, the adhesive, which is used to fix the flow path plate and the base portion, can be prevented from entering into the flow path grooves and blocking the flow path grooves.

In the blood pressure measurement device according to the one aspect described above, the blood pressure measurement device is provided that may further include a power supply unit fixed to a surface of the pump on the windshield side, wherein the first on-off valve, the second on-off valve, the third on-off valve, and the fourth on-off valve are disposed at positions separated from the pump in a direction orthogonal to an axial direction of the outer case.

According to this aspect, the case can be made thinner.

In the blood pressure measurement device according to one aspect described above, the blood pressure measurement device is provided in which the first on-off valve, the second on-off valve, the third on-off valve, and the fourth on-off valve are disposed along an inner surface of the outer case inside the case.

According to this aspect, space in the center region of the case can be effectively used. Thus, flexibility in the layout of the components of the blood pressure measurement device in the case can be improved.

Advantageous Effects of Invention

The present invention can provide a blood pressure measurement device capable of discharging a fluid from a sensing cuff, a pressing cuff, and a tensile cuff even in a case where either one of a pump valve or an on-off valve fails.

BRIEF DESCRIPTION OF DRAWINGS

FIG. 1 is a perspective view illustrating the configuration of a blood pressure measurement device according to an embodiment of the present invention.

FIG. 2 is an exploded perspective view illustrating the configuration of the blood pressure measurement device.

FIG. 3 is a side view illustrating the configuration of the blood pressure measurement device.

FIG. 4 is an explanatory diagram illustrating a state in which the blood pressure measurement device is attached to the wrist.

FIG. 5 is a block diagram illustrating the configuration of the blood pressure measurement device.

FIG. 6 is a block diagram illustrating the configuration of a flow path portion, an on-off valve, and a pressure sensor of the blood pressure measurement device.

FIG. 7 is a perspective view illustrating the configuration of the blood pressure measurement device.

FIG. 8 is an exploded perspective view illustrating the configuration of a device body of the blood pressure measurement device with a portion removed.

FIG. 9 is an exploded perspective view illustrating the configuration of the blood pressure measurement device with a portion removed.

FIG. 10 is a plan view illustrating a base portion and a flow path plate of the blood pressure measurement device.

FIG. 11 is a plan view illustrating the configuration of the base portion of the blood pressure measurement device.

FIG. 12 is a perspective view illustrating the configuration of the flow path plate of the blood pressure measurement device.

FIG. 13 is a plan view illustrating the configuration of the flow path plate of the blood pressure measurement device.

FIG. 14 is a plan view illustrating the configuration of the flow path plate of the blood pressure measurement device.

FIG. 15 is a perspective view of the flow path plate and a rear cover of the blood pressure measurement device in an exploded state.

FIG. 16 is a perspective view illustrating the configuration of the on-off valve, the pressure sensor, and a support plate of the blood pressure measurement device.

FIG. 17 is a plan view illustrating the configuration of the on-off valve, the pressure sensor, and a substrate of the blood pressure measurement device.

FIG. 18 is a cross-sectional view illustrating a main portion of the blood pressure measurement device.

FIG. 19 is a cross-sectional view illustrating a main portion of the blood pressure measurement device.

FIG. 20 is an exploded perspective view illustrating the configuration of a curler and a cuff structure of the blood pressure measurement device.

FIG. 21 is a cross-sectional view illustrating the configuration of the curler and the cuff structure of the blood pressure measurement device.

FIG. 22 is a cross-sectional view illustrating the configuration of the curler and the cuff structure of the blood pressure measurement device.

FIG. 23 is a cross-sectional view illustrating the configuration of a tensile cuff of the blood pressure measurement device.

FIG. 24 is a cross-sectional view illustrating the configuration of the tensile cuff of the blood pressure measurement device.

FIG. 25 is a perspective view illustrating the configuration of the curler of the blood pressure measurement device.

FIG. 26 is a plan view illustrating the configuration of the cuff structure of the blood pressure measurement device.

FIG. 27 is a plan view illustrating the configuration of the cuff structure.

FIG. 28 is a plan view illustrating the configuration of a palm-side cuff of the blood pressure measurement device.

FIG. 29 is a cross-sectional view illustrating the configuration of the palm-side cuff.

FIG. 30 is a plan view illustrating the configuration of a sensing cuff of the blood pressure measurement device.

FIG. 31 is a cross-sectional view illustrating the configuration of the sensing cuff of the blood pressure measurement device.

FIG. 32 is a flowchart illustrating an example of a method for manufacturing the blood pressure measurement device.

FIG. 33 is a perspective view illustrating an example in which the blood pressure measurement device is attached to the wrist.

FIG. 34 is a perspective view illustrating an example in which the blood pressure measurement device is attached to the wrist.

FIG. 35 is a perspective view illustrating an example in which the blood pressure measurement device is attached to the wrist.

FIG. 36 is a flowchart illustrating an example of the operations of the blood pressure measurement device.

FIG. 37 is a cross-sectional view schematically illustrating a state in which the blood pressure measurement device is attached to the wrist.

FIG. 38 is a flowchart illustrating an example of the operations of the blood pressure measurement device.

FIG. 39 is an exploded perspective view illustrating the configuration of the blood pressure measurement device.

DESCRIPTION OF EMBODIMENTS

An example of a blood pressure measurement device 1 according to an embodiment of the present invention is described below using FIGS. 1 to 38.

FIG. 1 is a perspective view illustrating a configuration of the blood pressure measurement device 1 according to a first embodiment of the present invention. FIG. 2 is an exploded perspective view illustrating the configuration of the blood pressure measurement device 1. FIG. 3 is a side view illustrating the configuration of the blood pressure measurement device 1. FIG. 4 is an explanatory diagram illustrating a state in which the blood pressure measurement device 1 is attached to the wrist 200. FIG. 5 is a block diagram illustrating the configuration of the blood pressure measurement device 1.

FIG. 6 is a block diagram illustrating the configuration of a flow path portion 15, an on-off valve 16, and a pressure sensor 17 of the blood pressure measurement device 1. FIG. 7 is a perspective view illustrating the configuration of the blood pressure measurement device 1. FIG. 8 is an exploded perspective view illustrating the configuration of a device body 3 of the blood pressure measurement device 1 with a portion removed. FIG. 9 is an exploded perspective view illustrating the configuration of the blood pressure measurement device 1 with a portion removed.

FIG. 10 is a plan view illustrating a base portion 33 and a flow path plate 34 of the blood pressure measurement device 1 in a state as seen from the wrist 200 side. FIG. 11 is a plan view of the base portion 33 of the blood pressure measurement device 1 in a state as seen from the flow path plate 34 side. FIG. 12 is a perspective view illustrating the flow path plate 34 of the blood pressure measurement device 1. FIG. 13 is a plan view illustrating the flow path plate 34 of the blood pressure measurement device 1 in a state as seen from a windshield 32 side. FIG. 14 is a plan view illustrating the flow path plate 34 of the blood pressure measurement device 1 in a state as seen from the wrist 200 side.

FIG. 15 is a perspective view of the flow path plate 34 and a rear cover 35 of the blood pressure measurement device 1 in an exploded state. FIG. 16 is a perspective view illustrating the configuration of the on-off valve 16, the pressure sensor 17, and a support plate 38 of the blood pressure measurement device 1. FIG. 17 is a plan view illustrating the configuration of the on-off valve 16, the pressure sensor 17, and the support plate 38 of the blood pressure measurement device 1 in a state as seen from the wrist 200 side.

FIG. 18 is a cross-sectional view illustrating the configuration of the base portion 33 and the flow path plate 34 of the blood pressure measurement device 1. FIG. 19 is a cross-sectional view illustrating the configuration of the base portion 33 and the flow path plate 34 of the blood pressure measurement device 1. FIG. 20 is a perspective view illustrating the configuration of a curler 5 and a cuff structure 6 of the blood pressure measurement device 1.

FIG. 21 is a cross-sectional view illustrating the configuration of the curler 5 and the cuff structure 6 of the blood pressure measurement device 1. FIG. 22 is a cross-sectional view illustrating the configuration of the curler 5 and the cuff structure 6 of the blood pressure measurement device 1. FIG. 23 is a cross-sectional view illustrating the configuration of a tensile cuff 74 of the blood pressure measurement device 1.

FIG. 24 is a cross-sectional view illustrating the configuration of the tensile cuff 74 of the blood pressure measurement device 1. FIG. 25 is a perspective view illustrating the configuration of the curler 5 of the blood pressure measurement device 1. FIG. 26 is a plan view illustrating a configuration of the cuff structure 6 of the blood pressure measurement device 1 on the wrist 200 side. FIG. 27 is a plan view illustrating the cuff structure 6 in a state as seen from the inner circumferential surface side of the curler 5. FIG. 28 is a plan view illustrating the configuration of a pressing cuff 71 of the blood pressure measurement device 1. FIG. 29 is a cross-sectional view illustrating the configuration of the pressing cuff 71, which is a line cross-section along XXIX-XXIX illustrated in FIG. 28. FIG. 30 is a plan view illustrating the configuration of a sensing cuff 73 of the blood pressure measurement device 1. FIG. 31 is a cross-sectional view illustrating the configuration of the sensing cuff 73 of the blood pressure measurement device 1, which is a line cross-section along XXXI-XXXI illustrated in FIG. 30.

FIG. 31 is a cross-sectional view illustrating the configuration of the sensing cuff 73 of the blood pressure measurement device 1. FIG. 32 is a flowchart illustrating an example of a method for manufacturing the blood pressure measurement device 1. FIGS. 33 to 35 are perspective views illustrating an example in which the blood pressure measurement device 1 is attached to the wrist 200. FIG. 36 is a flowchart illustrating an example of the operations of the blood pressure measurement device 1. FIG. 37 is a cross-sectional view schematically illustrating a state in which the blood pressure measurement device 1 is attached to the wrist 200. FIG. 38 is a flowchart illustrating an example of the operations of the blood pressure measurement device 1. FIG. 39 is an exploded perspective view illustrating the configuration of the blood pressure measurement device 1.

The blood pressure measurement device 1 is an electronic blood pressure measurement device attached to a living body. The present embodiment will be described using an electronic blood pressure measurement device having an aspect of a wearable device attached to the wrist 200 of the living body.

As illustrated in FIGS. 1 to 3 and FIG. 5, the blood pressure measurement device 1 includes the device body 3, a belt 4 that fixes the device body 3 at the wrist, the curler 5 disposed between the belt 4 and the wrist, the cuff structure 6 including the pressing cuff 71, the sensing cuff 73, and the tensile cuff 74, a fluid circuit 7 fluidly connecting the device body 3 and the cuff structure 6, and a power feeding unit 8 provided on the curler 5.

As illustrated in FIGS. 1 to 5, the device body 3 includes, for example, a case 11, a display unit 12, an operation unit 13, a pump 14, the flow path portion 15, the on-off valve 16, the pressure sensor 17, a power supply unit 18, a vibration motor 19, and a control substrate 20. The device body 3 supplies a fluid to the cuff structure 6 using the pump 14, the on-off valve 16, the pressure sensor 17, the control substrate 20, and the like.

As illustrated in FIGS. 1 to 3 and FIGS. 8 to 14, the case 11 includes an outer case 31, the windshield 32 covering an opening of the outer case 31 on the opposite side (outer side) to the wrist 200, the base portion 33 provided inside the outer case 31 on the wrist 200 side, the flow path plate 34 fixed on a surface of the base portion 33 on the wrist 200 side, the rear cover 35 covering the wrist 200 side of the outer case 31, and a sealing member 36 provided on the lower surface of the rear cover 35.

As illustrated in FIGS. 4 and 8, the outer case 31 is formed in a cylindrical shape. The outer case 31 includes pairs of lugs 31a provided at respective symmetrical positions in the circumferential direction of an outer circumferential surface, and spring rods 31b each provided between each of the two pairs of lugs 31a.

Also, as illustrated in FIG. 9, in the outer case 31, a hole 31c is formed between a first pair of lugs 31a and between a second pair of lugs 31a. The holes 31c communicate from the inside of the outer case 31 to the outside. A filter 37 is provided at an opening end of the hole 31c disposed on the inner circumferential surface of the outer case 31. The filter 37 functions so as to allow air to pass through but to restrict the passage of water. Here, "restrict" refers to limiting the amount of water passed through. The filter 37 is preferably capable of preventing the passage of water.

As illustrated in FIG. 8, in the outer case 31, the filter 37 is provided at the inner circumferential surface of the portion between the first pair of lugs 31a and at the inner circumferential surface of the portion between the second pair of lugs 31a. Also, in the outer case 31, the inner circumferential surface of the portion between the first pair of lugs 31a and the inner circumferential surface of the portion between the second pair of lugs 31a are parallel with one another and are configured as flat surfaces parallel with an axial direction D of the outer case 31. The inner circumferential surface of the portion between both pairs of lugs 31a is configured as a curved surface. The windshield 32 is, for example, a circular glass plate.

The base portion 33 is configured to have a planar shape that is substantially similar to the shape of the opening of the outer case 31. The base portion 33 holds the display unit 12, the operation unit 13, the pump 14, the on-off valve 16, the pressure sensor 17, the power supply unit 18, the vibration motor 19, and the control substrate 20. Additionally, the base portion 33 constitutes a portion of the flow path portion 15 that makes the pump 14 and the cuff structure 6 fluidly continuous.

A recess 33b where the control substrate 20 is disposed is formed in a surface 33a of the base portion 33 on the windshield 32 side, at the side where the first pair of lugs 31a are located. The region, opposite the recess 33b, of a surface 33c of the base portion 33 on the rear cover 35 side is configured as a protrusion portion 33d projecting to the rear cover 35 side.

A first hole 33A1 in which a portion of a first on-off valve 16A described below is disposed, a second hole 33A2 in which a portion of a second on-off valve 16B described below is disposed, a third hole 33A3 in which a portion of a third on-off valve 16C described below is disposed, and a fourth hole 33A4 in which a portion of a fourth on-off valve 16D described below is disposed are formed in the base portion 33.

Also, a fifth hole 33A5 in which a portion of a first pressure sensor 17A described below is disposed and a sixth hole 33A6 in which a portion of a second pressure sensor 17B described below is disposed are formed in the base portion 33.

The first hole 33A1, the second hole 33A2, the third hole 33A3, the fourth hole 33A4, the fifth hole 33A5, and the sixth hole 33A6 are disposed in a region of the base portion 33 surrounded by an edge, which is configured in an arc shape, facing the inner circumferential surface of the portion of the outer case 31 between the first pair of lugs 31a and the second pair of lugs 31a.

The holes are disposed side by side in order of the fifth hole 33A5, the sixth hole 33A6, the first hole 33A1, the second hole 33A2, the third hole 33A3, and the fourth hole 33A4 in a direction from the first pair of lugs 31a side toward the second pair of lugs 31a side.

Also, a seventh hole 33A7 that is fluidly connected to an ejection hole 14d of the pump 14 is formed in the base portion 33. The seventh hole 33A7 is disposed, for example, at a position facing the ejection hole 14d in the thickness direction of the base portion 33.

As illustrated in FIG. 11, an annular groove 33B is formed in a portion of the surface 33c of the base portion 33 on the rear cover 35 side facing the peripheral edge portion of the flow path plate 34. A portion of the groove 33B is disposed in a portion of the edge of the protrusion portion 33d.

The flow path plate 34 covers a portion of the region of the surface 33c of the base portion 33 on the wrist 200 side excluding the protrusion portion 33d. A first recess 34A1 facing the first hole 33A1, a second recess 34A2 facing the second hole 33A2, a third recess 34A3 facing the third hole 33A3, a fourth recess 34A4 facing the fourth hole 33A4, a fifth recess 34A5 facing the fifth hole 33A5, and a sixth recess 34A6 facing the sixth hole 33A6 are formed in a surface 34a of the flow path plate 34 on the base portion 33 side.

The recesses are disposed side by side in order of the fifth recess 34A5, the sixth recess 34A6, the first recess 34A1, the second recess 34A2, and the fourth recess 34A4 in a direction from the first pair of lugs 31a side toward the second pair of lugs 31a side.

As illustrated in FIG. 14, the portion of a surface 34b of the flow path plate 34 on the wrist 200 side facing the rear cover 35 includes a first projection portion 34B1, a second projection portion 34B2, a third projection portion 34B3, and a fourth projection portion 34B4.

As illustrated in FIG. 2, the rear cover 35 is configured as an annular shape with an open center. The rear cover 35 covers the end portion on the outer peripheral edge side of the outer case 31 on the wrist 200 side.

Also, as illustrated in FIGS. 2 and 15, a first recess 35e1 that engages with the first projection portion 34B1, a second recess 35e2 that engages with the second projection portion 34B2, a third recess 35e3 that engages with the third projection portion 34B3, and a fourth recess 35e4 that engages with the fourth projection portion 34B4 are formed in the surface of the rear cover 35 on the flow path plate 34 side.

With the rear cover 35 configured as such being integrally assembled with the curler 5, the central opening is covered by the curler 5, and the rear cover 35 together with the curler 5 forms a rear lid covering the end portion of the outer case 31 on the wrist 200 side. Specifically, the rear cover 35 is fixed to the curler 5 with four first joining members 35a and fixed to the end portion of the outer case 31 on the wrist 200 side with four second joining members 35b. The rear cover 35 includes four hole portions 35c into which the first joining members 35a that are provided at the bottom portion and fixed to the curler 5 are inserted, and four hole portions 35d provided at four portions of the outer circumferential portion that radially project out, into which the second joining members 35b that are fixed to the outer case 31 are inserted.

The first joining members 35a and the second joining members 35b are members, such as a screw, a bolt, a machine screw, a rive, for mechanically joining two components. In the present embodiment, the first joining members 35a and the second joining members 35b are screws.

The sealing member 36 is a double-sided tape, for example, formed in the shape of the region of the rear cover 35 that comes into contact with the curler 5. The sealing member 36 seals between the curler 5 and the rear cover 35 by being provided between the curler 5 and the rear cover 35.

The display unit 12 is disposed on the base portion 33 of the outer case 31 and directly below the windshield 32. As illustrated in FIG. 5, the display unit 12 is electrically connected to the control substrate 20. The display unit 12 is, for example, a liquid crystal display or an organic electroluminescence display. The display unit 12 displays various types of information including the date and time and measurement results of blood pressure values such as the systolic blood pressure and diastolic blood pressure, heart rate, and the like.

The operation unit 13 is configured to be capable of receiving an instruction input from a user. For example, the operation unit 13 includes a plurality of buttons 41 provided on the case 11, a sensor 42 that detects operation of the buttons 41, and a touch panel 43 provided on the display unit 12 or the windshield 32, as illustrated in FIGS. 1 and 5. When operated by the user, the operation unit 13 converts an instruction into an electrical signal. The sensor 42 and the touch panel 43 are electrically connected to the control substrate 20 to output electrical signals to the control substrate 20.

As the plurality of buttons 41, for example, three buttons are provided. The buttons 41 are supported by the base portion 33 and protrude from the outer circumferential surface of the outer case 31. The plurality of buttons 41, specifically, project from a portion of the portion between the first pair of lugs 31a and the second pair of lugs 31a on the outer circumferential surface of the outer case 31 on the side opposite across the center of the outer case 31 to the first on-off valve 16A, the second on-off valve 16B, the third on-off valve 16C, the fourth on-off valve 16D, the first pressure sensor 17A, and the second pressure sensor 17B. The plurality of buttons 41 and a plurality of the sensors 42 are supported by the base portion 33. The touch panel 43 is integrally provided on the windshield 32, for example.

As illustrated in FIG. 8, the pump 14 is, for example, a piezoelectric pump. The pump 14 compresses air and supplies compressed air to the cuff structure 6 through the flow path portion 15. The pump 14 is electrically connected to the control substrate 20.

As illustrated in FIG. 6, the pump 14 includes a pump body 14a and a pump valve 14b. The pump body 14a compresses air and ejects the air to the flow path portion 15. The pump valve 14b is configured to be capable to discharge air from the pump body 14a and air from the flow path portion 15 to the atmosphere by being opened.

The pump 14 is fixed at a position separated from the first on-off valve 16A, the second on-off valve 16B, the third on-off valve 16C, the first pressure sensor 17A, and the second pressure sensor 17B in the direction orthogonal to the axial direction D of the outer case 31.

Herein, in relation to the position of the pump 14 inside the outer case 31 will be described using, a direction parallel with the direction from the first pair of lugs 31a toward the second pair of lugs 31a is defined as a first direction, and a direction orthogonal to both the first direction and the axial direction D of the outer case 31 is defined as a second direction. For example, the pump 14 is disposed at a position next to the recess 33b in the first direction in a central region of the outer case 31 in the second direction in respect to the first on-off valve 16A, the second on-off valve 16B, the third on-off valve 16C, the fourth on-off valve 16D, the first pressure sensor 17A, and the second pressure sensor 17B. The pump 14 is fixed to the base portion 33 with double-sided tape, for example. The ejection hole 14d is disposed on the surface of the pump 14 on the base portion 33 side.

The flow path portion 15 constitutes a portion of the flow path connecting from the pump 14 to the pressing cuff 71 and the tensile cuff 74 and a portion of the flow path connecting from the pump 14 to the sensing cuff 73, as illustrated in FIG. 5. Additionally, the flow path portion 15 constitutes a portion of the flow path connecting from the pressing cuff 71 and the tensile cuff 74 to the atmosphere, and a portion of the flow path connecting from the sensing cuff 73 to the atmosphere. The flow path portion 15 is a flow path for air constituted by a hollow portion, a groove, and a flow path portion provided between the base portion 33 and the flow path plate 34 as well as a tube provided on the base portion 33 and the like.

As illustrated in FIG. 9, the flow path portion 15 specifically includes a flow path portion body 15a, a first tube 15b, a second tube 15c, and a third tube 15d. The flow path portion 15 is constituted by attaching the first tube 15b, the second tube 15c, and the third tube 15d to the flow path portion body 15a.

The flow path portion body 15a is constituted between the base portion 33 and the flow path plate 34. The flow path portion body 15a includes a first flow path portion 141, a second flow path portion 142, a third flow path portion 143, and a fourth flow path portion 144.

The first flow path portion 141 constitutes the flow path successive through the first hole 33A1, the second hole 33A2, and the seventh hole 33A7. As illustrated in FIGS. 11 to 13, the first flow path portion 141 is a chamber, which is constituted by a base portion side first structure portion 141a which is a portion of the surface 33c of the base portion 33 on the wrist 200 side and a flow path plate side first structure portion 141b which is a portion of the surface 34a of the flow path plate 34 on the base portion 33 side, including a first flow path groove 141c and an escape portion for adhesive.

As illustrated in FIG. 11, the base portion side first structure portion 141a includes the first hole 33A1, the second hole 33A2, and the seventh hole 33A7. The base portion side first structure portion 141a extends in the second direction from the first hole 33A1 and the second hole 33A2 to a center region of the base portion 33, and extends in the first direction from the center region to an end on the first pair of lugs 31a side.

Also, a first dividing groove 33C1 and a second dividing groove 33C2 that divide, together with the groove 33B, the base portion side first structure portion 141a from other portions are formed at the edge of the base portion side first structure portion 141a. Both ends of the first dividing groove 33C1 are formed in a shape that communicates with the groove 33B. Both ends of the second dividing groove 33C2 are formed in a shape that communicates with the groove 33B.

As illustrated in FIGS. 12 and 13, the flow path plate side first structure portion 141b is constituted by the region facing the base portion side first structure portion 141a. Specifically, the flow path plate side first structure portion 141b extends from the edge portion of the flow path plate 34 on which the first recess 34A1 and the second recess 34A2 is disposed to the center region of the outer case 31 in the second direction, then extends in the first direction to the edge portion of the flow path plate 34 on the first pair of lugs 31a side.

A seventh recess 34A7 is formed in the flow path plate side first structure portion 141b at the portion facing the seventh hole 33A7. In addition, in the flow path plate side first structure portion 141b, the first flow path groove 141c that communicates through the first recess 34A1, the second recess 34A2, and the seventh recess 34A7 is formed.

At the edge of the flow path plate side first structure portion 141b, an annular third dividing groove 34C3 that divides the flow path plate side first structure portion 141b from other portions is formed. The third dividing groove 34C3 faces the groove 33B, the first dividing groove 33C1, and the second dividing groove 33C2 of the base portion 33, as illustrated by a two-dot chain line in FIG. 11.

The flow path plate side first structure portion 141b is configured in a planar shape. In addition, as illustrated in FIGS. 18 and 19, the flow path plate side first structure portion 141b is configured as a low surface relative to the portion adjacent to the third dividing groove 34C3 on the outer side of the third dividing groove 34C3. Note that herein, "low" is based on a case where the blood pressure measurement device 1 is orientated with the axial direction D of the outer case 31 being parallel with the direction of gravitational force and the display unit 12 is disposed above the rear cover 35. Here in after. in a case where height is described, this is also based on a case where the blood pressure measurement device 1 is orientated with the axial direction D of the outer case 31 being parallel with the direction of gravitational force and the display unit 12 is disposed above the rear cover 35.

The flow path of the first flow path portion 141 with such a configuration is constituted by the first flow path groove 141c being covered by the base portion side first structure portion 141a. In addition, in the peripheral region of the first flow path groove 141c, a gap between the base portion side first structure portion 141a and the flow path plate side first structure portion 141b is provided, constituting an escape portion 141d of adhesive G for fixing the flow path plate 34 and the base portion 33. The gap is very small, for example.

As illustrated in FIG. 6, the second flow path portion 142 is connected to the first flow path portion 141 through the first on-off valve 16A and the first tube 15b. The second flow path portion 142 constitutes a portion of the flow path from the pump 14 to the sensing cuff 73. A portion of the peripheral region of the second flow path portion 142 is surrounded by the first flow path portion 141, and the other portion of the peripheral region is surrounded by an edge portion of the base portion 33 and an edge portion of the flow path plate 34.

As illustrated in FIGS. 11 and 12, the second flow path portion 142 is a chamber, which is constituted by a base portion side second structure portion 142a that is a portion of the surface 33c of the base portion 33 on the wrist 200 side, and a flow path plate side second structure portion 142b that is a portion of the surface 34a of the flow path plate 34 on the base portion 33 side, including a second flow path groove 142c and an escape portion for adhesive.

As illustrated in FIG. 11, the base portion side second structure portion 142a is constituted by the region surrounded by the base portion side first structure portion 141a and an edge portion of the base portion 33. The fifth hole 33A5 and the sixth hole 33A6 are disposed in the base portion side second structure portion 142a.

An eighth hole 33A8 is formed in the base portion side second structure portion 142a at a center position of the outer case 31 in the second direction with respect to the sixth hole 33A6. The eighth hole 33A8 is fluidly connected to the first tube 15b.

The base portion side second structure portion 142a with such a configuration is divided from the base portion side first structure portion 141a by the groove 33B and the second dividing groove 33C2. Furthermore, the base portion side second structure portion 142a is configured in a planar shape.

As illustrated in FIG. 12, the flow path plate side second structure portion 142b faces the base portion side second structure portion 142a. The flow path plate side second structure portion 142b is surrounded by the flow path plate side first structure portion 141b and an edge portion of the flow path plate 34.

In addition, a ninth hole 34A9 fluidly connected to the sensing cuff 73 is formed in the flow path plate side second structure portion 142b in the center region of the outer case 31 in the second direction with respect to the fifth recess 34A5 and the sixth recess 34A6. As illustrated in FIGS. 14 and 15, a first nozzle 34D1, in which the ninth hole 34A9 is disposed inside, is formed on the surface of the flow path plate 34 on the wrist 200 side.

The first nozzle 34D1 is fluidly connected to a connection portion 93, described below, of the sensing cuff 73 as illustrated in FIGS. 6 and 39. In addition, in the flow path plate side second structure portion 142b, the second flow path groove 142c that communicates through the fifth recess 34A5, the sixth recess 34A6, and the ninth recess 34A9 is formed. The second flow path groove 142c faces the eighth hole 33A8 of the base portion 33. Additionally, the width of the second flow path groove 142c is less than the width of the flow path plate side second structure portion 142b.

Also, an annular fourth dividing groove 34C4 is formed at the edge of the flow path plate side second structure portion 142b. The fourth dividing groove 34C4 divides the flow path plate side second structure portion 142b from the other portions. The fourth dividing groove 34C4 faces the groove 33B and the second dividing groove 33C2 of the base portion 33, as illustrated by a two-dot chain line in FIG. 11.

The flow path plate side second structure portion 142b is configured in a planar shape. In addition, the flow path plate side second structure portion 142b is configured as a low surface relative to the portion adjacent to the fourth dividing groove 34C4 on the outer side of the fourth dividing groove 34C4.

The flow path of the second flow path portion 142 with such a configuration is constituted by the second flow path groove 142c being covered by the base portion side second structure portion 142a. In addition, in the peripheral region of the second flow path groove 142c, a gap between the base portion side second structure portion 142a and the flow path plate side second structure portion 142b is provided, constituting an escape portion 142d of the adhesive G for fixing the base portion 33 and the flow path plate 34. The gap is a very small gap, for example.

The third flow path portion 143 constitutes a portion of the flow path from the pump 14 to the tensile cuff 74, as illustrated in FIG. 6. The third flow path portion 143 is fluidly connected to the first flow path portion 141 through the second on-off valve 16B and the second tube 15c. The third flow path portion 143 is fluidly connected to the fourth flow path portion 144 through the third on-off valve 16C and the third tube 15d.

As illustrated in FIG. 11, the third flow path portion 143 is a chamber, which is constituted by a base portion side third structure portion 143a that is a portion of the surface 33c of the base portion 33 on the wrist 200 side and a flow path plate side third structure portion 143b that is a portion of the surface 34a of the flow path plate 34 on the base portion 33 side, including a third flow path groove 143c and an escape portion for adhesive.

As illustrated in FIG. 11, the base portion side third structure portion 143a is adjacent in the first direction to the first dividing groove 33C1 of the base portion side first structure portion 141a. The base portion side third structure portion 143a extends from the third hole 33A3 side to the center region of the outer case 31 in the second direction.

A tenth hole 33A10 fluidly connected to the second tube 15c is formed in the base portion side third structure portion 143a.

The base portion side third structure portion 143a is configured in a planar shape. Also, a fifth dividing groove 33C5 that divides, together with the groove 33B and the first dividing groove 33C1, the base portion side third structure portion 143a from other portions is formed at the edge of the base portion side third structure portion 143a.

As illustrated in FIGS. 12 and 13, the flow path plate side third structure portion 143b faces the base portion side third structure portion 143a. The flow path plate side third structure portion 143b extends from the third recess 34A3 to the center region of the outer case 31 in the second direction.

An eleventh hole 34A11 fluidly connected to the tensile cuff 74 is formed in the flow path plate side third structure portion 143b on the side of the other end side from the third recess 34A3. As illustrated in FIGS. 14 and 15, a second nozzle 34D2, in which the eleventh hole 34A11 is disposed inside, is formed on the surface 34b of the flow path plate 34 on the wrist 200 side. The second nozzle 34D2 is fluidly connected to a connection portion 103, described below, of the tensile cuff 74 as illustrated in FIGS. 6 and 39.

In addition, in the flow path plate side third structure portion 143b, the third flow path groove 143c that communicates through the third recess 34A3 and the eleventh hole 34A11 is formed. The third flow path groove 143c faces and communicates with the tenth hole 33A10 of the base portion side third structure portion 143a. The width of the third flow path groove 143c is less than the width of the flow path plate side third structure portion 143b.

An annular sixth dividing groove 34C6 is formed at the edge of the flow path plate side third structure portion 143b. The sixth dividing groove 34C6 faces the groove 33B, the first dividing groove 33C1, and the fifth dividing groove 33C5 of the base portion 33, as illustrated by a two-dot chain line in FIG. 11. The sixth dividing groove 34C6 divides the flow path plate side third structure portion 143b from the other portions.

The flow path plate side third structure portion 143b is configured in a planar shape. In addition, the flow path plate side third structure portion 143b is configured as a low surface relative to the portion adjacent to the sixth dividing groove 34C6 on the outer side of the sixth dividing groove 34C6.

The flow path of the third flow path portion 143 with such a configuration is constituted by the third flow path groove 143c being covered by the base portion side third structure portion 143a. In addition, in the peripheral region of the third flow path groove 143c, a gap between the base portion side third structure portion 143a and the flow path plate side third structure portion 143b is provided, constituting an escape portion 143d of adhesive for fixing the base portion 33 and the flow path plate 34. The gap is a very small gap, for example.

The fourth flow path portion 144 constitutes a portion of the flow path from the third flow path portion 143 to the pressing cuff, as illustrated in FIG. 6. The fourth flow path portion 144 is fluidly connected to the third flow path portion 143 through the third on-off valve 16C and the third tube 15d.

As illustrated in FIGS. 9 to 12, the fourth flow path portion 144 is a chamber, which is constituted by a base portion side fourth structure portion 144a that is a portion of the surface 33c of the base portion 33 on the wrist 200 side and a flow path plate side fourth structure portion 144b that is a portion of the surface 34a of the flow path plate 34 on the base portion 33 side, including a fourth flow path groove 144c and an escape portion for adhesive.

As illustrated in FIG. 11, the base portion side fourth structure portion 144a is disposed at a position next to the fifth dividing groove 33C5 of the base portion side third structure portion 143a in the first direction. The base portion side fourth structure portion 144a extends from the fourth hole 33A4 side to a center region of the outer case 31 in the second direction, passing through a portion of the edge of the protrusion portion 33d, then extends to the edge portion of the base portion 33 in the first direction, passing through a side of the base portion side third structure portion 143a and the base portion side first structure portion 141a.

A twelfth hole 33A12 is formed near the fourth hole 33A4. The twelfth hole 33A12 is fluidly connected to the third tube 15d. The base portion side fourth structure portion 144a is divided from other portions by the groove 33B and the fifth dividing groove 33C5. Furthermore, the base portion side fourth structure portion 144a is configured in a planar shape.

As illustrated in FIGS. 12 and 13, the flow path plate side fourth structure portion 144b faces the base portion side fourth structure portion 144a. The flow path plate side fourth structure portion 144b extends in the second direction from the fourth recess 34A4 side to a center region of the outer case 31, then extends to an end of the flow path plate 34 in the first direction.

A thirteenth recess 34A13 is formed in the flow path plate side fourth structure portion 144b at the portion facing the twelfth hole 33A12.

A fourteenth hole 34A14 fluidly connected to the pressing cuff 71 is formed in the flow path plate side fourth structure portion 144b in the center region of the outer case 31 in the second direction. As illustrated in FIGS. 14 and 15, a third nozzle 34D3, in which the fourteenth hole 34A14 is disposed inside, is formed on the surface 34b of the flow path plate 34 on the wrist 200 side. The third nozzle 34D3 is inserted inside a third hole portion 5f3, described below, of a cover portion 5a of the curler 5 and is fluidly connected to a connection portion 84 of the pressing cuff 71 as illustrated in FIGS. 6 and 39.

In the flow path plate side fourth structure portion 144b, the fourth flow path groove 144c that communicates through the fourth recess 34A4, the thirteenth recess 34A13, and the fourteenth hole 34A14 is formed. An annular seventh dividing groove 34C7 is formed at the edge of the flow path plate side fourth structure portion 144b. The seventh dividing groove 34C7 faces the groove 33B, the second dividing groove 33C2, and the fifth dividing groove 33C5 of the base portion 33, as illustrated by a two-dot chain line in FIG. 11.

The flow path plate side fourth structure portion 144b is configured in a planar shape. In addition, the flow path plate side fourth structure portion 144b is configured as a low surface relative to the portion continuous with the seventh dividing groove 34C7 on the outer side of the seventh dividing groove 34C7.

The flow path of the fourth flow path portion 144 with such a configuration is constituted by the fourth flow path groove 144c being covered by the base portion side fourth structure portion 144a. In addition, in the peripheral region of the fourth flow path groove 144c, a gap between the base portion side fourth structure portion 144a and the flow path plate side fourth structure portion 144b is provided, constituting an escape portion 144d of adhesive for fixing the base portion 33 and the flow path plate 34.

The base portion 33 and the flow path plate 34 with such a configuration are fixed with the adhesive G as illustrated in FIGS. 18 and 19. Specifically, the adhesive G is disposed between the groove 33B and the plurality of dividing grooves 33C1, 33C2 and 33C5 formed in the base portion 33 and the plurality of dividing grooves 34C3, 34C4, 34C6 and 34C7 formed in the flow path plate 34 facing the groove 33B and the plurality of dividing grooves 33C1, 33C2 and 33C5.

Also, as illustrated in FIG. 19 with the first dividing groove 33C1, the third dividing groove 34C3, and the sixth dividing groove 34C6 illustrated as representatives, the regions of the surface 34a of the flow path plate 34 between adjacent pairs of dividing grooves face dividing grooves formed in the base portion 33. Adjacent pairs of dividing grooves of the surface 34a of the flow path plate 34 are continuous with the dividing grooves formed in the base portion 33 in between.

The adhesive G disposed in the groove 33B formed in the base portion 33 and the plurality of dividing grooves 33C1, 33C2 and 33C5 and the dividing grooves 34C3, 34C4, 34C6 and 34C7 formed in the flow path plate 34 provides the first flow path portion 141, the second flow path portion 142, the third flow path portion 143, and the fourth flow path portion 144 with a fluid seal.

Note that by disposing the adhesive G in the groove 33B and the dividing grooves 33C1, 33C2 and 33C5 of the base portion 33 and the dividing grooves 34C3, 34C4, 34C6 and 34C7 of the flow path plate 34, the adhesive G becomes a wall portion disposed between the base portion 33 and the flow path plate 34. As a result, a gap is generated between the base portion side first structure portion 141a and the flow path plate side first structure portion 141b. Similarly, gaps are formed between the base portion side second structure portion 142a and the flow path plate side second structure portion 142b, between the base portion side third structure portion 143a and the flow path plate side third structure portion 143b, and between the base portion side fourth structure portion 144a and the flow path plate side fourth structure portion 144b.

As illustrated in FIG. 6, the first tube 15b is connected to the first on-off valve 16A and the second flow path groove 142c of the second flow path portion 142 and fluidly connects the first on-off valve 16A and the second flow path portion 142. As illustrated in FIGS. 8 and 9, for example, the first tube 15b is constituted by a tube and the like made of hard resin, with one end connected to the first on-off valve 16A and the other end fluidly connected to the eighth hole 33A8 of the second flow path portion 142 through a boss formed on the surface of the base portion 33 on the windshield 32 side, for example. Note that the first tube 15b is preferably formed of a material that does not deform under pressure from the fluid flowing inside the first tube 15b.

The first tube 15b with such a configuration is disposed at a position separated from the pump 14 and the power supply unit 18 in a direction orthogonal to the axial direction D of the outer case 31 on the windshield side of the base portion 33.

As illustrated in FIG. 6, the second tube 15c is connected to the second on-off valve 16B and the third flow path groove 143c of the third flow path portion 143 and fluidly connects the second on-off valve 16B and the third flow path portion 143. As illustrated in FIGS. 8 and 9, for example, the second tube 15c is constituted by a tube and the like made of a hard resin material, with one end connected to the second on-off valve 16B and the other end connected to the tenth hole 33A10 of the third flow path portion 143 through a boss formed on the surface of the base portion 33 on the windshield 32 side, for example. The second tube 15c is preferably formed of a material that does not deform under pressure from the fluid flowing inside the second tube 15c.

The second tube 15c with such a configuration is disposed at a position separated from the pump 14 and the power supply unit 18 in a direction orthogonal to the axial direction D of the outer case 31 above the base portion 33. Specifically, the second tube 15c is disposed at the position next to the flow path plate 34 in the axial direction D of the outer case 31.

As illustrated in FIG. 6, the third tube 15d is connected to the third on-off valve 16C and the fourth flow path groove 144c of the fourth flow path portion 144 and fluidly connects the third on-off valve 16C and the fourth flow path portion 144. As illustrated in FIGS. 8 and 9, for example, the third tube 15d is constituted by a tube and the like made of a hard resin material, with one end connected to the third on-off valve 16C and the other end fluidly connected to the twelfth hole 33A12 of the fourth flow path portion 144 through a boss formed on the surface of the base portion 33 on the windshield 32 side, for example. The third tube 15d is preferably formed of a material that does not deform under pressure from the fluid flowing inside the third tube 15d.

The third tube 15d with such a configuration is disposed at a position separated from the pump 14 and the power supply unit 18 in a direction orthogonal to the axial direction D of the outer case 31 above the base portion 33. Specifically, the third tube 15d is disposed at the position next to the flow path plate 34 in the axial direction D of the outer case 31.

The on-off valve 16 opens and closes a portion of the flow path portion 15. Specifically, a plurality of on-off valves 16, specifically four on-off valves 16 are provided, for example, as illustrated in FIGS. 5 and 6, and selectively open and close the flow path connecting from the pump 14 to the pressing cuff 71 and the tensile cuff 74, the flow path connecting from the pump 14 to the sensing cuff 73, the flow path connecting from the pressing cuff 71 and the tensile cuff 74 to the atmosphere, and the flow path connecting from the sensing cuff 73 to the atmosphere, by the combination of opening and closing of each of the on-off valves 16. As a specific example, the four on-off valves 16 are constituted by the first on-off valve 16A, the second on-off valve 16B, the third on-off valve 16C, and the fourth on-off valve 16D.

The first on-off valve 16A is installed in the first hole 33A1 of the first flow path portion 141 and the first recess 34A1. The first on-off valve 16A is fluidly connected to the flow path groove 141c of the first flow path portion 141. Also, the first on-off valve 16A is connected to the first tube 15b. The first on-off valve 16A opens and closes the flow path connecting the pump 14 and the sensing cuff 73.

The second on-off valve 16B is installed in the second hole 33A2 of the first flow path portion 141 and the second recess 34A2. The second on-off valve 16B is fluidly connected to the second flow path groove 142c of the second flow path portion 142. Also, the second on-off valve 16B is connected to the second tube 15c. The second on-off valve 16B opens and closes the flow path connecting the pump 14 and the tensile cuff 74.

The third on-off valve 16C is installed in the third hole 33A3 of the third flow path portion 143 and the third recess 34A3. The third on-off valve 16C is fluidly connected to the third flow path groove 143c of the third flow path portion 143. Also, the third on-off valve 16C is connected to the third tube 15d. The third on-off valve 16C cooperates with the second on-off valve 16B and opens and closes the flow path connecting the pump 14 and the pressing cuff 71.

The fourth on-off valve 16D is installed in the fourth hole 33A4 of the fourth flow path portion 144 and the fourth recess 34A4. The fourth on-off valve 16D is fluidly connected to the fourth flow path groove 144c of the fourth flow path portion 144. The fourth on-off valve 16D cooperates with the second on-off valve 16B and the third on-off valve 16C and opens and closes the flow path connecting the pump 14 and the atmosphere.

As illustrated in FIGS. 9, 16 and 17, the first on-off valve 16A, the second on-off valve 16B, the third on-off valve 16C, and the fourth on-off valve 16D are disposed at positions separated from the pump 14 and the power supply unit 18 in the direction orthogonal to the axial direction D of the outer case 31. The first on-off valve 16A, the second on-off valve 16B, the third on-off valve 16C, and the fourth on-off valve 16D are disposed on an edge portion on the side opposite the buttons 41 in the second direction of the base portion 33, for example.

The first on-off valve 16A, the second on-off valve 16B, the third on-off valve 16C, and the fourth on-off valve 16D are fixed to the support plate 38. The first on-off valve 16A, the second on-off valve 16B, the third on-off valve 16C, and the fourth on-off valve 16D are fixed to the surface of the support plate 38 on the wrist 200 side, for example.

The pressure sensor 17 at least detects the pressure of the sensing cuff 73. The pressure sensor 17 is provided with the first pressure sensor 17A and the second pressure sensor 17B, for example. The pressure sensor 17 converts a detected pressure into an electrical signal, and outputs the electrical signal to the control substrate 20. For example, the first pressure sensor 17A and the second pressure sensor 17B are provided in the flow path connecting the first pressure sensor 17A of the flow path portion 15 and the sensing cuff 73. The flow path is continuous through the pressing cuff 71, the sensing cuff 73, and the tensile cuff 74 to the pump 14 by the opening and closing of each of the on-off valves, and thus the pressure in these flow paths corresponds to the pressure in the internal space of the pressing cuff 71, the sensing cuff 73, and the tensile cuff 74 connecting to the pump 14.

The first pressure sensor 17A is installed in the fifth hole 33A5 of the second flow path portion 142 and the fifth recess 45A5. The second pressure sensor 17B is installed in the sixth hole 33A6 of the second flow path portion 142 and the sixth recess 34A6. The first pressure sensor 17A and the second pressure sensor 17B detect the pressure of the second flow path groove 142c. The first pressure sensor 17A and the second pressure sensor 17B are fixed to the support plate 38.

Specifically, for example, the pressure sensor 17 detects the pressure of the sensing cuff 73, i.e., the pressure of the flow path portion 15 connecting the pump 14 and the sensing cuff 73, when the first on-off valve 16A is open and the second on-off valve 16B is closed. Also, the pressure sensor 17 detects the pressure of the sensing cuff 73 and the tensile cuff 74, i.e., the pressure of the flow path portion 15 connecting the pump 14, the sensing cuff 73, and the tensile cuff 74, when the first on-off valve 16A and the second on-off valve 16B are open and the third on-off valve 16C is closed. Furthermore, the pressure sensor 17 detects the pressure of the pressing cuff 71, the sensing cuff 73, and the tensile cuff 74, i.e., the pressure of the flow path portion 15 connecting the pump 14, the pressing cuff 71, the sensing cuff 73, and the tensile cuff 74, when the first on-off valve 16A, the second on-off valve 16B, and the third on-off valve 16C are open and the fourth on-off valve 16D is open or closed.

The power supply unit 18 is, for example, a secondary battery such as a lithium ion battery. The power supply unit 18 is electrically connected to the control substrate 20, as illustrated in FIG. 5. The power supply unit 18 supplies power to the control substrate 20.

As illustrated in FIG. 8, the power supply unit 18 is fixed at a position separated from the on-off valves 16 and the pressure sensors 17 in the direction orthogonal to the axial direction D of the outer case 31. Specifically, for example, the power supply unit 18 is fixed to a surface 14c of the pump 14 on the windshield 32 side.

As illustrated in FIG. 5, the control substrate 20 includes, for example, a substrate 51, an acceleration sensor 52, a communication unit 53, a storage unit 54, and a control unit 55. The control substrate 20 is constituted by the acceleration sensor 52, the communication unit 53, the storage unit 54, and the control unit 55 that are mounted on the substrate 51.

The substrate 51 is fixed to the base portion 33 of the case 11 using screws or the like.

The acceleration sensor 52 is, for example, a 3-axis acceleration sensor. The acceleration sensor 52 outputs, to the control unit 55, an acceleration signal representing acceleration of the device body 3 in three directions orthogonal to one another. For example, the acceleration sensor 52 is used to measure, from the detected acceleration, the amount of activity of a living body to which the blood pressure measurement device 1 is attached.

The communication unit 53 is configured to be capable to transmit and receive information to and from an external device wirelessly or by wire. For example, the communication unit 53 transmits information controlled by the control unit 55, and information of a measured blood pressure value, a pulse, and the like to an external device via a network, and receives a program or the like for software update from an external device via a network and sends the program or the like to the control unit 55.

In the present embodiment, the network is, for example, the Internet, but is not limited to this. The network may be a network such as a Local Area Network (LAN) provided in a hospital or may be direct communication with an external device using a cable or the like including a terminal of a predetermined standard such as a USB. Thus, the communication unit 53 may be configured to include a plurality of wireless antennas, micro-USB connectors, or the like.

The storage unit 54 pre-stores program data for controlling the overall blood pressure measurement device 1 and a fluid circuit 7, settings data for setting various functions of the blood pressure measurement device 1, calculation data for calculating a blood pressure value and a pulse from pressure measured by the pressure sensors 17, and the like. Additionally, the storage unit 54 stores information such as a measured blood pressure value and a measured pulse.

Also, the storage unit 54 pre-stores a threshold for determining the failure of the pump valve 14b, the first on-off valve 16A, the second on-off valve 16B, the third on-off valve 16C, and the fourth on-off valve 16D. The threshold is, for example, when the blood pressure measurement device 1 operates on the basis of program data stored in the storage unit 54, a value based on the program data.

In this example, the threshold is the time the pressure takes to reach atmospheric pressure based on an electrical signal from the first pressure sensor 17A and the second pressure sensor 17B, for example, when the sensing cuff 73, the tensile cuff 74, and the pressing cuff 71 are opened to the atmosphere after blood pressure measurement is completed.

In another example, the threshold is the pressure set by the program data in blood pressure measurement. For example, in a case where there is a step of expanding the tensile cuff 74 to a state suitable for blood pressure measurement after a step of expanding the pressing cuff 71 to a state suitable for blood pressure measurement, in the step of expanding the tensile cuff 74 to a state suitable for blood pressure measurement, air can be supplied to the sensing cuff 73 by closing the third on-off valve 16C. In this step, the pressure of the second flow path portion 142 also rises. In this step, a value relating to the speed of the rise in pressure over time, for example, the time taken until a predetermined pressure is reached, is used as the threshold. For example, in a state where the third on-off valve 16C malfunctions and cannot close, the air from the pump 14 is supplied also to the pressing cuff 71. Thus, the speed of the rise in pressure of the second flow path portion 142 is slower in a state where the third on-off valve 16C malfunctions and cannot close compared to a state where the third on-off valve 16C is closed to stop the supply of air to the pressing cuff 71. The threshold described above is merely an example, and no such limitation is intended.

The control unit 55 is constituted by one or more CPUs, and controls operation of the overall blood pressure measurement device 1 and operation of the fluid circuit. The control unit 55 is electrically connected to and supplies power to the display unit 12, the operation unit 13, the pump 14, each of the on-off valves 16 and the pressure sensors 17. Additionally, the control unit 55 controls operation of the display unit 12, the pump 14, and the on-off valves 16, based on electrical signals output by the operation unit 13 and the pressure sensors 17.

For example, as illustrated in FIG. 5, the control unit 55 includes a main Central Processing Unit (CPU) 56 that controls operation of the overall blood pressure measurement device 1, and a sub-CPU 57 that controls operation of the fluid circuit 7. For example, the main CPU 56 obtains measurement results such as blood pressure values, for example, the systolic blood pressure and the diastolic blood pressure, and the heart rate, from electrical signals output by the pressure sensor 17, and outputs an image signal corresponding to the measurement results to the display unit 12.

For example, the sub-CPU 57 drives the pump 14 and the on-off valves 16 to feed compressed air to the pressing cuff 71 and the sensing cuff 73 when an instruction to measure the blood pressure is input from the operation unit 13. In addition, the sub-CPU 57 controls driving and stopping of the pump 14 and opening and closing of the on-off valves 16 based on electrical signal output by the pressure sensors 17. The sub-CPU 57 controls the pump 14 and the on-off valves 16 to selectively feed compressed air to the pressing cuff 71 and the sensing cuff 73 and selectively depressurize the pressing cuff 71 and the sensing cuff 73.

In addition, the control unit 55 has a function of determining the failure of the pump valve 14b, the first on-off valve 16A, the second on-off valve 16B, the third on-off valve 16C, and the fourth on-off valve 16D on the basis of the electrical signals from each of the first pressure sensor 17A and the second pressure sensor 17B and the threshold stored in the storage unit 54.

As illustrated in FIGS. 1 to 4, the belt 4 includes a first belt 61 provided on the first pair of lugs 31a and a first spring rod 31b, and a second belt 62 provided on the second pair of lugs 31a and a second spring rod 31b. The belt 4 is wrapped around the wrist 200 with a curler 5 in between.

The first belt 61 is referred to as a so-called a parent and is configured like a band capable of being joined to the second belt 62. As illustrated in FIGS. 1 to 4, the first belt 61 includes a belt portion 61a and a buckle 61b. The belt portion 61a is configured like a band. The belt portion 61a is formed of an elastically deformable resin material. In addition, the belt portion 61a is flexible and includes a sheet-like insert member inside the belt portion 61a for suppressing stretching in the longitudinal direction of the belt portion 61a. The belt portion 61a includes a first hole portion 61c that is formed at one end portion and extends orthogonal to the longitudinal direction of the belt portion 61a, and a second hole portion 61d that is formed at the other end portion and extends orthogonal to the longitudinal direction of the first belt 61.

As illustrated in FIGS. 1 to 4, the first hole portion 61c is provided at the end portion of the belt portion 61a The first hole portion 61c has an inner diameter at which the spring rod 31b can be inserted into the first hole portion 61c and at which the first belt 61 can rotate with respect to the spring rod 31b. In other words, the first belt 61 is rotatably held by the outer case 31 by disposing the first hole portion 61c between the pair of lugs 31a and around the spring rod 31b.

As illustrated in FIGS. 1, 4, and 7, the second hole portion 61d is provided at the leading end of the belt portion 61a. The buckle 61b is attached to the second hole portion 61d.

As illustrated in FIGS. 1 and 3, the buckle 61b includes a frame body 61e in a rectangular frame shape and a prong 61f rotatably attached to the frame body 61e. A side of the frame body 61e to which the prong 61f is attached is inserted into the second hole portion 61d, and the frame body 61e is mounted rotatably with respect to the belt portion 61a.

The second belt 62 is referred to as a so-called blade tip, and is configured in a band-like shape having a width at which the second belt 62 can be inserted into the frame body 61e. The second belt 62 is formed of an elastically deformable resin material. In addition, the second belt 62 is flexible and includes a sheet-like insert member inside the second belt 62 for suppressing stretching in the longitudinal direction of the second belt 62.

In addition, as illustrated in FIGS. 1 and 2, the second belt 62 includes a plurality of small holes 62a into which the prong 61f is inserted. Additionally, the second belt 62 includes a third hole portion 62b provided at first end portion of the second belt 62 and extending orthogonally to the longitudinal direction of the second belt 62. The third hole portion 62*b* has an inner diameter at which the spring rod 31*b* can be inserted into the third hole portion 62*b* and at which the second belt 62 can rotate with respect to the spring rod 31*b*. In other words, the second belt 62 is rotatably held by the outer case 31 by disposing the third hole portion 62*b* between the pair of lugs 31*a* and around the spring rod 31*b*.

The second belt 62 is inserted into the frame body 61*e*, and the prong 61*f* is inserted into the small hole 62*a*, and thus the first belt 61 and the second belt 62 are integrally connected together, and the belt 4 as described above, together with the outer case 31, comes to have an annular shape following along the circumferential direction of the wrist 200. By shaping the belt 4 in an annular shape following along the circumferential direction of the wrist 200, the curler 5 is pressed and elastically deformed to follow along the circumferential direction of the wrist of the wearer of the blood pressure measurement device 1.

As illustrated in FIGS. 1 to 4, the curler 5 is configured in a band-like shape that curves in such a manner as to follow along the circumferential direction of the wrist 200. The curler 5 is formed with a first end and a second end spaced apart from each other. For example, a first end side outer surface of the curler 5 is fixed to the rear cover 35 of the device body 3. The curler 5 is disposed at a position where the first end and the second end protrude more to one side of the wrist 200 than the rear cover 35. Accordingly, the curler 5 is disposed with the first end and the second end to one side of the wrist 200 when the blood pressure measurement device 1 is attached to the wrist 200. Furthermore, the first end and the second end of the curler 5 are located adjacent to each other at a predetermined distance from each other. The curler 5 is formed of a resin material, for example. In a specific example, the curler 5 is formed of a polypropylene with a thickness of approximately 1 mm.

In a specific example, as illustrated in FIGS. 1 to 4, the curler 5 is configured in a band-like shape that curves following along the circumferential direction of the wrist. Furthermore, the curler 5 includes the disk-like cover portion 5*a* that is provided at a position facing the hand back side of the wrist 200 on the first end side and constitutes the rear lid together with the rear cover 35, and an escape portion 5*b* that is provided in the peripheral region of the cover portion 5*a* and allows the first joining members 35*a* that fix the outer case 31 and the rear cover 35 to be moveable. For example, the cover portion 5*a* and the adjacent portion of the cover portion 5*a* of the curler 5 are formed in a plate-like shape, and the first and second end sides is formed curving with a predetermined curvature more than the cover portion 5*a*. Furthermore, the length of the curler 5 from the cover portion 5*a* to the first end is less than the length from the cover portion 5*a* to the second end. In a specific example, the shorter side of the curler 5 from the cover portion 5*a* to the first end is disposed on the hand back side of the wrist, and the longer side from the cover portion 5*a* to the second end extends from the hand back side of the wrist, passing through one side, to the hand palm-side of the wrist 200.

Additionally, as illustrated in FIG. 25, the curler 5 is formed in a shape with the second end located at the inner circumferential surface side of the first end side when the first end and the second end are brought close. In a specific example, the width of the curler 5 in the width direction of the wrist 200 is set to be greater on the hand back side of the wrist 200 than on the hand palm-side of the wrist 200. Furthermore, the radius of curvature of the first end of the curler 5 on the hand back side of the wrist 200 is set to be greater than the radius of curvature of the second end on the hand palm-side of the wrist 200. According to such a configuration, when both end sides of the curler 5 are brought to abut, the second end is disposed further to the inward side of the curler 5 than the first end. Furthermore, the curler 5 is provided with a recess 5*c* provided adjacent to the cover portion 5*a* on a portion of the cover portion 5*a*, on the outer surface on the first end side from the cover portion 5*a*, and also on the outer surface on the shorter side extending from the cover portion 5*a*.

The cover portion 5*a* includes an insert member 5*d* for reinforcement which is inserted. The cover portion 5*a* is fixed to the wrist 200 side of the outer case 31 with the fixed rear cover 35 in between. The cover portion 5*a* includes screw holes 5*e* provided at positions facing the four hole portions 35*c* of the rear cover 35, into which the first joining members 35*a* for fixing the rear cover 35 are screwed, and includes three hole portions 5*f* for connecting the cuff structure 6 to the device body 3.

The escape portion 5*b* is a relief for disposing the first joining members 35*a* in the rear cover 35 and for disposing a tool for rotating the first joining members 35*a* in a manner so that the first joining members 35*a* do not interfere with the curler 5 when the rear cover 35 is fixed to the outer case 31 from the rear cover 35 side with the first joining members 35*a*.

The three hole portions 5*f* include a first hole portion 5*f*1 formed with an inner diameter into which the connection portion 84 described below of the pressing cuff 71 can be inserted, a second hole portion 5*f*2 formed with an inner diameter into which the connection portion 93 described below of the sensing cuff 73 can be inserted, and the third hole portion 5*f*3 formed with an inner diameter into which the connection portion 103 described below of the tensile cuff 74 can be inserted. In the present embodiment, the second hole portion 5*f*2 is disposed in the cover portion 5*a* closer to the second end side on the hand palm-side of the curler 5 than the first hole portion 5*f*1 and the third hole portion 5*f*3.

The curler 5 with such a configuration is fixed to the outer case 31 with the first end and the second end orientated to face the second belt 62 of the belt 4. Also, the curler 5 at least at the position facing the hand palm-side of the wrist 200 curves along the circumferential direction along with the hand palm-side of the wrist 200, and thus the cuff structure 6 facing the hand palm-side of the wrist 200 is held in a curved state following along the shape of the hand palm-side of the wrist 200.

The curler 5 has a hardness appropriate to provide flexibility and shape retainability. Here, "flexibility" refers to deformation of the shape of the curler 5 in a radial direction at the time of application of an external force of the belt 4 to the curler 5. For example, "flexibility" refers to deformation of the shape of the curler 5 in a side view in which the curler 5 approaches the wrist, is along the shape of the wrist, or follows to the shape of the wrist when the curler 5 is pressed by the belt 4. Furthermore, "shape retainability" refers to the ability of the curler 5 to maintain a pre-imparted shape when no external force is applied to the curler 5. For example, "shape retainability" refers to, in the present embodiment, the ability of the curler 5 to maintain the shape in a shape curving along the circumferential direction of the wrist.

The cuff structure 6 is disposed on an inner circumferential surface of the curler 5, and is held along the shape of the inner circumferential surface of the curler 5. As a specific example, the cuff structure 6 is held by disposing the pressing cuff 71 and the tensile cuff 74 on the inner circumferential surface of the curler 5, and fixing the cuff structure 6 by a joining layer 75 provided between the curler 5 and the pressing cuff 71 and the tensile cuff 74. In the present embodiment, the joining layer 75 is adhesive or double-sided tape.

The curler 5 is formed of a resin material. For example, the curler 5 is formed of a polypropylene with a thickness of approximately 1 mm.

As illustrated in FIGS. 1 to 4, 7 and 26, the cuff structure 6 includes the pressing cuff 71, a back plate 72, the sensing cuff 73, and the tensile cuff 74. Also, the cuff structure 6 is provided with the joining layer 75 for joining components each other and joining the curler 5 and the cuffs 71 and 74. The cuff structure 6 is fixed to the curler 5. The cuff structure 6 includes the pressing cuff 71, the back plate 72, and the sensing cuff 73 that are stacked one another and disposed on the curler 5, and the tensile cuff 74 that is spaced apart from the pressing cuff 71, the back plate 72, and the sensing cuff 73 and disposed on the curler 5.

In a specific example, as illustrated in FIG. 4, the cuff structure 6 is fixed to the inner circumferential surface of the curler 5 on the hand palm-side of the wrist 200 with the pressing cuff 71, the back plate 72, and the sensing cuff 73 stacked in this order from the inner circumferential surface of the curler 5 toward the wrist 200 side. In addition, the cuff structure 6 includes the tensile cuff 74 disposed on the inner circumferential surface of the curler 5 on the hand back side of the wrist 200. Each of the members of the cuff structure 6 is fixed to an adjacent member of the cuff structure 6 in a stacking direction by the joining layer 75.

The pressing cuff 71 is fluidly connected to the pump 14 through the flow path portion 15. The pressing cuff 71 is inflated to pressing the back plate 72 and the sensing cuff 73 toward the wrist 200 side. As illustrated in FIGS. 21, 22 and 26 to 29, the pressing cuff 71 includes a plurality of, for example, two-layer air bags 81, a target join portion 82 provided on the air bag 81 facing the curler 5, a flow path body 83 communicating with the air bags 81, and the connection portion 84 provided on the leading end of the flow path body 83. The pressing cuff 71 with such a configuration is configured by integrally welding a plurality of sheet members 86 together.

Here, the air bags 81 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. The plurality of air bags 81 are stacked and are in fluid communication with one another in the stacking direction.

Each of the air bags 81 is formed in a rectangular bag-like shape that is long in one direction. Additionally, the air bags 81 are set so that the width in the lateral direction is the same as the width in the lateral direction of the curler 5. The air bags 81 are each constituted by, for example, combining two sheet members 86 and, as illustrated in FIGS. 21, 22, and 26 to 29, welding a weld portion 81*a* using heat into a rectangular frame shape long in one direction. In addition, the two-layer air bags 81 are constituted by forming with integrally combining two air bags 81 by welding using heat, or with welding together a pair of sheet members 86 facing adjacent air bag 81 and welding to the air bag 81. In a specific example, the two-layer air bags 81 are fluidly continuous through openings provided in the sheet members 86 facing one another. In addition, in the two-layer air bags 81, by welding the opposing sheet members 86 together in a quadrilateral frame shape smaller than the weld portion 81*a* located on the outer peripheral edge and surrounding the plurality of openings with this weld portion (join portion) 81*b*, the adjacent air bags 81 are integrally formed and made to be fluidly continuous on the inner side of the weld portion 81*b*.

A single or a plurality of target join portions 82 are provided at at least a portion of the edge portion of the air bag 81 disposed adjacent to the curler 5. The target join portion 82 is formed by a portion of the sheet member 86 forming the air bag 81.

An example of the present embodiment will be described using the examples illustrated in FIGS. 20 to 22 and 26 to 28 in which one target join portion 82 is provided on the edge portion in the lateral direction of each of the air bags 81. Note that, for example, the target join portion 82 may be divided in the longitudinal direction of the air bag 81 by a slit, or a plurality of target join portions 82 may be provided in the longitudinal direction of the air bag 81. The target join portion 82 is at least joined to the outer circumferential surface of the curler 5 when the pressing cuff 71 is disposed on the inner circumferential surface of the curler 5. Furthermore, for example, two target join portions 82 are stacked and welded.

Note that the two target join portions 82 are set to have a different length to the length in the lateral direction of the air bags 81, for example. In this example, the two target join portions 82 are stacked and welded at the first end side in the lateral direction of the curler 5. Note that as long as the two target join portions 82 are able to be disposed with the leading end on the outer circumferential surface of the curler 5, the length is able to be set as appropriate, and the two target join portions 82 may be stackable or not. However, in a case where the length is set to a stackable length, the length is preferably a length such that the leading end does not extend further out than the outer edge of the outer circumferential surface of the curler 5.

As illustrated in FIGS. 20 and 26 to 28, the flow path body 83 is integrally provided on a single air bag 81, for example, on a portion of one edge portion in the longitudinal direction of the air bag 81 adjacent to the curler 5. As a specific example, the flow path body 83 is provided at the end portion of the air bag 81 near the device body 3. Additionally, the flow path body 83 is formed in a shape that is long in one direction and has less width than the width of the air bag 81 in the lateral direction and formed with a leading end having a circular shape. The flow path body 83 includes the connection portion 84 on the leading end. The flow path body 83 is connected to the flow path portion 15 through the connection portion 84 and constitutes a flow path between the flow path portion 15 of the device body 3 and the air bag 81.

The flow path body 83 is constituted by welding a portion of sheet members 86, which is adjacent to a region of the sheet members 86 constituting the air bags 81, in a frame shape long in one direction using heat, in a state where the connection portion 84 is disposed on the two sheet members 86. The flow path body 83 with such a configuration is disposed between the inner circumferential surface of the curler 5 and the tensile cuff 74, and the leading end is disposed at a position facing the first hole portion 5/1 on the main surface on the wrist 200 side of the region where the cover portion 5*a* of the curler 5 is provided. In addition, the width of the flow path body 83 not including a weld portion 83*a* is formed to be 3.8 mm, for example.

Note that, a portion of the weld portion 81*a*, where the two sheet members 86 are welded in a rectangular frame shape, is not welded and the air bags 81 provided with the flow path body 83 are constituted to be continuous with the weld portion 83a constituting the flow path body 83, and thus the air bags 81 are fluidly continuous with the flow path body 83.

The connection portion 84 is, for example, a nipple. The connection portion 84 is provided at the leading end of the flow path body 83. The leading end of the connection portion 84 is exposed from the sheet member 86, facing the curler 5, of the two sheet members 86 constituting the flow path body 83. The connection portion 84 is inserted in the first hole portion 5f1 of the cover portion 5a and is connected to the flow path portion 15.

As a specific example, as illustrated in FIGS. 21, 22, and 37, the pressing cuff 71 includes a first sheet member 86a, a second sheet member 86b, a third sheet member 86c, and a fourth sheet member 86d in this order from the wrist 200 side. The second sheet member 86b constitutes a first-layer air bag 81 along with the first sheet member 86a, the third sheet member 86c is integrally joined to the second sheet member 86b and constitutes the target join portion 82, and the fourth sheet member 86d constitutes a second-layer air bag 81 and the flow path body 83 along with the third sheet member 86c. Note that the pressing cuff 71 is integrally constituted by joining adjacent sheet members 86 by welding using heat.

The first sheet member 86a and the second sheet member 86b are configured in a similar rectangular shape to the air bags 81, and peripheral edge portions of the four sides are welded to constitute the air bags 81. The second sheet member 86b and the third sheet member 86c are disposed facing each other, and each includes a plurality of openings 86b1 and 86c1 through which the two air bags 81 are fluidly continuous. Additionally, the second sheet member 86b and the third sheet member 86c are integrally joined by the peripheral region of the plurality of openings 86b1 and 86c1 being welded using heat in a quadrilateral frame shape smaller than the welded four sides of the air bags 81.

The third sheet member 86c, for example, is constituted in a shape that allows the air bags 81, the target join portion 82, and the flow path body 83 to be constituted. The fourth sheet member 86d, for example, is constituted in a shape that allows the air bags 81 and the flow path body 83 to be constituted. Furthermore, the fourth sheet member 86d includes a hole portion 86d1 into which the leading end of the connection portion 84 can be inserted, for example.

The air bags 81, the target join portion 82, and the flow path body 83 are constituted by the third sheet member 86c and the fourth sheet member 86d being disposed facing one another, welded using heat along the peripheral edge shape of the air bag 81 and the flow path body 83 so that the air bag 81 and the flow path body 83 are fluidly continuous, and cut in a predetermined shape.

The fourth sheet member 86d is disposed with the connection portion 84 at the hole portion 86d1, and the peripheral region of the hole portion 86d1 is welded to the connection portion 84 using heat. Furthermore, the fourth sheet member 86d is joined with the inner circumferential surface of the curler 5 with the joining layer 75 in between, and the target join portion 82 of the third sheet member 86c is joined to the outer circumferential surface of the curler 5 with the joining layer 75 in between.

As illustrated in FIGS. 21, 22, and 37, the back plate 72 is applied to the outer surface of the first sheet member 86a of the pressing cuff 71 by the joining layer 75. The back plate 72 is formed in a plate shape using a resin material. The back plate 72 is made of polypropylene, for example, and is formed into a plate shape having a thickness of approximately 1 mm. The back plate 72 has shape followability.

Here, "shape followability" refers to a function of the backplate 72 by which the back plate 72 can be deformed in such a manner as to follow the shape of a contacted portion of the wrist 200 to be disposed, the contacted portion of the wrist 200 refers to a region of the wrist 200 that is faced by the back plate 72, and the contact as used herein includes both direct contact and indirect contact with the sensing cuff 73 in between.

For example, as illustrated in FIG. 22, the back plate 72 includes a plurality of grooves 72a extending in both main surfaces of the back plate 72 in a direction orthogonal to the longitudinal direction. As illustrated in FIG. 22, the plurality of grooves 72a are provided in both main surfaces of the back plate 72. The plurality of grooves 72a provided in one of the main surfaces face the corresponding grooves 72a provided in the other main surface in the thickness direction of the back plate 72. Additionally, the plurality of grooves 72a are disposed at equal intervals in the longitudinal direction of the back plate 72.

In the back plate 72, portions including the plurality of grooves 72a are thinner than portions including no grooves 72a and thus the portions including the plurality of grooves 72a are easily deformed. Accordingly, the back plate 72 is deformed in such a manner as to follow to the shape of the wrist 200, and has shape followability of extending in the circumferential direction of the wrist. The back plate 72 is formed such that the length of the back plate 72 is sufficient to cover the hand palm-side of the wrist 200. The back plate 72 transfers the pressing force from the pressing cuff 71 to the back plate 72 side main surface of the sensing cuff 73 in a state in which the back plate 72 is extending along the shape of the wrist 200.

The sensing cuff 73 is fluidly connected to the pump 14 through the flow path portion 15. The sensing cuff 73 is fixed to the main surface of the back plate 72 on the wrist 200 side. The sensing cuff 73 is in direct contact with a region of the wrist 200 where an artery 210 resides, as illustrated in FIGS. 4 and 37. The artery 210 as used herein is the radial artery and the ulnar artery. The sensing cuff 73 is formed in the same shape as that of the back plate 72 or a shape that is smaller than that of the back plate 72, in the longitudinal direction and the width direction of the back plate 72. The sensing cuff 73 is inflated to compress a hand palm-side region of the wrist 200 in which the artery 210 resides. The sensing cuff 73 is pressed by the inflated pressing cuff 71 toward the wrist 200 side with the back plate 72 in between.

In a specific example, as illustrated in FIGS. 21, 22, 30, and 31, the sensing cuff 73 includes one air bag 91, a flow path body 92 that communicates with the air bag 91, and the connection portion 93 provided at the leading end of the flow path body 92. One main surface of the air bag 91 of the sensing cuff 73 is fixed to the back plate 72. For example, the sensing cuff 73 is joined to the main surface of the back plate 72 on the wrist 200 side by the joining layer 75. The sensing cuff 73 with such a configuration is constituted by welding two sheet members 96.

Here, the air bag 91 is a bag-like structure, and in the present embodiment, the blood pressure measurement device 1 is configured to use air with the pump 14, and thus the present embodiment will be described using the air bag. However, in a case where a fluid other than air is used, the bag-like structure may be a fluid bag that are inflated by a fluid.

The air bag 91 is constituted in a rectangular shape that is long in one direction. The air bag 91 is constituted by, for example, combining the two sheet members 96 long in one direction and, as illustrated in FIGS. 21, 22, 26, 30, and 31, welding a weld portion 91*a* using heat into a rectangular frame shape long in one direction. Also, the air bag 91, for example, includes a junction margin 91*b* for ensuring area for joining the air bag 91 to the back plate 72 using the joining layer 75. The junction margin 91*b* is formed by the sheet member 96 facing the back plate 72, for example.

The flow path body 92 is integrally provided at a portion of one edge portion of the air bag 91 in the longitudinal direction. As a specific example, the flow path body 92 is provided at the end portion of the air bag 91 near the device body 3. Additionally, the flow path body 92 is formed in a shape that is long in one direction and has less width than the width of the air bag 91 in the lateral direction, and formed with a leading end having a circular shape. The flow path body 92 includes the connection portion 93 on the leading end. The flow path body 92 is connected to the flow path portion 15 through the connection portion 93 and constitutes a flow path between the flow path portion 15 of the device body 3 and the air bag 91.

The flow path body 92 is constituted by welding a portion of sheet members 96, which is adjacent to a region of the sheet members 96 constituting the air bag 91, in a frame shape long in one direction using heat, in a state where the connection portion 93 is disposed on the two sheet members 96. Note that, a portion of the weld portion 91*a*, where the two sheet members 96 are welded in a rectangular frame shape, is not welded and the air bag 91 is constituted to be continuous with the weld portion 92*a* constituting the flow path body 92, and thus the air bag 91 and the flow path body 92 are fluidly continuous. The flow path body 92 with such a configuration is disposed between the inner circumferential surface of the curler 5 and the tensile cuff 74, and the leading end is disposed at a position facing the second hole portion 5*f*2 on the main surface on the wrist 200 side of the region where the cover portion 5*a* of the curler 5 is provided. In addition, the width of the flow path body 92 not including the weld portion 92*a* is 3.8 mm, for example.

The connection portion 93 is, for example, a nipple. The connection portion 93 is provided at the leading end of the flow path body 92. Also, the leading end of the connection portion 93 is externally exposed from the sheet member 96 facing the curler 5 and the back plate 72, of the two sheet members 96 constituting the flow path body 92. The connection portion 93 is inserted in the second hole portion 5*f*2 of the cover portion 5*a* and is connected to the flow path portion 15.

In a specific example, the sensing cuff 73 includes a fifth sheet member 96*a* and a sixth sheet member 96*b* in this order from the wrist 200 side as illustrated in FIGS. 21 and 22. Note that the sensing cuff 73 is constituted by joining adjacent sheet members 96 by welding using heat.

For example, the fifth sheet member 96*a* and the sixth sheet member 96*b* are constituted in a shape that allows the air bag 91, the junction margin 91*b*, and the flow path body 92 to be constituted. The air bag 91 and the flow path body 92 are constituted by the fifth sheet member 96*a* and the sixth sheet member 96*b* being disposed facing one another, welded using heat along the peripheral edge shape of the air bag 91 and the flow path body 92 so that the air bag 91 and the flow path body 92 are fluidly continuous, and cut in a predetermined shape.

Furthermore, the sixth sheet member 96*b* includes a hole portion 96*b*1 into which the leading end of the connection portion 93 can be inserted, for example. The sixth sheet member 96*b* is disposed with the connection portion 93 at the hole portion 96*b*1, and the peripheral region of the hole portion 96*b*1 is welded to the connection portion 93 using heat. The sixth sheet member 96*b* is joined to the inner circumferential surface of the back plate 72 with the joining layer 75 in between.

The tensile cuff 74 is fluidly connected to the pump 14 through the flow path portion 15. The tensile cuff 74 is inflated to press the curler 5 such that the curler 5 is spaced apart from the wrist 200, pulling the belt 4 and the curler 5 toward the hand back side of the wrist 200. The tensile cuff 74 includes a plurality of, for example, six-layer air bags 101, a target join portion 102 provided on the air bag 101 facing the curler 5, and the connection portion 103 provided on the air bag 101 facing the curler 5. The tensile cuff 74 with such a configuration is constituted by welding a plurality of sheet members 106. In addition, the tensile cuff 74 is fixed to the region where the flow path bodies 83 and 92 are provided and the curler 5, including the cover portion 5*a*, on the hand back side of the wrist 200. In other words, the flow path body 83 of the pressing cuff 71 and the flow path body 92 of the sensing cuff 73 are disposed between the curler 5 on the hand back side of the wrist 200 and the tensile cuff 74.

Additionally, the tensile cuff 74 is configured such that the thickness of the tensile cuff 74 in an inflating direction, in the present embodiment, in the direction in which the curler 5 and the wrist 200 face each other, during inflation, is larger than the thickness of the pressing cuff 71 in the inflating direction during inflation and than the thickness of the sensing cuff 73 in the inflating direction during inflation. Specifically, the air bags 101 of the tensile cuff 74 include more layer structures than the air bags 81 in the pressing cuff 71 and the air bag 91 in the sensing cuff 73, and have thicker thickness than the pressing cuff 71 and the sensing cuff 73 when the air bags 101 are inflated from the curler 5 toward the wrist 200.

Here, the air bags 101 are bag-like structures, and in the present embodiment, the blood pressure measurement device 1 is configured to use air with the pump 14, and thus the present embodiment will be described using the air bags. However, in a case where a fluid other than air is used, the bag-like structures may be fluid bags that are inflated by a fluid. A plurality of the air bags 101 are stacked and are in fluid communication in the stacking direction.

Each of the air bags 101 is formed in a rectangular bag-like shape that is long in one direction. Additionally, the air bags 101 are set so that the width in the lateral direction is the same as the width in the lateral direction of the curler 5. The air bags 101 are each constituted by, for example, combining two sheet members 106 and, as illustrated in FIGS. 23, 24, 26, and 27, welding a weld portion 101*a* using heat into a rectangular frame shape long in one direction. In addition, the six-layer air bags 101 are, for example, constituted by forming with integrally combining six air bags 101 by welding using heat, or with welding together a pair of sheet members 106 facing adjacent air bag 101 and welding to the air bag 101. The six-layer air bags 101 are fluidly continuous through openings provided in the sheet members 106 facing one another. In addition, in the six-layer air bags 101, by welding the opposing sheet members 106 together in a quadrilateral frame shape smaller than the weld portion 81*a* located on the outer peripheral edge and surrounding the plurality of openings with a weld portion 101*b*, the adjacent air bags 101 are integrally formed and made to be fluidly continuous on the inner side of the weld portion 101*b*.

A single or a plurality of target join portions 102 are provided at at least a portion of the edge portion of the air bag 101 disposed adjacent to the curler 5. The target join portion 102 is formed by a portion of the sheet member 106 forming the air bag 101.

An example of the present embodiment will be described using examples in which two target join portions 102 are each provided in the longitudinal direction of the air bags 101 on the edge portion in the lateral direction of each of the air bags 101. Note that, for example, the target join portions 102 are provided on the air bags 101 avoiding the positions facing the cover portion 5a of the curler 5. Furthermore, for example, the target join portion 102 includes an escape portion 102a, which is for externally exposing a power feeding terminal 8b described below of the power feeding unit 8 provided on the curler 5, at a portion facing the power feeding terminal 8b. The escape portion 102a, for example, is an opening through which the power feeding terminal 8b can be externally exposed and has a circular shape as an example.

The target join portion 102 is at least joined to the outer circumferential surface of the curler 5 when the tensile cuff 74 is disposed on the inner circumferential surface of the curler 5. Additionally, the target join portions 102 disposed at the same position in the lateral direction of the air bags 101 are stacked and welded.

Note that the two target join portions 102 are set to have a different length to the length in the lateral direction of the air bags 101, for example. In this example, the two target join portions 102 are stacked and welded at the first end side in the lateral direction of the curler 5. Note that as long as the two target join portions 102 are able to be disposed with the leading end on the outer circumferential surface of the curler 5, the length is able to be set as appropriate and the two target join portions 102 may be stackable or not. However, in a case where the length is set to a stackable length, the length is preferably a length such that the leading end does not extend further out than the outer edge of the outer circumferential surface of the curler 5.

The connection portion 103 is, for example, a nipple. The connection portion 103 is provided at a position facing the third hole portion 5f3 of the cover portion 5a in a central region in the longitudinal direction of the air bag 101 disposed adjacent to the curler 5. The leading end of the connection portion 103 is exposed from the sheet member 106 facing the curler 5, of the two sheet members 106 forming the air bag 101. The connection portion 103 is inserted in the third hole portion 5f3 of the cover portion 5a and is connected to the flow path portion 15.

In a specific example, as illustrated in FIGS. 23 and 24, the tensile cuff 74 includes a seventh sheet member 106a, an eighth sheet member 106b, a ninth sheet member 106c, a tenth sheet member 106d, an eleventh sheet member 106e, a twelfth sheet member 106f, a thirteenth sheet member 106g, a fourteenth sheet member 106h, a fifteenth sheet member 106i, a sixteenth sheet member 106j, a seventeenth sheet member 106k, and an eighteenth sheet member 106l in this order from the wrist 200 side. Note that the tensile cuff 74 is integrally constituted by joining adjacent sheet members 106 by welding using heat.

The seventh sheet member 106a to the eighteenth sheet member 106l are constituted in a similar rectangular shape to the air bags 101. Edge portions of four sides of the seventh sheet member 106a are welded to corresponding peripheral edge portions of four sides of the eighth sheet member 106b to constitute a first-layer air bag 101. The eighth sheet member 106b and the ninth sheet member 106c are disposed facing each other, and each includes a plurality of openings 106b1 and 106c1 through which the two air bags 101 are fluidly continuous. Additionally, the eighth sheet member 106b and the ninth sheet member 106c are integrally joined by the peripheral region of the plurality of openings 106b1 and 106c1 being welded using heat in a quadrilateral frame shape smaller than the welded four sides of the air bags 101.

Edge portions of four sides of the ninth sheet member 106c are welded to corresponding peripheral edge portions of four sides of the tenth sheet member 106d to constitute a second-layer air bag 101.

As illustrated in FIGS. 23 and 24, the tenth sheet member 106d and the eleventh sheet member 106e include a plurality of openings 106d1 and 106e1 disposed facing one another and through which the two air bags 101 are fluidly continuous. Additionally, the tenth sheet member 106d and the eleventh sheet member 106e are integrally joined by the peripheral region of the plurality of openings 106d1 and 106e1 being welded using heat in a quadrilateral frame shape smaller than the welded four sides of the air bags 101. Edge portions of four sides of the eleventh sheet member 106e are welded to corresponding peripheral edge portions of four sides of the twelfth sheet member 106f to constitute a third-layer air bag 101.

As illustrated in FIGS. 23 and 24, the twelfth sheet member 106f and the thirteenth sheet member 106g include a plurality of openings 106f1 and 106g1 disposed facing one another and through which the two air bags 101 are fluidly continuous. Additionally, the twelfth sheet member 106f and the thirteenth sheet member 106g are integrally joined by the peripheral region of the plurality of openings 106f1 and 106g1 being welded using heat in a quadrilateral frame shape smaller than the welded four sides of the air bags 101. Edge portions of four sides of the thirteenth sheet member 106g are welded to corresponding peripheral edge portions of four sides of the fourteenth sheet member 106h to constitute a fourth-layer air bag 101.

As illustrated in FIGS. 23 and 24, the fourteenth sheet member 106h and the fifteenth sheet member 106i include a plurality of openings 106h1 and 106i1 disposed facing one another and through which the two air bags 101 are fluidly continuous.

Additionally, the fourteenth sheet member 106h and the fifteenth sheet member 106i are integrally joined by the peripheral region of the plurality of openings 106h1 and 106i1 being welded using heat in a quadrilateral frame shape smaller than the welded four sides of the air bags 101. Edge portions of four sides of the fifteenth sheet member 106i are welded to corresponding peripheral edge portions of four sides of the sixteenth sheet member 106j to constitute a fifth-layer air bag 101.

As illustrated in FIGS. 23 and 24, the sixteenth sheet member 106j and the seventeenth sheet member 106k include a plurality of openings 106j1 and 106k1 disposed facing one another and through which the two air bags 101 are fluidly continuous. Also, the seventeenth sheet member 106k, for example, is constituted in a shape that allows the air bag 101 and the target join portion 102 to be constituted. Additionally, the sixteenth sheet member 106j and the seventeenth sheet member 106k are integrally joined by the peripheral region of the plurality of openings 106j1 and 106k1 being welded using heat in a quadrilateral frame shape smaller than the welded four sides of the air bags 101. The seventeenth sheet member 106k and the eighteenth sheet member 106l are welded using heat along the peripheral edge shape of the air bag 101 and cut in a predetermined shape to constitute a sixth-layer air bag 101 and the target join portion 102.

Furthermore, the eighteenth sheet member 106*l* includes a hole portion 106*l*1 into which the leading end of the connection portion 103 can be inserted, for example. The eighteenth sheet member 106*l* is disposed with the connection portion 103 at the hole portion 106*l*1, and the peripheral region of the hole portion 106*l*1 is welded to the connection portion 103 using heat. Furthermore, the eighteenth sheet member 106*l* is joined with the inner circumferential surface of the curler 5 with the joining layer 75 in between, and the target join portion 102 of the seventeenth sheet member 106*k* is joined to the outer circumferential surface of the curler 5 with the joining layer 75 in between.

Additionally, each of the sheet members 86, 96, and 106 forming the pressing cuff 71, the sensing cuff 73, and the tensile cuff 74 are formed of a thermoplastic resin material. The thermoplastic resin material is a thermoplastic elastomer. Examples of thermoplastic resin material constituting the sheet members 86, 96, and 106 include thermoplastic polyurethane based resin (hereinafter referred to as TPU), polyvinyl chloride resin, ethylene-vinyl acetate resin, thermoplastic polystyrene based resin, thermoplastic polyolefin resin, thermoplastic polyester based resin, and thermoplastic polyamide resin. Note that, in the pressing cuff 71 and the sensing cuff 73, of at least the plurality of sheet members 86 and 106 constituting the air bags 81 and 101, at least the sheet members 86 and 106 welded to the curler 5 are constituted by a material similar to the material of the curler 5.

For example, the sheet members 86, 96, and 106 are formed using a molding method such as T-die extrusion molding or injection molding. After being molded by each molding method, the sheet members 86, 96, and 106 are sized into predetermined shapes, and the sized individual pieces are joined by welding or the like to constitute bag-like structures 81, 91, and 101. A high frequency welder or laser welding is used as the welding method.

The fluid circuit 7 is constituted by the case 11, the pump 14, the flow path portion 15, the on-off valves 16, the pressure sensors 17, the pressing cuff 71, the sensing cuff 73, and the tensile cuff 74. A specific example of the fluid circuit 7 will be described below.

As illustrated in FIG. 5, for example, the fluid circuit 7 includes a first flow path 7*a* in which the pump 14, the sensing cuff 73, the first pressure sensor 17A and the second pressure sensor 17B are continuous through the first on-off valve 16A, a second flow path 7*b* which is constituted by branching from the first flow path 7*a* between the pump 14 and the first on-off valve 16A and is continuous from the pump 14 to the atmosphere through the second on-off valve 16B, the third on-off valve 16C, and the fourth on-off valve 16D sequentially in this order, a third flow path 7*c* which is constituted by branching from an intermediate portion of the second flow path 7*b* between the second on-off valve 16B and the third on-off valve 16C and is continuous from the pump 14 to the tensile cuff 74, and a fourth flow path 7*d* which is constituted by branching from an intermediate portion of the second flow path 7*b* between the third on-off valve 16C and the fourth on-off valve 16D and is continuous from the pump 14 to the pressing cuff 71.

As illustrated in FIG. 6, the first flow path 7*a* in constituted by the first flow path portion 141, the first on-off valve 16A, the first tube 15*b*, and the second flow path portion 142. The first flow path 7*a* is fluidly connected to the pump valve 14*b* of the pump 14.

The second flow path 7*b* is constituted by the second on-off valve 16B, the second tube 15*c*, the third flow path portion 143, the third tube 15*d*, the fourth flow path portion 144, and the fourth on-off valve 16D. The third flow path 7*c* is constituted by the third flow path portion 143. The fourth flow path 7*d* is constituted by the fourth flow path portion 144.

In the fluid circuit 7 with such a configuration, by the second on-off valve 16B and the third on-off valve 16C being open and the first on-off valve 16A and the fourth on-off valve 16D being closed, the third flow path 7*c* and the fourth flow path 7*d* branching from the second flow path 7*b* are connected to the pump 14, and the pump 14, the pressing cuff 71, and the tensile cuff 74 are fluidly connected.

In the fluid circuit 7, by the first on-off valve 16A, the second on-off valve 16B, and the third on-off valve 16C being open and the fourth on-off valve 16D being closed, the first flow path 7*a* and the third flow path 7*c* and the fourth flow path 7*d* branching from the second flow path 7*b* are connected to the pump 14, and the pump 14, the pressing cuff 71, and the tensile cuff 74 and the pump 14 and the sensing cuff 73 are fluidly connected. In the fluid circuit 7, by the second on-off valve 16B, the third on-off valve 16C, and the fourth on-off valve 16D being open and the first on-off valve 16A being closed, the second flow path 7*b*, the third flow path 7*c*, and the fourth flow path 7*d* are connected to the pump 14, and the pump 14, the pressing cuff 71, the tensile cuff 74, and the atmosphere are fluidly connected. In the fluid circuit 7, by the first on-off valve 16A, the second on-off valve 16B, the third on-off valve 16C, and the fourth on-off valve 16D being open, the first flow path 7*a*, the second flow path 7*b*, the third flow path 7*c*, and the fourth flow path 7*d* are connected to the pump 14, and the pump 14, the pressing cuff 71, the sensing cuff 73, the tensile cuff 74, and the atmosphere are fluidly connected.

As illustrated in FIGS. 7 and 20, the power feeding unit 8 is provided in the recess 5*c* formed in the outer surface of the curler 5 on the first end side that projects from the device body 3. For example, the power feeding unit 8 is configured to be capable to connect to a connector provided on a charging cable of a charger.

As illustrated in FIGS. 3, 9, and 11, the power feeding unit 8 is provided with a wiring portion 8*a*, the power feeding terminal 8*b*, and a cover 8*c* that covers the wiring portion 8*a* disposed in the recess 5*c* of the curler 5. The first end of the wiring portion 8*a* is connected to the power feeding terminal 8*b*, and the second end is connected to the control unit 55. The power feeding terminal 8*b* is constituted by two circular terminals, for example. For example, the wiring portion 8*a* and the power feeding terminal 8*b* are formed of flexible printed circuits (FPC) and the like including a base film, such as polyimide, provided with an electrically conductive metal film and the like. The cover 8*c* is formed in the same shape as the recess 5*c* and covering the recess 5*c*, and the upper surface runs flush with the outer surface of the curler 5 on the shorter side when the cover 8*c* is provided in the recess 5*c*.

Next, as illustrated in FIG. 32, an example of a method for manufacturing the blood pressure measurement device 1 will be described.

First, the power feeding unit 8 is formed on the curler 5 (step ST1). The FPC constituting the wiring portion 8*a* and the power feeding terminal 8*b* is joined to the cover portion 5*a* and the recess 5*c* of the curler 5 by double-sided tape or the like and the cover 8*c* is joined to the recess 5*c* by double-sided tape of the like.

Next, the cuff structure 6 is joined to the curler 5 (step ST2). In a specific example, first, the back plate 72 is disposed in a jig for curving and heated in a heating furnace to heat treat the back plate 72 and curve it in a predetermined shape. Next, the joining layer 75, i.e., double-sided tape, is attached to a region of the fourth sheet member 86d of the pressing cuff 71 facing the curler 5 and the target join portion 82, and the pressing cuff 71 is attached to the curler 5. Then, double-sided tape is attached to the region of the sixth sheet member 96b of the sensing cuff 73 facing the back plate 72, and the sensing cuff 73 is attached to the back plate 72. Note that in these steps, the connection portion 84 of the pressing cuff 71 and the connection portion 93 of the sensing cuff 73 are inserted into the first hole portion 5f1 and the second hole portion 5f2 of the cover portion 5a of the curler 5.

Next, double-sided tape is attached to the region of the back plate 72 facing the pressing cuff 71, and the back plate 72 is attached to the first sheet member 86a of the pressing cuff 71. Then, double-sided tape is attached to the region of the eighteenth sheet member 106l of the tensile cuff 74 facing the curler 5 and the target join portion 102, and the tensile cuff 74 is attached to the curler 5, the flow path body 83 of the pressing cuff 71 disposed on the inner surface of the curler 5, and the flow path body 92 of the sensing cuff 73. These steps join the cuff structure 6 to the curler 5.

Next, the sealing member 36 and the rear cover 35 are disposed on the cover portion 5a and the rear cover 35 is fixed to the cover portion 5a with the first joining members 35a (step ST3) to constitute a rear lid.

Then, the device body 3 is integrally assembled except for the rear cover 35 (step ST4). In a specific example, first, the first on-off valve 16A, the second on-off valve 16B, the third on-off valve 16C, the fourth on-off valve 16D, the first pressure sensor 17A, and the second pressure sensor 17B are fixed to the support plate 38.

Next, for example, the adhesive G is applied to the dividing grooves 34C3, 34C4, 34C6, and 34C7 of the flow path plate 34.

By pressing the flow path plate 34 against the base portion 33, the adhesive G is also collected in the grooves 33B, 33C1, 33C2, and 33C5 of the base portion 33.

A portion of the adhesive G that enters in the flow path portions 141, 142, 143 and 144 when the flow path plate 34 is pressed against the base portion 33 is collected in the adhesive escape portions 141d, 142d, 143d, and 144d respectively formed in the peripheral region of the flow path grooves of the flow path portions 141, 142 and 143.

Next, the adhesive G is cured by being irradiated with ultraviolet light.

Then, the components, such as the first on-off valve 16A, the second on-off valve 16B, the third on-off valve 16C, the fourth on-off valve 16D, the first pressure sensor 17A, and the second pressure sensor 17B, which are installed on the base portion 33 are installed on the base portion 33. Next, the first tube 15b, the second tube 15c, and the third tube 15d are installed on the flow path portion 15. After completing these steps, the assembly of the device body 3 is complete.

Next, the rear cover 35 is disposed on the end portion on the wrist 200 side of the outer case 31 of the device body 3, and the outer case 31 and the rear cover 35 are fixed with the second joining members 35b (step ST5). Then, the first belt 61 and the second belt 62 are assembled on the outer case 31 (step ST6). With these steps, the blood pressure measurement device 1 is manufactured. Note that, after manufacturing the blood pressure measurement device 1, adjustments of various parameters in the device body, an appearance inspection, a leak inspection and the like are performed. And the blood pressure measurement device 1 is engraved with a serial number and the like, and packed in an individual box and the like, and thus the blood pressure measurement device 1 is in a shipment state.

Next, an example of attaching the blood pressure measurement device 1 will be described using FIGS. 33 to 35. Additionally, FIGS. 33 to 35 illustrate an example in which the blood pressure measurement device 1 is attached to the wrist 200 of a user.

As illustrated in FIG. 33, first, the user inserts one of the wrists 200 into the curler 5, for example.

At this time, in the blood pressure measurement device 1, the device body 3 and the sensing cuff 73 are disposed at opposite positions in the curler 5, and thus the sensing cuff 73 is disposed in a region on the hand palm-side of the wrist 200 in which the artery 210 resides. Thus, the device body 3 and the tensile cuff 74 are disposed on the hand back side of the wrist 200.

Then, as illustrated in FIG. 34, the user passes the second belt 62 through the frame body 61e of the buckle 61b of the first belt 61 with the hand opposite to the hand on which the blood pressure measurement device 1 is disposed. The user then pulls the second belt 62 to bring the member on the inner circumferential surface side of the curler 5, that is, the cuff structure 6, into close contact with the wrist 200, and inserts the prong 61f into one of the small holes 62a. Thus, as illustrated in FIGS. 4 and 35, the first belt 61 and the second belt 62 are connected, and the blood pressure measurement device 1 is attached to the wrist 200.

An example of the operations of the blood pressure measurement device 1 will now be described using FIG. 36. FIG. 36 illustrates a flow of the operations of the control unit 55.

The control unit 55, on the basis of a blood pressure measurement command, for example, opens the first on-off valve 16A, the second on-off valve 16B, and the third on-off valve 16C, closes the pump valve 14b and the fourth on-off valve 16D, and operates the pump 14 to supply compressed air to the pressing cuff 71, the sensing cuff 73, and the tensile cuff 74 through the first flow path 7a, the second flow path 7b, the third flow path 7c, and the fourth flow path 7d (step ST11). Thus, the pressing cuff 71, the sensing cuff 73, and the tensile cuff 74 start to be inflated.

The first pressure sensor 17A and the second pressure sensor 17B detect the pressures in the pressing cuff 71, the sensing cuff 73, and the tensile cuff 74, and output, to the control unit 55, electrical signals corresponding to the pressures (step ST12). On the basis of the received electrical signals, the control unit 55 determines whether the pressures in the internal spaces of the pressing cuff 71, the sensing cuff 73, and the tensile cuff 74 have reached a predetermined pressure for measurement of the blood pressure (step ST13). For example, in a case where the internal pressures of the pressing cuff 71 and the tensile cuff 74 have not reached the predetermined pressure and the internal pressure of the sensing cuff 73 has reached the predetermined pressure, the control unit 55 closes the first on-off valve 16A and supplies the compressed air through the second flow path 7b, the third flow path 7c, and the fourth flow path 7d.

When the internal pressures of the pressing cuff 71 and the tensile cuff 74 and the internal pressure of the sensing cuff 73 all have reached the predetermined pressure, the control unit 55 stops driving the pump 14 (YES in step ST13). At this time, as illustrated by the two-dot chain line in FIG. 4, the pressing cuff 71 and the tensile cuff 74 are sufficiently inflated, and the inflated pressing cuff 71 presses the back plate 72. Additionally, the tensile cuff 74 presses against the curler 5 in a direction away from the wrist 200, and then the belt 4, the curler 5, and the device body 3 move in a direction away from the wrist 200, and as a result, the pressing cuff 71, the back plate 72, and the sensing cuff 73 are pulled toward the wrist 200 side. In addition, when the belt 4, the curler 5, and the device body 3 move in a direction away from the wrist 200 due to the inflation of the tensile cuff 74, the belt 4 and the curler 5 move toward both lateral sides of the wrist 200, and the belt 4, the curler 5, and the device body 3 move in a state of close contact with both lateral sides of the wrist 200. Thus, the belt 4 and the curler 5, which are in close contact with the skin of the wrist 200, pull the skin on both lateral sides of the wrist 200 toward the hand back side. Note that the curler 5 may be configured to indirectly contact the skin of the wrist 200 with the sheet members 86 or 106 in between, for example, as long as the curler 5 can pull the skin of the wrist 200.

Furthermore, the sensing cuff 73 is inflated by being supplied with a predetermined amount of air such that the internal pressure equals the pressure required to measure blood pressure, and is pressed toward the wrist 200 by the back plate 72 that is pressed by the pressing cuff 71. Thus, the sensing cuff 73 presses the artery 210 in the wrist 200 and occludes the artery 210 as illustrated in FIG. 37.

Additionally, the control unit 55, for example, controls the third on-off valve 16C and repeats the opening and closing of the third on-off valve 16C, or adjusts the degree of opening of the third on-off valve 16C to pressurize a pressure of the internal space of the pressing cuff 71. In the process of pressurization, on the basis of the electrical signal output by the first pressure sensor 17A and the second pressure sensor 17B, the control unit 55 obtains measurement results such as blood pressure values, for example, the systolic blood pressure and the diastolic blood pressure, and the heart rate and the like (step ST14). The control unit 55 outputs an image signal corresponding to the obtained measurement results to the display unit 12, and displays the measurement results on the display unit 12 (step ST15). In addition, after the end of the blood pressure measurement, the control unit 55 opens the first on-off valve 16A, the second on-off valve 16B, the third on-off valve 16C, and the fourth on-off valve 16D.

The display unit 12 receives the image signal, and then displays the measurement results on the screen. The user views the display unit 12 to confirm the measurement results. After the measurement is complete, the user removes the prong 61f from the small hole 62a, removes the second belt 62 from the frame body 61e, and pulls out the wrist 200 from the curler 5, thus detaching the blood pressure measurement device 1 from the wrist 200.

Next, an example of pressure monitoring and safety control by the control unit 55 will be described using FIG. 38.

When the blood pressure measurement device 1 starts operations on the basis of program data, for example, the control unit 55 starts monitoring the pressure on the basis of the electrical signals received from the first pressure sensor 17A and the second pressure sensor 17B.

Specifically, when the pump 14 is started to be driven in step ST11 as illustrated in FIG. 36, the control unit 55 determines whether there is a failure on the basis of the electrical signals received from the first pressure sensor 17A and the second pressure sensor 17B and the threshold stored in the storage unit 54, as illustrated in FIG. 38 (step ST21).

The control unit 55 determines whether there is a failure in the pump valve 14b, the first on-off valve 16A, the second on-off valve 16B, the third on-off valve 16C, or the fourth on-off valve 16D on the basis of the threshold, which is stored in the storage unit 54, set with respect to the operation based on the program data of the blood pressure measurement device 1 and the electrical signals received from the first pressure sensor 17A and the second pressure sensor 17B.

In the failure determination after blood pressure measurement is complete, for example, the control unit 55 determines that there is a failure in any one of the pump valve 14b, the first on-off valve 16A, the second on-off valve 16B, the third on-off valve 16C, or the fourth on-off valve 16D, in a case where the pressures indicated by the first pressure sensor 17A and the second pressure sensor 17B do not reach the atmospheric pressure, even after a predetermined amount of time, i.e., a threshold, has passed since control to open the on-off valves 16A, 16B, 16C, and 16D was performed to open the sensing cuff 73, the tensile cuff 74, and the pressing cuff 71 to the atmosphere after blood pressure measurement completion.

Also, in the failure determination during blood pressure measurement, the third on-off valve 16C is determined to be malfunctioning in a case where, for example, there is a step of expanding the tensile cuff 74 to a state suitable for blood pressure measurement after a step of expanding the pressing cuff 71 to a state suitable for blood pressure measurement, the speed of the rise in pressure of the second flow path portion 142 from when a signal to close the third on-off valve 16C is transmitted in the step of expanding the tensile cuff 74 to a state suitable for blood pressure measurement is slow, or in other words when the time taken to rise a pressure of the second flow path portion 142 to a preset predetermined pressure is longer than a preset amount of time, i.e., the threshold.

Note that the failure determination described above is merely an example, and no such limitation is intended.

When the control unit 55 determines that there is a failure in at least one of the pump valve 14b, the first on-off valve 16A, the second on-off valve 16B, the third on-off valve 16C, or the fourth on-off valve 16D, the control unit 55 stops driving the pump body 14a of the pump 14 (step ST22). Next, the control unit 55 transmits an open instruction to the pump valve 14b, the first on-off valve 16A, the second on-off valve 16B, the third on-off valve 16C, and the fourth on-off valve 16D (step ST23). This instruction makes the valves other than the malfunctioning valve open.

For example, in a case where the pump valve 14b is malfunctioning, the sensing cuff 73, the tensile cuff 74, and the pressing cuff 71 are opened to the atmosphere through the fourth on-off valve 16D, discharging the air inside the sensing cuff 73, the tensile cuff 74, and the pressing cuff 71 through the fourth on-off valve 16D.

For example, in a case where the first on-off valve 16A is malfunctioning, compressed air cannot be supplied inside the sensing cuff 73. Thus, the pressure of the internal space of the sensing cuff 73 does not rise. Accordingly, the sensing cuff 73 does not need to be opened to the atmosphere. Because the tensile cuff 74 and the pressing cuff 71 are opened to the atmosphere through the fourth on-off valve 16D, the tensile cuff 74 and the pressing cuff 71 discharge air through the fourth on-off valve 16D.

In a case where the second on-off valve 16B is malfunctioning, the sensing cuff 73 is opened to the atmosphere through the pump valve 14b. Thus, the sensing cuff 73 discharges air through the second on-off valve 16B. The tensile cuff 74 and the pressing cuff 71 are opened to the atmosphere through the fourth on-off valve 16D, discharging the air inside the tensile cuff 74 and the pressing cuff 71 through the fourth on-off valve 16D.

In a case where the third on-off valve 16C is malfunctioning, compressed air cannot be supplied to the tensile cuff 74. Thus, the tensile cuff 74 does not need to be opened to the atmosphere. Because the sensing cuff 73 is opened to the atmosphere through the pump valve 14b, the air inside the sensing cuff 73 is discharged through the pump valve 14b. The pressing cuff 71 are opened to the atmosphere through the fourth on-off valve 16D, discharging the air inside the fourth on-off valve 16D through the fourth on-off valve 16D.

In a case where the fourth on-off valve 16D is malfunctioning, the sensing cuff 73, the tensile cuff 74, and the pressing cuff 71 are opened to the atmosphere through the pump valve 14b, discharging the air inside the sensing cuff 73, the tensile cuff 74, and the pressing cuff 71 through the pump valve 14b.

The blood pressure measurement device 1 according to the present embodiment with such a configuration includes the pump 14 including the pump valve 14b, the first flow path 7a including the first on-off valve 16A, the second flow path 7b including the second on-off valve 16B, the third on-off valve 16C, and the fourth on-off valve 16D, the third flow path 7c, and the fourth flow path 7d.

Thus, even in a case where either one of the pump valve 14b, the first on-off valve 16A, the second on-off valve 16B, the third on-off valve 16C, or the fourth on-off valve 16D is malfunctioning and cannot open, the sensing cuff 73, the tensile cuff 74, and the pressing cuff 71 can be opened to the atmosphere through the pump valve 14b or the fourth on-off valve 16D. Thus, the air inside the sensing cuff 73, the tensile cuff 74, and the pressing cuff 71 can be discharged through the pump valve 14b or the fourth on-off valve 16D.

In addition, in a case where the control unit 55 determines the failure of any one of the pump valve 14b, the first on-off valve 16A, the second on-off valve 16B, the third on-off valve 16C, or the fourth on-off valve 16D on the basis of the electrical signals from the first pressure sensor 17A and the second pressure sensor 17B and the threshold stored in the storage unit 54, all of the valves are opened. Thus, even in a state where the user is unaware of the irregularity in the blood pressure measurement device 1 such as night time, for example, the air of the internal space of the sensing cuff 73, the tensile cuff 74, and the pressing cuff 71 are each discharged through the pump valve 14b or the fourth on-off valve 16D. In this manner, the safety of the blood pressure measurement device 1 is improved.

Furthermore, the flow path portion 15 forming a portion of the fluid circuit 7 is provided with the flow path portion body 15a formed between the base portion 33 and the flow path plate 34 and the first tube 15b, the second tube 15c, and the third tube 15d provided on the windshield side of the base portion 33.

In this manner, by using the tubes 15b, 15c and 15d, the size of the flow path portion 15 can be decreased in the direction orthogonal to the axial direction D of the outer case 31. Thus, the size of the device body 3 can be decreased in the direction orthogonal to the axial direction D of the outer case 31.

Furthermore, the first flow path portion 141 includes the first flow path groove 141c. Accordingly, because a width of the flow path through which the compressed air mainly flows can be decreased, the amount of air collected inside the first flow path portion 141 can be decreased. The same applies to the second flow path portion 142, the third flow path portion 143, and the fourth flow path portion 144. Thus, air can be efficiently supplied from the pump 14 to the sensing cuff 73, the tensile cuff 74, and the pressing cuff 71.

Furthermore, the first flow path portion 141 is constituted with an escape portion for the adhesive G at the peripheral region of the first flow path groove 141c. The same applies to the second flow path portion 142, the third flow path portion 143, and the fourth flow path portion 144. This allows to prevent the first flow path groove 141c, the second flow path groove 142c, the third flow path groove 143c, and the fourth flow path groove 144c from being blocked by the adhesive G.

Furthermore, the power supply unit 18 is fixed to the windshield 32 side of the pump 14, and the first on-off valve 16A, the second on-off valve 16B, the third on-off valve 16C, and the fourth on-off valve 16D are disposed at a position separated from the pump 14 and the power supply unit 18 in the axial direction D of the outer case 31. In other words, the first on-off valve 16A, the second on-off valve 16B, the third on-off valve 16C, and the fourth on-off valve 16D are not disposed at a position facing the pump 14 and the power supply unit 18 in the axial direction D of the outer case 31. Thus, the device body 3 can be made thinner.

Also, the first on-off valve 16A, the second on-off valve 16B, the third on-off valve 16C, the fourth on-off valve 16D, the first pressure sensor 17A, and the second pressure sensor 17B are disposed in a region surrounded by an arc-shape edge of the base portion 33. By disposing the pump valve 14b, the first on-off valve 16A, the second on-off valve 16B, the third on-off valve 16C, the fourth on-off valve 16D, the first pressure sensor 17A, and the second pressure sensor 17B in a region surrounded by an arc-shape edge of the base portion 33, the space in the center region of the base portion 33 can be effectively used. Thus, flexibility in the layout of the components of the blood pressure measurement device 1 on the base portion 33 can be improved.

In the example described above, the outer case 31 is formed in a cylindrical shape as an example. However, no such limitation is intended. The outer case 31 may be formed in a rectangular tube-like shape, for example.

In other words, the embodiments described above are merely examples of the present invention in all respects. Of course, various modifications and variations can be made without departing from the scope of the present invention. Thus, specific configurations in accordance with an embodiment may be adopted as appropriate at the time of carrying out the present invention.

REFERENCE SIGNS LIST

1 Blood pressure measurement device
3 Device body
4 Belt
5 Curler
5a Cover portion
5b Escape portion
5c Insert member
6 Cuff structure
7 Fluid circuit
7a First flow path
7b Second flow path
7c Third flow path
11 Case
12 Display unit
13 Operation unit
14 Pump
15 Flow path portion
15a Flow path portion body 15b First tube
15c Second tube
15d Third tube
16 On-off valve
16A First on-off valve
16B Second on-off valve
16C Third on-off valve
16D Fourth on-off valve
17 Pressure sensor
17A First pressure sensor
17B Second pressure sensor
18 Power supply unit
19 Vibration motor
20 Control substrate
31 Outer case
31a Lug
31b Spring rod
32 Windshield
33 Base portion
33A1 First hole
33A2 Second hole
33A3 Third hole
33A4 Fourth hole
33A5 Fifth hole
33A6 Sixth hole
33A7 Seventh hole
33A8 Eighth hole
33A10 Tenth hole
33A12 Twelfth hole
33B Groove
33C1 First dividing groove
33C2 Second dividing groove
33C5 Fifth dividing groove
34 Flow path plate
34A11 Eleventh hole
34A14 Fourteenth hole
34A9 Ninth hole
34B1 First projection portion
34B2 Second projection portion
34B3 Third projection portion
34B4 Fourth projection portion
34C3 Third dividing groove
34C4 Fourth dividing groove
34C6 Sixth dividing groove
34C7 Seventh dividing groove
34D1 First nozzle
34D2 Second nozzle
34D3 Third nozzle
35 Rear cover
35a First joining member
35b Second joining member
41 Button
42 Sensor
43 Touch panel
51 Substrate
52 Acceleration sensor
53 Communication unit
54 Storage unit
55 Control unit
56 Main CPU
57 Sub-CPU
61 First belt
61a Belt portion
61b Buckle
61c First hole portion
61d Second hole portion
61e Frame body
61f Prong
62 Second belt
62a Small hole
62b Third hole portion
71 pressing cuff
72 Back plate
72a Groove
73 Sensing cuff
74 Tensile cuff
81 Air bag (bag-like structure)
84 Connection portion
86 Sheet member
86a First sheet member
86b Second sheet member
86b1 Opening
86c Third sheet member
86c1 Opening
86d Fourth sheet member
91 Air bag (bag-like structure)
92 Flow path body
93 Connection portion
96 Sheet member
96a Fifth sheet member
96b Sixth sheet member
101 Air bag (bag-like structure)
103 Connection portion
106 Sheet member
106a Seventh sheet member
106b Eighth sheet member
106b1 Opening
106c Ninth sheet member
106c1 Opening
106d Tenth sheet member
106d1 Opening
106e Eleventh sheet member
106e1 Opening
106f Twelfth sheet member
106f1 Opening
106g Thirteenth sheet member
106g1 Opening
106h Fourteenth sheet member
106h1 Opening
106i Fifteenth sheet member
106i1 Opening
106j Sixteenth sheet member
106j1 Opening
106k Seventeenth sheet member
106k1 Opening
106l Eighteenth sheet member
141 First flow path portion
141a Base portion side first structure portion
141b Flow path plate side first structure portion
141c First flow path groove
141d Escape portion
142 Second flow path portion
142a Base portion side second structure portion
142b Flow path plate side second structure portion
142c Second flow path groove
142d Escape portion
143 Third flow path portion
143a Base portion side third structure portion
143b Flow path plate side third structure portion
143c Third flow path groove
143d Escape portion
144 Fourth flow path portion
144a Base portion side fourth structure portion
144b Flow path plate side fourth structure portion 144c Fourth flow path groove
144d Escape portion
200 Wrist
210 Artery

The invention claimed is:

1. A blood pressure measurement device attachable to a living body, the blood pressure measurement device comprising:
- a cuff structure including a sensing cuff, a tensile cuff, and a pressing cuff that are configured to be inflated by a fluid;
- a pump including a pump body and a pump valve;
- a first flow path including a first on-off valve and fluidly connecting the pump and the sensing cuff through the first on-off valve;
- a second flow path configured by branching from the first flow path between the pump and the first on-off valve, including a second on-off valve, a third on-off valve, and a fourth on-off valve, and connecting the pump and atmosphere through the second on-off valve, the third on-off valve, and the fourth on-off valve sequentially in that order;
- a third flow path configured by branching from the second flow path at an intermediate portion between the second on-off valve and the third on-off valve and fluidly connecting the pump and the tensile cuff; and
- a fourth flow path configured by branching from the second flow path at an intermediate portion between the third on-off valve and the fourth on-off valve and fluidly connecting the pump and the pressing cuff;
- a pressure sensor provided on the first flow path at an intermediate portion between the first on-off valve and the sensing cuff;
- a storage unit configured to store a threshold for pressure for determining failure of the pump valve, the first on-off valve, the second on-off valve, the third on-off valve, and the fourth on-off valve; and
- a control unit configured to determine failure of one of the pump valve, the first on-off valve, the second on-off valve, the third on-off valve, or the fourth on-off valve on the basis of a signal from the pressure sensor and the threshold, and open the other valves.

2. The blood pressure measurement device according to claim 1, further comprising:
- a case including an outer case having a cylindrical shape and a windshield covering a first end of the outer case;
- a base portion installed with the pump, the first on-off valve, the second on-off valve, the third on-off valve, and the fourth on-off valve, the base portion being housed inside the case;
- a flow path plate fixed to the base portion on a living body side, the flow path plate constituting, with the base portion, a portion of the first flow path, a portion of the second flow path, a portion of the third flow path, and a portion of the fourth flow path;
- a first tube provided on the base portion on a windshield side, the first tube constituting another portion of the first flow path; and
- a second tube and a third tube provided on a surface of the base portion on the windshield side, the second tube and the third tube constituting another portion of the second flow path.

3. The blood pressure measurement device according to claim 2, wherein
the base portion and the flow path plate are fixed by adhesive, and
the portion of the first flow path, the portion of the second flow path, the portion of the third flow path, and the portion of the fourth flow path each include a flow path groove formed in one of the base portion and the flow path plate and covered by another one of the base portion and the flow path plate, and an escape portion for the adhesive, the escape portion is provided in a peripheral region of the flow path groove.

4. The blood pressure measurement device according to claim 2, further comprising:
a power supply unit fixed to a surface of the pump on the windshield side, wherein
the first on-off valve, the second on-off valve, the third on-off valve, and the fourth on-off valve are disposed at positions separated from the pump in a direction orthogonal to an axial direction of the outer case.

5. The blood pressure measurement device according to claim 3, wherein
the first on-off valve, the second on-off valve, the third on-off valve, and the fourth on-off valve are disposed along an inner surface of the outer case inside the case.

* * * * *